(12) United States Patent
Tieck

(10) Patent No.: US 10,010,668 B2
(45) Date of Patent: Jul. 3, 2018

(54) OCCLUSION DETECTION TECHNIQUES FOR A FLUID INFUSION DEVICE HAVING A ROTARY PUMP MECHANISM AND A FORCE SENSOR

(71) Applicant: MEDTRONIC MINIMED, INC., Northridge, CA (US)

(72) Inventor: R. Marie Tieck, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 100 days.

(21) Appl. No.: 14/746,634

(22) Filed: Jun. 22, 2015

(65) Prior Publication Data

US 2016/0367750 A1  Dec. 22, 2016

(51) Int. Cl.
| | |
|---|---|
| *A61M 5/142* | (2006.01) |
| *F04B 9/04* | (2006.01) |
| *F04B 19/22* | (2006.01) |
| *A61M 5/168* | (2006.01) |

(52) U.S. Cl.
CPC .... *A61M 5/14216* (2013.01); *A61M 5/16831* (2013.01); *F04B 9/042* (2013.01); *F04B 19/22* (2013.01); *A61M 2005/16868* (2013.01)

(58) Field of Classification Search
CPC .......... A61M 5/14216; A61M 5/16831; A61M 2005/16868; F04B 9/042; F04B 9/22
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |

(Continued)

FOREIGN PATENT DOCUMENTS

| | | |
|---|---|---|
| AU | 2011232741 A1 | 10/2011 |
| DE | 4329229 | 3/1995 |

(Continued)

OTHER PUBLICATIONS (Animas Corporation, 1999). Animas . . . bringing new life to insulin therapy.

(Continued)

*Primary Examiner* — Imani Hayman
*Assistant Examiner* — Lauren P Farrar
(74) *Attorney, Agent, or Firm* — Lorenz & Kopf, LLP

(57) ABSTRACT

An embodiment of a fluid infusion device includes a fluid pump mechanism having a rotor and a stator. The rotor includes a reference surface and a cam element rising from the reference surface. The stator includes a cam element having a stator cam surface. The cam elements cooperate to axially displace the rotor as a function of rotation. A biasing element provides force to urge the cam elements together. A drive motor is coupled to actuate the rotor to pump medication fluid from a fluid cartridge module to a body, via a subcutaneous conduit. A force sensor is coupled to the rotor to generate output levels in response to force imparted thereto. The force sensor cooperates with a detection circuit that obtains and processes the output levels to detect occlusions in a fluid path downstream of the fluid pump mechanism.

4 Claims, 24 Drawing Sheets

(56) References Cited

U.S. PATENT DOCUMENTS

| | | |
|---|---|---|
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,856,339 A | 8/1989 | Williams |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,053,873 A | 4/2000 | Govari et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |

(56) References Cited

U.S. PATENT DOCUMENTS

| | | |
|---|---|---|
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 8,282,366 B2 | 10/2012 | Hilber et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0207385 A1* | 10/2004 | Gafner ............... A61M 5/31556 324/76.11 |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0084402 A1 | 4/2005 | Vanek |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2009/0123309 A1* | 5/2009 | Hilber ............... A61M 5/14244 417/417 |
| 2013/0017099 A1 | 1/2013 | Genoud et al. |
| 2014/0046288 A1 | 2/2014 | Geipel et al. |
| 2014/0324018 A1* | 10/2014 | Bazargan ............ A61M 5/1456 604/506 |

FOREIGN PATENT DOCUMENTS

| | | |
|---|---|---|
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| EP | 1803934 A1 | 7/2007 |
| EP | 2275678 A1 | 1/2011 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | 02/03299 | 10/2002 |
| WO | WO 03/001329 | 1/2003 |
| WO | WO 03/094090 | 11/2003 |
| WO | WO 2005/065538 A2 | 7/2005 |
| WO | WO 2011114285 A2 | 9/2011 |

OTHER PUBLICATIONS

Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.

(56) References Cited

OTHER PUBLICATIONS

Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wde Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytics Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artificial endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl
nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

(56) References Cited

OTHER PUBLICATIONS

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-lnnsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

OCCLUSION DETECTION TECHNIQUES FOR A FLUID INFUSION DEVICE HAVING A ROTARY PUMP MECHANISM AND A FORCE SENSOR

TECHNICAL FIELD

Embodiments of the subject matter described herein relate generally to fluid infusion devices of the type suitable for delivering a medication fluid to the body of a patient. More particularly, embodiments of the subject matter presented herein relate to techniques for detecting an occlusion in the fluid delivery path of a fluid infusion device having a rotary pump mechanism.

BACKGROUND

Certain diseases or conditions may be treated, according to modern medical techniques, by delivering a medication fluid or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., insulin pumps) to deliver controlled amounts of insulin to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic bedside environment), and devices configured for ambulatory or portable use (to be carried or worn by a patient). External fluid infusion devices may establish a fluid flow path from a fluid reservoir or cartridge to the patient via, for example, a suitable hollow tubing, needle, or other type of fluid conduit.

A fluid infusion device can be implemented with a rotary micropump mechanism that accurately delivers a precise volume of fluid with each revolution or cycle. The inlet of the micropump is connected to a fluid source such as a reservoir, and the outlet of the micropump is connected to a fluid delivery conduit that leads to the body of the patient. Under normal operating conditions, the micropump draws fluid from the fluid source (via a vacuum or suction action) and then delivers a predictable volume of fluid with each cycle.

It is desirable to reliably and accurately detect at least two conditions, for purposes of alerting the user and/or to otherwise control the operation of the fluid infusion device in a responsive manner. One of these "fault" conditions is a downstream occlusion in the fluid delivery path (e.g., a blockage downstream from the outlet of the micropump). Another "fault" condition is an upstream occlusion (e.g., a blockage located before the inlet of the micropump). In this regard, an empty fluid reservoir can be considered to be an upstream occlusion because continued operation of the micropump in the presence of an empty reservoir does not result in the normally expected delivery of fluid.

Accordingly, it is desirable to have a fluid infusion device and related operating methodologies that effectively detect upstream and/or downstream occlusions in the fluid delivery pathway associated with a rotary micropump. In addition, it is desirable to provide an improved rotary micropump having certain features and functionality that facilitate the detection of upstream and/or downstream occlusions in the fluid delivery pathway. Furthermore, other desirable features and characteristics will become apparent from the subsequent detailed description and the appended claims, taken in conjunction with the accompanying drawings and the foregoing technical field and background.

BRIEF SUMMARY

Various upstream and downstream occlusion detection techniques and methodologies are disclosed herein. The occlusion detection techniques and methodologies can be implemented in a fluid infusion device that includes a rotary fluid pump mechanism (having a rotor and a stator). Actuation of the fluid pump mechanism draws fluid from a fluid reservoir during an intake stroke and expels the fluid during a delivery stroke.

In accordance with certain embodiments, the fluid pump mechanism includes a stator having a fluid chamber defined therein, and also having a stator cam element with a stator cam surface. The fluid pump mechanism also includes a rotor having an endcap with a reference surface, an axial extension section protruding from the endcap, wherein at least a portion of the axial extension section fits inside the fluid chamber, and a rotor cam element having a variable height rising from the reference surface. The rotor cam element cooperates with the stator cam element to axially displace the rotor, relative to the stator, as a function of angular position of the rotor. A sensor contact element resides on the reference surface and is located in an area that is unoccupied by the rotor cam element. A sensing element terminates at or near the stator cam surface. The sensing element cooperates with a detection circuit to detect whether or not the stator cam surface is in contact with the sensor contact element. The detection circuit monitors characteristics of a detection signal obtained from the sensing element in response to angular position of the rotor to determine an operating condition of the fluid pump mechanism.

Also presented here is an exemplary embodiment of a fluid infusion device for delivering a medication fluid to a body. The fluid infusion device includes a fluid pump mechanism that cooperates with a fluid cartridge module. The fluid pump mechanism has a rotor and a stator, wherein the rotor includes a reference surface and a rotor cam element having a variable height rising from the reference surface. The stator includes a stator cam element having a stator cam surface, wherein the rotor cam element cooperates with the stator cam element to axially displace the rotor, relative to the stator, as a function of angular position of the rotor. The fluid infusion device also includes a subcutaneous conduit in fluid communication with an outlet valve of the fluid pump mechanism, and a drive motor coupled to actuate the rotor of the fluid pump mechanism to pump medication fluid from the fluid cartridge module to the body, via the subcutaneous conduit. A sensor contact element is provided on the reference surface of the rotor. The sensor contact element is located in an area that is unoccupied by the rotor cam element. A sensing element terminates at or near the stator cam surface. The sensing element cooperates with a detection circuit to detect whether or not the stator cam surface is in contact with the sensor contact element. The detection circuit monitors characteristics of a detection signal obtained from the sensing element in response to angular position of the rotor to determine an operating condition of the fluid pump mechanism.

An exemplary embodiment of a fluid pump mechanism is also presented here. The fluid pump mechanism includes: a stator; a rotor; an inlet valve that opens and closes as a function of angular and axial position of the rotor; an outlet valve that opens and closes as a function of angular and axial position of the rotor; a sensor contact element; and a sensing element. The stator cam element has a stator cam surface, and the rotor includes a reference surface and a rotor cam element having a variable height rising from the reference surface. The rotor cam element cooperates with the stator cam element to axially displace the rotor, relative to the stator, as a function of angular position of the rotor. The sensor contact element resides on the reference surface in an area corresponding to a valve state in which the inlet valve is closed and the outlet valve is open. The sensing element terminates at or near the stator cam surface, and it cooperates with a detection circuit to detect whether or not the stator cam surface is in contact with the sensor contact element. The detection circuit monitors characteristics of a detection signal obtained from the sensing element in response to angular position of the rotor to determine an operating condition of the fluid pump mechanism.

Another exemplary embodiment of a fluid pump mechanism employs a force sensor to detect occlusions in the fluid path. The fluid pump mechanism includes a stator with a stator cam element having a stator cam surface. The fluid pump mechanism also includes a rotor with a reference surface and a rotor cam element having a variable height rising from the reference surface. The rotor cam element cooperates with the stator cam element to axially displace the rotor, relative to the stator, as a function of angular position of the rotor. A biasing element provides a biasing force to urge the rotor cam element toward the stator cam element and toward the reference surface. A force sensor is coupled to the rotor. The force sensor generates output levels in response to force imparted thereto, and the force sensor cooperates with a detection circuit that obtains and processes the output levels to detect occlusions in a fluid path downstream of the fluid pump mechanism.

An exemplary embodiment of a fluid infusion device includes a fluid pump mechanism that cooperates with a fluid cartridge module. The fluid pump mechanism has a rotor and a stator. The rotor includes a reference surface and a rotor cam element having a variable height rising from the reference surface. The stator includes a stator cam element having a stator cam surface, wherein the rotor cam element cooperates with the stator cam element to axially displace the rotor, relative to the stator, as a function of angular position of the rotor. A biasing element provides a biasing force to urge the rotor cam element toward the stator cam element and toward the reference surface. The fluid infusion device also includes a subcutaneous conduit in fluid communication with an outlet valve of the fluid pump mechanism, and a drive motor coupled to actuate the rotor of the fluid pump mechanism to pump medication fluid from the fluid cartridge module to the body, via the subcutaneous conduit. A force sensor is coupled to the rotor to generate output levels in response to force imparted thereto. The force sensor cooperates with a detection circuit that obtains and processes the output levels to detect occlusions in a fluid path downstream of the fluid pump mechanism.

An exemplary embodiment of a fluid infusion device includes a stator with a stator cam element having a stator cam surface, and a rotor with a reference surface and a rotor cam element having a variable height rising from the reference surface. The rotor cam element cooperates with the stator cam element to axially displace the rotor, relative to the stator, as a function of angular position of the rotor. A biasing element provides a biasing force to urge the rotor cam element toward the stator cam element and toward the reference surface. The fluid infusion device also includes an inlet valve that opens and closes as a function of angular and axial position of the rotor, and an outlet valve that opens and closes as a function of angular and axial position of the rotor. A force sensor is coupled to the rotor to generate output levels in response to force imparted thereto. A detection circuit cooperates with the force sensor to obtain and process the output levels of the force sensor to detect occlusions in a fluid path downstream of the fluid pump mechanism.

In accordance with other exemplary embodiments, a fluid pump mechanism includes a stator with a stator cam element having a stator cam surface, and a rotor with an optically detectable feature, a reference surface, and a rotor cam element having a variable height rising from the reference surface. The rotor cam element cooperates with the stator cam element to axially displace the rotor, relative to the stator, as a function of angular position of the rotor. The optically detectable feature rotates and axially translates as a function of angular position of the rotor. An optical detection circuit interrogates the optically detectable feature during operation of the fluid pump mechanism to determine an operating condition of the fluid pump mechanism.

An exemplary embodiment of a fluid infusion device includes a fluid pump mechanism that cooperates with a fluid cartridge module. The fluid pump mechanism includes a rotor and a stator, wherein the rotor has an optically detectable feature, a reference surface, and a rotor cam element having a variable height rising from the reference surface. The stator includes a stator cam element having a stator cam surface, such that the rotor cam element cooperates with the stator cam element to axially displace the rotor, relative to the stator, as a function of angular position of the rotor. The optically detectable feature rotates and axially translates as a function of angular position of the rotor, and a biasing element provides a biasing force to urge the rotor cam element toward the stator cam element and toward the reference surface. The fluid infusion device also includes: a subcutaneous conduit in fluid communication with an outlet valve of the fluid pump mechanism; a drive motor coupled to actuate the rotor of the fluid pump mechanism to pump medication fluid from the fluid cartridge module to the body, via the subcutaneous conduit; and an optical detection circuit to interrogate the optically detectable feature during operation of the fluid pump mechanism to determine an operating condition of the fluid pump mechanism.

An exemplary embodiment of a fluid infusion device includes a stator with a stator cam element having a stator cam surface, and includes a rotor with an optically detectable feature, a reference surface, and a rotor cam element having a variable height rising from the reference surface. The rotor cam element cooperates with the stator cam element to axially displace the rotor, relative to the stator, as a function of angular position of the rotor. An inlet valve opens and closes as a function of angular and axial position of the rotor, and an outlet valve opens and closes as a function of angular and axial position of the rotor. An optical detection circuit cooperates with the optically detectable feature, wherein the optical detection circuit interrogates the optically detectable feature to determine an operating condition of the fluid infusion device.

In accordance with certain exemplary embodiments, a fluid pump mechanism includes a stator with a stator cam element having a stator cam surface, and a rotor with a reference surface and a rotor cam element having a variable height rising from the reference surface. The rotor cam element cooperates with the stator cam element to axially displace the rotor, relative to the stator, as a function of angular position of the rotor. A biasing element provides a biasing force to urge the rotor cam element toward the stator cam element and toward the reference surface. A detection circuit processes axial and angular position data of the rotor, and determines that an upstream occlusion has occurred based on detectable characteristics of the axial and angular position data.

An exemplary embodiment of a fluid infusion device includes: a fluid pump mechanism; a biasing element; a subcutaneous conduit; a drive motor; and a detection circuit. The fluid pump mechanism cooperates with a fluid cartridge module, and the fluid pump mechanism includes a rotor and a stator. The rotor includes a reference surface and a rotor cam element having a variable height rising from the reference surface, and the stator includes a stator cam element having a stator cam surface. The rotor cam element cooperates with the stator cam element to axially displace the rotor, relative to the stator, as a function of angular position of the rotor. The biasing element provides a biasing force to urge the rotor cam element toward the stator cam element and toward the reference surface. The subcutaneous conduit is in fluid communication with an outlet valve of the fluid pump mechanism. The drive motor is coupled to actuate the rotor of the fluid pump mechanism to pump medication fluid from the fluid cartridge module to the body, via the subcutaneous conduit. The detection circuit processes axial and angular position data of the rotor, and determines that an upstream occlusion has occurred based on detectable characteristics of the axial and angular position data.

An exemplary embodiment of a fluid infusion device includes a stator with a stator cam element having a stator cam surface, and a rotor with a reference surface and a rotor cam element having a variable height rising from the reference surface. The rotor cam element cooperates with the stator cam element to axially displace the rotor, relative to the stator, as a function of angular position of the rotor. A biasing element provides a biasing force to urge the rotor cam element toward the stator cam element and toward the reference surface. An axial position sensor obtains axial position data of the rotor, and an angular position sensor obtains angular position data of the rotor. A detection circuit obtains and processes the axial position data and the angular position data, wherein the detection circuit determines that an upstream occlusion has occurred based on processing of the axial position data and the angular position data.

In accordance with other exemplary embodiments, a fluid pump mechanism includes a stator with a stator cam element having a stator cam surface, and a rotor with a reference surface and a rotor cam element having a variable height rising from the reference surface. The rotor cam element cooperates with the stator cam element to axially displace the rotor, relative to the stator, as a function of angular position of the rotor. The fluid pump mechanism also includes an inlet valve that opens and closes as a function of angular and axial position of the rotor relative to the stator, and an outlet valve that opens and closes as a function of angular and axial position of the rotor relative to the stator. A biasing element provides a biasing force to urge the rotor toward the stator. A first sensor contact element resides on the rotor and is located at an angular position that follows an upper edge of the rotor cam element. A second sensor contact element resides on the rotor and is located at an angular position that follows the first sensor contact element. A sensing element resides on the stator, wherein the sensing element cooperates with a detection circuit to detect when the sensing element makes contact with the first sensor contact element and the second sensor contact element. The detection circuit monitors characteristics of a detection signal obtained from the sensing element in response to angular position of the rotor to determine an operating condition of the fluid pump mechanism.

An exemplary embodiment of a fluid infusion device includes a fluid pump mechanism that cooperates with a fluid cartridge module. The fluid pump mechanism includes a rotor and a stator; the rotor has a reference surface and a rotor cam element having a variable height rising from the reference surface. The stator includes a stator cam element having a stator cam surface, wherein the rotor cam element cooperates with the stator cam element to axially displace the rotor, relative to the stator, as a function of angular position of the rotor. An inlet valve opens and closes as a function of angular and axial position of the rotor relative to the stator, and an outlet valve opens and closes as a function of angular and axial position of the rotor relative to the stator. A biasing element provides a biasing force to urge the rotor toward the stator. A subcutaneous conduit is in fluid communication with the outlet valve, and drive motor is coupled to actuate the rotor of the fluid pump mechanism to pump medication fluid from the fluid cartridge module to the body, via the subcutaneous conduit. A first sensor contact element resides on the rotor and is located at an angular position that follows an upper edge of the rotor cam element. A second sensor contact element resides on the rotor and is located at an angular position that follows the first sensor contact element. A sensing element resides on the stator, and it cooperates with a detection circuit to detect when the sensing element makes contact with the first sensor contact element and the second sensor contact element. The detection circuit monitors characteristics of a detection signal obtained from the sensing element in response to angular position of the rotor to determine an operating condition of the fluid pump mechanism.

An exemplary embodiment of a fluid pump mechanism includes a stator with a stator cam element having a stator cam surface. The fluid pump mechanism also includes a rotor having: an endcap with a rim; a reference surface located inside the endcap; and a rotor cam element located inside the endcap and having a variable height rising from the reference surface. The rotor cam element cooperates with the stator cam element to axially displace the rotor, relative to the stator, as a function of angular position of the rotor. A first sensor contact element resides on the rim of the endcap, and is located at an angular position that follows an upper edge of the rotor cam element. A second sensor contact element resides on the rim of the endcap, and is located at an angular position that follows the first sensor contact element. A biasing element provides a biasing force to urge the rotor toward the stator. The fluid pump mechanism also includes: an inlet valve that opens and closes as a function of angular and axial position of the rotor relative to the stator; an outlet valve that opens and closes as a function of angular and axial position of the rotor relative to the stator; and a sensing element that cooperates with a detection circuit to detect when the sensing element makes contact with the first sensor contact element and the second sensor contact element. The detection circuit monitors characteristics of a detection signal obtained from the sensing element to determine an operating condition of the fluid pump mechanism.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
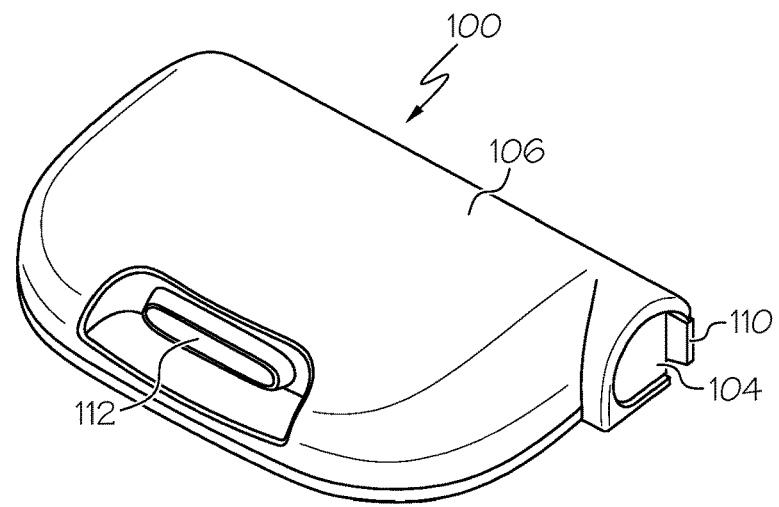
FIG. 1 is a top perspective view of an embodiment of a fluid infusion device implemented as a patch pump device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a patient. The infusion device is used for infusing fluid (such as a medication) into the body of a user. The non-limiting examples described below relate to a medical device used to treat diabetes (more specifically, an insulin infusion device), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump operation, fluid reservoirs, and fluid conduits such as soft cannulas may not be described in detail here.

General Overview And System Architecture

Figure 3:
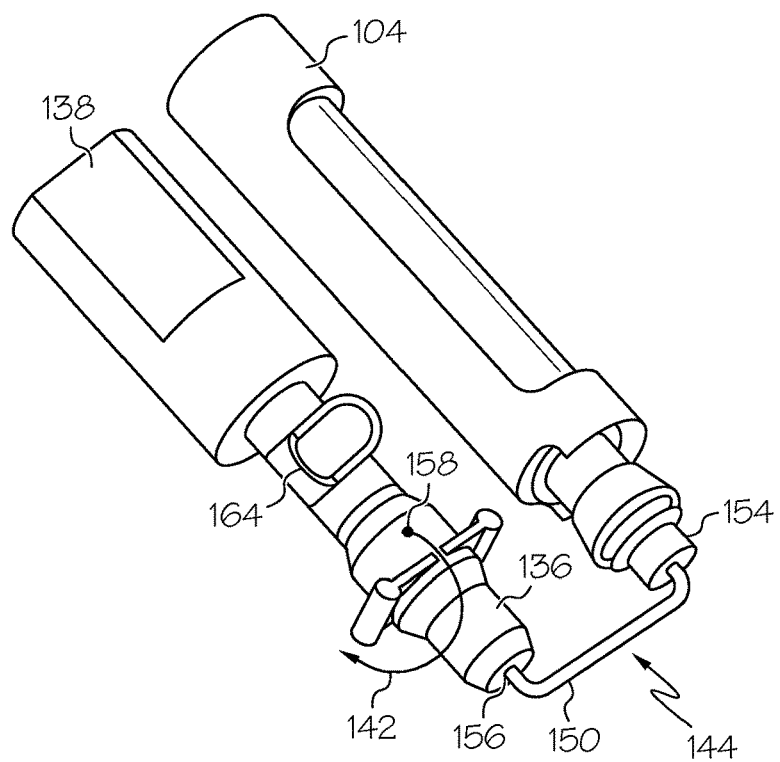
FIG. 3 is a perspective view that shows certain internal components of the fluid infusion device.
Figure 2:
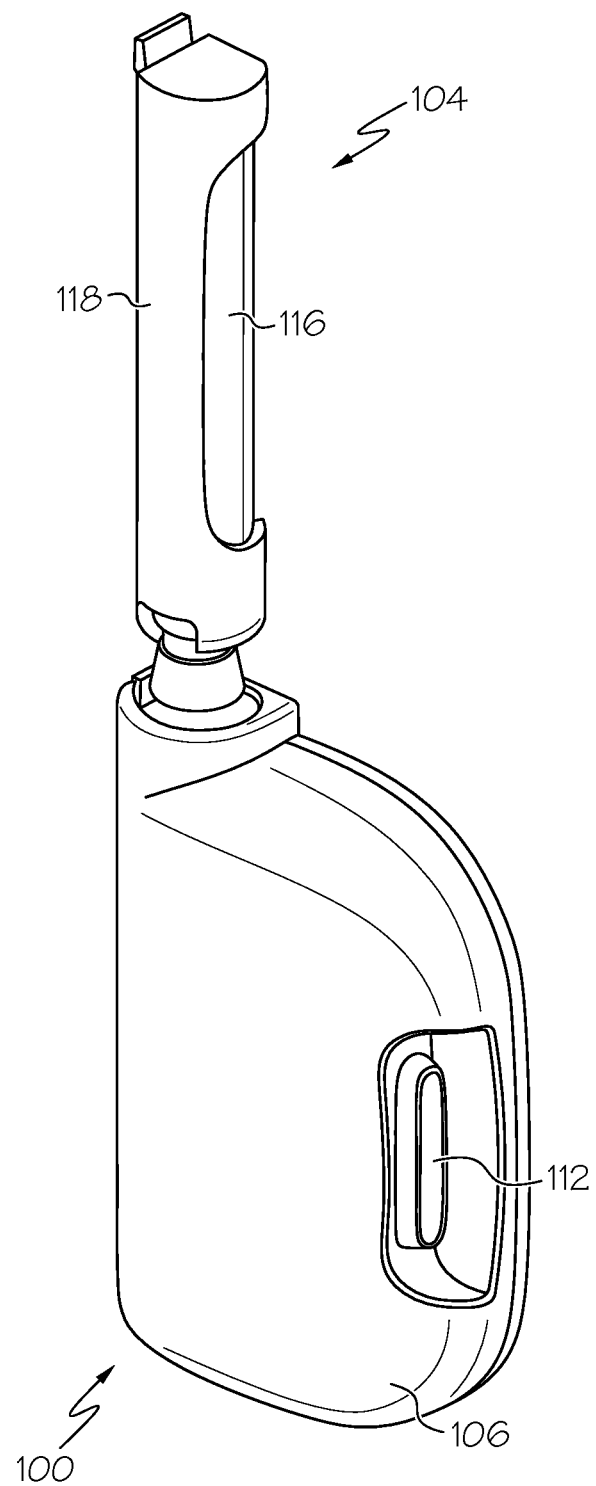
FIG. 2 is a perspective view that depicts the insertion of the removable fluid cartridge module into the fluid infusion device.

FIG. 1 is a top perspective view of an embodiment of a fluid infusion device 100 implemented as a patch pump device, FIG. 2 is a perspective view that depicts the insertion of a removable fluid cartridge module 104 into the fluid infusion device 100, and FIG. 3 is a perspective view that shows certain internal components of the fluid infusion device 100. The removable fluid cartridge module 104 is designed and configured for compatibility with the fluid infusion device 100, and FIG. 1 shows the fluid cartridge module 104 installed and secured within the fluid infusion device 100. The figures depict one possible configuration and form factor of the fluid infusion device 100. It should be appreciated that other designs and configurations can be utilized if so desired, and that the particular design aspects shown in the figures are not intended to limit or otherwise restrict the scope or application of the embodiments described herein.

The fluid infusion device 100 includes a housing 106 that serves as a shell for a variety of internal components. The housing 106 is suitably configured to receive, secure, and release the removable fluid cartridge module 104. In this regard, the fluid cartridge module 104 can be received in a suitably shaped, sized, and configured cavity that is designed in accordance with certain physical characteristics of the fluid cartridge module 104. For example, the housing 106 can include structural features that mate with or otherwise engage structural features of the fluid cartridge module 104. The illustrated embodiment of the removable fluid cartridge module 104 includes a retention mechanism 110 that secures the fluid cartridge module 104 in the properly installed and seated position within the fluid infusion device 100. The retention mechanism 110 locks the fluid cartridge module 104 in place within the cavity 108 to maintain the necessary physical and fluid connections between the fluid cartridge module 104 and the fluid infusion device 100. The retention mechanism 110 can be physically manipulated to release the fluid cartridge module 104 from the housing 106 as needed (e.g., to replace one cartridge module with a different cartridge module, to remove the cartridge module when replacing an old fluid infusion device with a new fluid infusion device, or the like). In practice, the retention mechanism 110 can be realized as a latching feature, a locking feature, a tab, or the like.

The fluid infusion device 100 includes at least one user interface feature, which can be actuated by the patient as needed. The illustrated embodiment of the fluid infusion device 100 includes a button 112 that is physically actuated. The button 112 can be a multipurpose user interface if so desired to make it easier for the user to operate the fluid infusion device 100. In this regard, the button 112 can be used in connection with one or more of the following functions, without limitation: waking up the processor and/or electronics of the fluid infusion device 100; triggering an insertion mechanism for actuating a transcutaneous conduit assembly (e.g., inserting a cannula into the subcutaneous space, or similar region of the patient); configuring one or more settings of the fluid infusion device 100; initiating delivery of medication fluid; initiating a fluid priming operation; disabling alerts or alarms generated by the fluid infusion device 100; and the like. In lieu of the button 112, the fluid infusion device 100 can employ a slider mechanism, a pin, a lever, or the like.

The fluid infusion device 100 includes an adhesive element or adhesive material (hidden from view in FIG. 1 and FIG. 2) that can be used to affix the housing 106 to the body of the patient. The adhesive element can be located on the bottom surface of the housing 106 such that the housing 106 can be temporarily adhered to the skin of the patient. The adhesive element may be, for example, a piece of double sided adhesive tape that is cut into the desired shape and size. The fluid infusion device 100 is manufactured with an adhesive liner overlying the adhesive element; the adhesive liner is peeled away to expose the sticky surface of the adhesive element 114. The adhesive element is chosen to be strong enough to maintain the fluid infusion device 100 in place for the desired period of time (which is typically between one to seven days) and strong enough to withstand typical use cases (e.g., showering, rainy days, physical exercise, etc.), while also being easy to remove without discomfort.

Setup and operation of the fluid infusion device 100 is simple and straightforward for the patient. In this regard, the particular procedure for setup and initiation may vary from one embodiment to another, depending on the specific configuration, design, form factor, and/or optional settings of the fluid infusion device 100. In accordance with one high level method of operation, the fluid infusion device 100 is deployed in the following manner: (1) insert the fluid cartridge module 104 into the housing 106; (2) remove the adhesive liner; (3) affix the housing 106 to the body; and (4) insert the fluid delivery cannula into the body by pressing a button, pulling a tab, removing a safety pin, or otherwise activating an insertion mechanism to release a preloaded spring or equivalent actuation component. Thereafter, the fluid infusion device can be prepared for the delivery of the medication fluid as needed.

In accordance with an alternative method of operation, the fluid cartridge module 104 is installed after the housing 106 is affixed to the body. In accordance with this option, the action of installing the fluid cartridge module 104 into the housing 106 engages or moves a mechanical, electrical, magnetic, or other type of interface, which in turn releases a preloaded spring or equivalent actuation component to insert the fluid delivery cannula into the body. Once the spring is released upon the first cartridge insertion, the fluid infusion device 100 is put into a different state such that subsequent installations of a fluid cartridge module will not trigger the insertion mechanism again.

In certain embodiments, the fluid infusion device 100 is realized as a single-piece disposable component that is designed for continuous use over a designated period of time, such as three days. Although not always required, the fluid infusion device 100 can be designed to accommodate prefilled fluid cartridge modules 104, which may be provided by third party manufacturers in "off the shelf" volumes (e.g., 1.0 mL, 1.5 mL, 2.0 mL, or 3.0 mL of medication fluid). It should be appreciated that the fluid infusion device 100 can also be suitably configured and designed to accommodate user-filled fluid cartridge modules 104. Referring to FIG. 2, each removable fluid cartridge module 104 can be realized as a single-use disposable reservoir that is not designed or intended to be refilled. The illustrated embodiment of the fluid reservoir cartridge module 104 includes a glass or plastic reservoir 116 that is held in a carrier 118 or housing to facilitate insertion and removal of the reservoir 116.

As mentioned above, the housing 106 of the fluid infusion device 100 receives the removable fluid cartridge module 104 containing the desired medication fluid. The housing 106 also serves to contain the variety of components and elements that cooperate to support the functionality of the fluid infusion device 100. These internal components and elements can include, without limitation: a printed circuit board; a vibration motor or other haptic feedback element; a battery or other energy source; a fluid pump mechanism; a drive motor coupled to actuate the fluid pump mechanism (or other devices, components, or means to actuate the fluid pump mechanism, such as a solenoid, a nickel-titanium memory wire, or the like); an insertion mechanism for actuating a transcutaneous conduit assembly; sensors that interact with the drive motor, the fluid pump mechanism, and/or the button 112; an outlet fluid conduit; and an inlet conduit assembly. Of course, an embodiment of the fluid infusion device 100 may include additional features, components, devices, and elements that are not depicted in the figures or described in detail here.

The printed circuit board includes various electronic components, devices, and connections that cooperate to support the functions of the fluid infusion device 100. These components are enclosed within the housing 106 for protection, water resistance, and the like. The printed circuit board 130 may include or cooperate with any of the following, without limitation: switches; adjustment or trim elements such as a potentiometer; a processor device; memory; or the like. The vibration motor can be used to generate confirmation or alert signals as needed. Alternatively or additionally, the fluid infusion device 100 can include an audio transducer, an indicator light, a display element, or other components to provide feedback to the user. The battery can be a single use element that can be discarded with the fluid infusion device. The battery provides the required voltage and current to operate the fluid infusion device 100.

FIG. 3 depicts an embodiment of the fluid pump mechanism 136, which is fluidly coupled to the removable fluid cartridge module 104 during operation of the fluid infusion device 100. The fluid pump mechanism 136 can be realized as a rotationally actuated micro pump that delivers a calibrated amount of medication fluid with each delivery cycle. In this regard, the fluid pump mechanism 136 includes a stator and a rotor; the rotor is actuated in a controlled manner by a drive motor 138. As described in more detail below, the fluid pump mechanism 136 functions by translating rotational movement of the rotor into axial displacement of the rotor relative to the stator. In turn, the translational movement results in the opening and closing of a series of valves that are internal to the fluid pump mechanism 136 for purposes of drawing in the medication fluid from the fluid cartridge module 104. A biasing force (e.g., a spring force) forces the rotor toward the stator, which expels the fluid through the outlet of the fluid pump mechanism 136. In certain embodiments, the fluid pump mechanism 136 leverages the pump technology offered by Sensile Medical, although other types of pump technologies can also be utilized.

In accordance with certain embodiments, the biasing force that urges the rotor into the stator is provided by a molded plastic part that serves as both the spring element and a coupling component (to mechanically couple the drive motor 138 to the rotor). This spring coupler 164 is shown in FIG. 3. The spring coupler 164 eliminates the need for a separate coupling element, which reduces parts count, reduces product cost, and simplifies manufacturing and assembly of the fluid infusion device 100. The spring coupler 164 can be a physically distinct component that is mechanically attached between the drive motor 138 and the rotor of the fluid pump mechanism 136. In alternative embodiments, the spring coupler 164 can be integrally fabricated with the rotor.

The drive motor 138 can be a direct current (DC) motor, a brushless DC motor, a stepper motor, or the like. It should be appreciated that other drive methodologies could be used instead of the drive motor 138, such as a nickel titanium memory wire and a ratcheting mechanism to create rotational motion to drive the fluid pump mechanism 136.

Thus, a full rotation of the rotor results in the delivery of a known amount of medication fluid. After the fluid flow path of the fluid infusion device 100 has been primed, each rotation of the rotor draws a measured volume of medication fluid from the fluid cartridge module 104 and expels the same amount of medication fluid from the cannula situated in the patient.

With continued reference to FIG. 3, an inlet conduit assembly 144 includes structure that is compatible with the removable fluid cartridge module 104. For example, the inlet conduit assembly 144 includes a fluid conduit 150 that terminates at a hollow reservoir needle (hidden from view because it extends into the fluid cartridge module 104). The hollow reservoir needle enters the reservoir of the fluid cartridge module 104 (via a septum) when the fluid cartridge module 104 is installed in the fluid infusion device 100. The fluid infusion device 100 also includes a sealing element 154, which may be coupled to the inlet conduit assembly 144 (alternatively, the sealing element 154 can be an integral part of the inlet conduit assembly 144). The sealing element 154 can be a compressible and resilient component that creates a fluid seal for the inlet conduit assembly 144 when the fluid cartridge module 104 is removed from the housing 106 of the fluid infusion device 100. More specifically, the sealing element 154 is compressed when the fluid cartridge module 104 is installed, thus exposing the hollow reservoir needle. The sealing element 154 extends to cover the end of the hollow reservoir needle when the fluid cartridge module 104 is removed, which inhibits the ingress of contaminants, fluid, and air into the inlet conduit assembly 144, and which inhibits leakage of medication fluid from the fluid flow path of the fluid infusion device 100.

Moreover, the inlet conduit assembly 144 is in fluid communication with a fluid inlet 156 of the fluid pump mechanism 136. The fluid inlet 156 accommodates and receives an end of the fluid conduit 150, as shown in FIG. 3. This arrangement allows the fluid pump mechanism 136 to draw the medication fluid in from the fluid cartridge module 104, via the inlet conduit assembly 144. The fluid pump mechanism 136 expels the medication fluid from a fluid outlet 158, which is in fluid communication with the outlet fluid conduit 142. FIG. 3 depicts only a portion of the outlet fluid conduit 142. In certain embodiments, the outlet fluid conduit 142 may be realized as part of a transcutaneous conduit assembly of the fluid infusion device 100, wherein the transcutaneous conduit assembly also includes a subcutaneous conduit (e.g., a soft cannula) that is inserted and positioned within the body of the patient.

The transcutaneous conduit assembly is in fluid communication with the fluid outlet 158 of the fluid pump mechanism 136. More specifically, in accordance with the illustrated embodiment, the outlet fluid conduit 142 is implemented as a flexible hollow needle having its proximal end fluidly coupled to the fluid outlet 158. The distal end of the flexible hollow needle is sharp to accommodate the insertion of the subcutaneous conduit into the body of the patient during an insertion operation. The distal end of the flexible hollow needle is not shown in FIG. 3. The proximal end of the subcutaneous conduit is fluidly coupled to the flexible hollow needle such that at least a portion of the needle is initially inside the subcutaneous conduit (i.e., the subcutaneous conduit is carried by the flexible hollow needle before and during an insertion operation). Accordingly, the subcutaneous conduit is in fluid communication with the fluid pump mechanism 136 such that the medication fluid can be delivered to the body of the patient via the outlet fluid conduit 142 and the subcutaneous conduit.

The fluid infusion device 100 includes a flow path that accommodates the delivery of the medication fluid from the fluid cartridge module 104 to a subcutaneous site in the body of the patient. A first fluid flow path is at least partially defined by the inlet conduit assembly 144, which resides between the fluid cartridge module 104 and the fluid pump mechanism 136. The first fluid flow path may be considered to be the inlet flow path of the fluid pump mechanism 136. A second flow path (which may be considered to be the outlet flow path of the fluid pump mechanism 136) is defined by the outlet fluid conduit 142 and the subcutaneous conduit. In this regard, the second flow path terminates at the distal end of the subcutaneous conduit. The overall flow path of the fluid infusion device 100, therefore, includes the first fluid flow path, the fluid pump mechanism 136, and the second fluid flow path. It should be appreciated that the fluid flow path through the fluid infusion device 100 can be established using any number of rigid needles (bent or straight), soft tubing, flexible steel tubing, or the like. The particular embodiment described herein is merely one possible arrangement.

Figure 4:
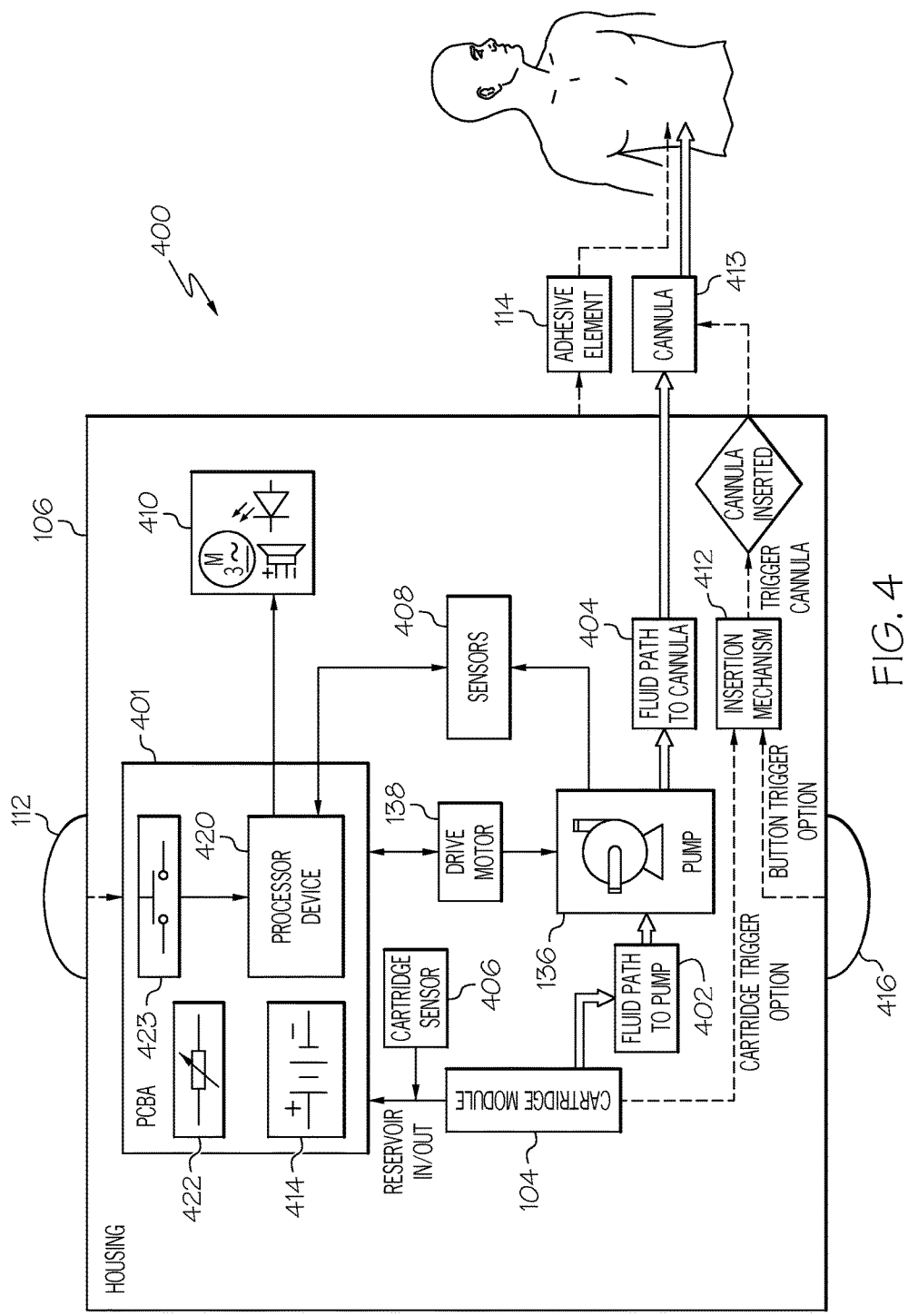
FIG. 4 is a block diagram representation of the system architecture of a fluid infusion device according to certain embodiments.

FIG. 4 is a block diagram that depicts an exemplary embodiment of a system architecture 400 suitable for use with the fluid infusion device 100. FIG. 4 depicts the housing 106 of the fluid infusion device 100, along with various components, elements, and devices that are housed by, enclosed within, or attached to the housing 106. In FIG. 4, solid arrows represent electrical signal paths, dashed arrows represent mechanical interaction or cooperation between elements, and doubled arrows represent fluid flow paths. It should be appreciated that an embodiment of the system architecture 400 can include additional elements, components, and features that may provide conventional functionality that need not be described herein. Moreover, an embodiment of the system architecture 400 can include alternative elements, components, and features if so desired, as long as the intended and described functionality remains in place.

The illustrated embodiment of the system architecture 400 generally includes, without limitation: a printed circuit board 401; the removable fluid cartridge module 104; the fluid pump mechanism 136; the drive motor 138; a fluid flow path 402; a fluid flow path 404; a cartridge sensor 406; one or more status sensors 408; one or more alerting devices 410; an insertion mechanism 412; and a subcutaneous conduit 413. FIG. 4 includes a number of items that were previously described, and those items will not be redundantly described in detail here.

The printed circuit board 401 may include or carry at least some of the electronics of the fluid infusion device 100, e.g., any number of discrete or integrated devices, components, electrical conductors or connectors, and the like. For example, the following items may be found on the printed circuit board 401, without limitation: a battery 414; a processor device 420; a basal rate adjustment component 422; and a switch 423. The printed circuit board 401 (or the items carried by the printed circuit board 401) can be electrically coupled to other elements of the system architecture 400 as needed to support the operation of the fluid infusion device 100. For example, the printed circuit board 401 can be electrically coupled to at least the following, without limitation: the fluid cartridge module 104; the fluid pump mechanism 136; the drive motor 138; the cartridge sensor 406; the status sensors 408; and the alerting devices 410. It should be appreciated that electrical connections to the printed circuit board 401 can be direct or indirect if so desired. Moreover, one or more components on the printed circuit board 401 may support wireless data communication in some embodiments.

The flow path 402 fluidly couples the fluid cartridge module 104 to the inlet of the fluid pump mechanism 136, and the flow path 404 fluidly couples the outlet of the fluid pump mechanism 136 to the subcutaneous conduit 413. The subcutaneous conduit 413 is fluidly coupled to the body of the patient. The drive motor 138 is electrically and mechanically coupled to the fluid pump mechanism 136 to control the operation of the fluid pump mechanism 136. Thus, the drive motor 138 can be turned on and off as needed by the processor device 420 to control the position of the rotor of the fluid pump mechanism 136.

The status sensors 408 can be electrically coupled to the fluid pump mechanism 136 and to the printed circuit board 401 to monitor certain operating conditions, parameters, or characteristics of the fluid pump mechanism 136 and/or other components of the fluid infusion device 100. For example, the information provided by the status sensors 408 can be processed or otherwise utilized to determine the revolution count of the fluid pump mechanism 136, to determine the resting position of the fluid pump mechanism 136, to detect a downstream occlusion in the fluid delivery path, to detect when the reservoir of the fluid cartridge module 104 is empty, or the like.

The alerting devices 410 can be electrically coupled to the printed circuit board 401 for purposes of controlled activation. In this regard, activation of the alerting devices 410 can be controlled by the processor device 420 as needed. In certain embodiments, user manipulation of the button 112 results in actuation of the switch 423, which in turn disables alerts or alarms generated by the alerting devices 410.

The dashed arrow labeled "Cartridge Trigger Option" in FIG. 4 represents mechanical interaction (and/or electrical, magnetic, inductive, optical, capacitive, or other detection methodology) between the fluid cartridge module 104 and the insertion mechanism 412. In this regard, installation of the fluid cartridge module 104 into the housing 106 can be detected to trigger the insertion mechanism 412. If the subcutaneous conduit 413 is not yet inserted in the body of the patient (i.e., the spring mechanism has not been actuated), then the insertion mechanism 412 fires to position the subcutaneous conduit 413 into a subcutaneous location. In alternative embodiments, a devoted insertion button 416 is used to fire the insertion mechanism 412. Accordingly, the dashed arrow labeled "Button Trigger Option" in FIG. 4 represents mechanical interaction (and/or some other detection methodology) between the insertion button 416 and the insertion mechanism 412. In accordance with this option, the insertion mechanism 412 is triggered by physical manipulation of the insertion button 416, and the subcutaneous conduit 413 is installed (unless the insertion mechanism 412 has already been fired).

The processor device 420 can be realized in any form factor. In certain embodiments, the processor device 420 is realized as an application specific integrated circuit (ASIC) that is mounted to the printed circuit board 401. The ASIC can also include a suitable amount of memory that is needed to support the operations and functions of the fluid infusion device. In this regard, techniques, methods, and processes may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or computer-readable instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like. The software that performs the described functionality may reside and execute at, for example, an ASIC.

More specifically, the processor device 420 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. In particular, the processor device 420 may be realized as a microprocessor, a controller, a microcontroller, or a state machine. Moreover, the processor device 420 may be implemented as a combination of computing devices, e.g., a combination of a digital signal processor and a microprocessor, a plurality of microprocessors, one or more microprocessors in conjunction with a digital signal processor core, or any other such configuration.

The processor device 420 includes or cooperates with memory, which can be realized as RAM memory, flash memory, EPROM memory, EEPROM memory, registers, or any other form of storage medium known in the art. The memory can be implemented such that the processor device 420 can read information from, and write information to, the memory. In the alternative, the memory may be integral to the processor device 420. As an example, the processor device 420 and the memory may reside in a suitably designed ASIC.

In the context of the particular embodiments described in more detail below, the processor device 420 can implement, cooperate with, or otherwise support the operation of a detection circuit (and applicable processing logic) that functions to detect downstream occlusions in a fluid flow path, upstream occlusions in a fluid flow path, end of reservoir conditions in a fluid infusion device, and/or other detectable operating conditions. To this end, the processor device 420 can execute suitably written computer instructions that cause the processor device 420 to perform the various detection tasks, operations, and method steps described below in the context of the different detection methodologies.

The simple user interface can include a physical button 112, a capacitive button, a thin film force sensitive resistor as a button (using deformation of a specific part of the housing 106 as a button), etc. The button 112 can be activated to deliver a bolus, to remove the device from an inactive shelf mode, to provide a self-check, to respond to alerts or alarms, and the like. The system architecture 400 may include an optional insertion button 416 that can be activated to release the conduit insertion mechanism 412.

One implementation is to have a single software-set basal rate and bolus button value. For example, one SKU can be used for a fluid infusion device having a basal setting of 2 Units/hr, wherein each press of the button 112 results in the delivery of two Units of bolus therapy. A different SKU can be used for a fluid infusion device having a basal setting of 1 U/hr, wherein each press of the button 112 results in the delivery of one Unit of bolus therapy. In practice, the bolus value can be set based on research of total insulin consumption so as to simplify the operation of the device. For example, if a patient uses 100 U/day of basal therapy, they likely need more bolus therapy and, therefore, a 5.0 Unit bolus deliver for each button press might be suitable. On the other hand, if a patient uses 20 U/day of basal therapy, they likely need less bolus therapy and, therefore, the bolus button for the device might be configured to deliver only 1.0 Unit per button press.

Regarding the bolus delivery function, each time the patient presses the button 112, the fluid infusion device 100 delivers the programmed bolus value and waits for the next button press. Thus, if the fluid infusion device 100 has a preset bolus value of 5.0 Units and the patient needs 15.0 Units, then the patient presses the button 112 one time to deliver the first 5.0 Units, presses the button 112 a second time to deliver the next 5.0 Units, and presses the button 112 a third and final time for the last 5.0 Units.

The fluid infusion device 100 also allows for multiple button presses, provides confirmation (vibration, auditory, indicator lights), and then delivers the entire amount. For example, the fluid infusion device 100 may process three back-to-back button presses, recognize a total of three presses, provide user feedback, wait for confirmation, and then deliver a total of 15.0 Units.

Patient-specific programming can be achieved through a physician programmer via a wired or wireless communication session. For example, an infrared window can be provided in the housing of the fluid infusion device to accommodate wireless adjustments or programming. Other methods to adjust the basal rate utilize a dial, a knob, or other adjustment component that the physician or patient can manipulate. The adjustment component can be connected to the printed circuit board 401 and, specifically, to the processor device 420 for purposes of changing the timing and/or other characteristics of the fluid pump mechanism 136. FIG. 4 depicts a basal rate adjustment component 422 that is intended to represent the various methodologies and components that serve to adjust the programmed basal rate of the fluid infusion device 100. One simple and low cost way to visualize and confirm the adjustment involves the use of a clear window on the housing of the fluid infusion device and a colored dial with markings corresponding to the adjustment setting.

The system architecture 400 may include or cooperate with any combination of alerting devices 410, including, without limitation: a vibration motor; a piezoelectric audio transducer; one or more indicator lights (e.g., light emitting diodes or other lamp components); a speaker protected by a hydrophobic membrane; and the like.

The drive motor 138 can be electrically coupled to the printed circuit board 401 with a connector and wires, plated traces on the housing 106, or the like. The drive motor 138 can be coupled to the fluid pump mechanism 136 using a coupler and a spring (not shown). Alternatively, certain embodiments can utilize the one-piece spring coupler 164 described above with reference to FIG. 3.

The status sensors 408 can be used to monitor the health and operation of the fluid pump mechanism 136. For example, the status sensors 408 can be used to check the winding resistance of the drive motor 138. The system architecture 400 can also be configured to detect certain fault conditions such as fluid path occlusion, an end of reservoir condition, the Units remaining in the reservoir, and the like. The status sensors 408 can be utilized to check for these and other operating conditions if so desired.

In some embodiments, occlusion can be detected by using a Hall sensor to determine the axial position rate of change of the rotor of the fluid pump mechanism 136. The sensor system can include a magnet positioned on the rotor, and a Hall sensor on the printed circuit board 401. Pumping air rather than fluid, versus not pumping due to an occlusion, will provide a different linear rate of change of the rotor and, therefore, can be correlated to the pumping condition. This methodology will require knowledge of the rotational state of the rotor, i.e., when the rotor has completed one full turn. This can be achieved with a magnetic encoder, an optical encoder, a physical feature on the pump rotor that contacts a switch every time a rotation is complete, or the like. The switch can be a physical, inductive, capacitive, photo-interrupt, or other type of switch. Multiple optical encoders can be used in place of a Hall sensor, one to detect angular position of the rotor, and one to detect linear position. Similarly, magnetic or other encoders can be used.

An end of reservoir condition can be detected using the same methodology described above for occlusion detection, or it can be detected using an optical sensor to monitor the position of the plunger or piston of the fluid cartridge module 104. Other techniques and technologies can also be utilized to determine when the fluid cartridge module 104 needs to be replaced. Various techniques and methodologies for detecting downstream occlusions and upstream occlusions (e.g., "end of reservoir" conditions) are described in a more fulsome manner below.

The amount of medication fluid remaining can be determined using an optical sensor that detects the location of the plunger near the end of the reservoir volume. A countdown value can be calculated to provide an estimate of the number of Units remaining in the reservoir. Alternatively, the amount of fluid remaining can be determined magnetically by providing a magnet on the plunger of the reservoir. A magnetic sensor in the housing 106 can be used to detect the magnet. As yet another option, inductive or capacitive detection methodologies can be leveraged to determine the amount of medication fluid remaining in the fluid cartridge module 104. The detected position is calibrated to correspond to a specific volume of fluid remaining in the reservoir.

Prefilled fluid cartridge modules 104 can be provided in a housing that facilitates insertion into the housing 106 and removal from the housing 106, as described above. The fluid cartridge modules 104 can be designed to provide a convenient and easy to handle form factor. In certain embodiments, installation of the fluid cartridge module 104 activates the cannula insertion mechanism 412, which eliminates the need for an extra patient step and system component devoted to this function. In FIG. 4, the arrow labeled "Cartridge Trigger Option" represents this functionality.

Figure 18:
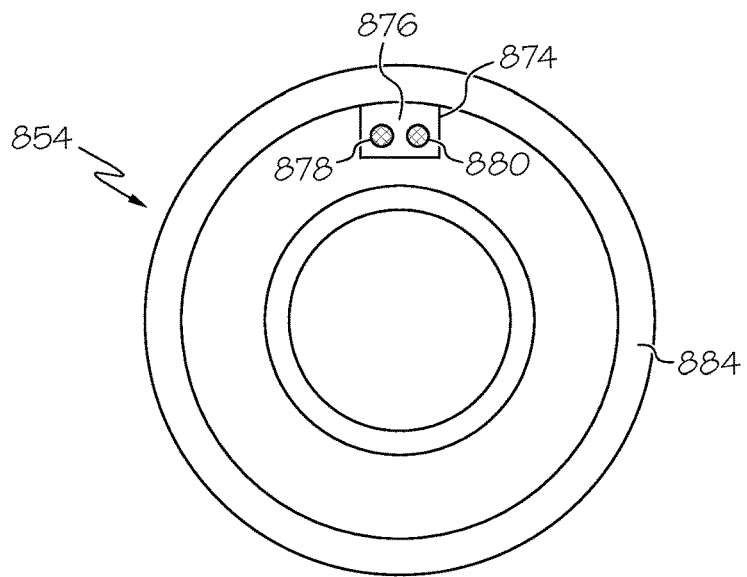
FIG. 18 is an end view of an exemplary embodiment of a stator of a fluid pump mechanism.

The fluid cartridge module 104 may also be configured to communicate to the processor device 420 (or initiate such communication) whether or not it has been installed. The arrow labeled "Reservoir In/Out" in FIG. 4 represents this communication. Thus, the act of inserting the fluid cartridge module 104 into the housing 106 can be electronically detected to take appropriate action. Conversely, if the fluid cartridge module 104 is removed, the fluid infusion device 100 can suspend basal and bolus therapy. When the fluid cartridge module 104 is reinstalled, the therapy can be resumed. The manner in which the fluid cartridge module 104 is detected may vary from one embodiment to another. In certain embodiments, a physical feature on the fluid cartridge module 104 interacts with a feature or a mechanical component of the fluid infusion device 100 that, in turn, triggers a switch on the printed circuit board 401. Alternatively (or additionally), installation of the fluid cartridge module 104 can be achieved by creating a short circuit across electrical contacts when the fluid cartridge module 104 is installed. For example, a metal cap on the fluid cartridge module 104 can serve as the electrical conductor that creates the short circuit. Alternatively, the exterior of the fluid cartridge module 104 can include printed plating or a conductive trace on specific locations that create a short across contacts of the fluid infusion device 100 when the fluid cartridge module 104 is installed. As yet another example, installation of the fluid cartridge module 104 can be detected by physical contact, capacitive sensing, inductive sensing, optical sensing, acoustic sensing, magnetic sensing, infrared sensing, RFID technology, or the like. The cartridge sensor 406 depicted in FIG. 18 is intended to represent these and other possible methodologies, components, and features that detect when the fluid cartridge module 104 is seated/installed, and when the fluid cartridge module 104 is unseated/uninstalled.

Fluid Pump Mechanism

FIGS. 5-8 are diagrams that depict a fluid pump mechanism 500 in various stages during one pump cycle. FIGS. 5-8 schematically depict the fluid pump mechanism 500 in a simplified way for ease of understanding. An embodiment of the fluid pump mechanism 500 can be configured as needed to suit the requirements of the particular application. The fluid pump mechanism 500 generally includes, without limitation: a rotor 502; a stator 504; and a biasing element 506. The rotor 502 includes an axial extension section 508 that is at least partially received within the stator 504. For this example, the rotor 502 is driven such that it rotates relative to the stator 504. In alternative implementations, the stator 504 could be rotated relative to the rotor 502, or both the rotor 502 and the stator 504 could be rotated relative to each other. The biasing element 506 (which may be realized as a spring, such as the spring coupler 164 shown in FIG. 3) provides a biasing force that urges the rotor 502 toward the stator 504.

The fluid pump mechanism 500 includes a fluid inlet 510 and a fluid outlet 512. Although not always required, the fluid inlet 510 is located at the end of the stator 504, and the fluid outlet 512 is located on the side of the stator 504 (which is consistent with the embodiment shown in FIG. 3). The fluid inlet 510 can be in communication with the reservoir of the fluid cartridge module 104, and the fluid outlet 512 can be in communication with the fluid flow path that leads to the body of the patient. Alternative arrangements for the fluid inlet 510 and the fluid outlet 512 are also contemplated by this disclosure. Internal fluid pathways, sealing structures, and valve structures are not depicted in FIGS. 5-8 for the sake of clarity and simplicity.

Figure 5:
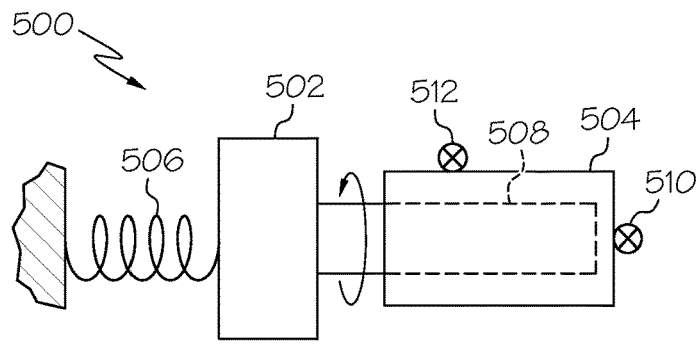
FIGS. 5-8 are diagrams that depict a fluid pump mechanism in various stages during one pump cycle.
Figure 6:
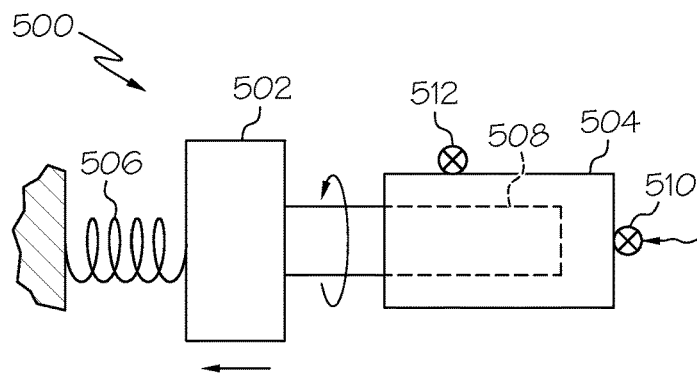
Figure 7:
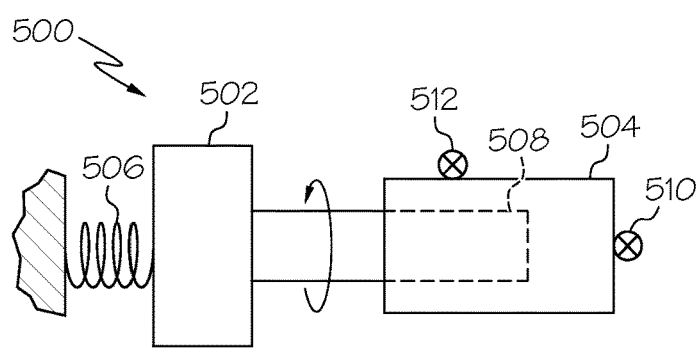
Figure 8:
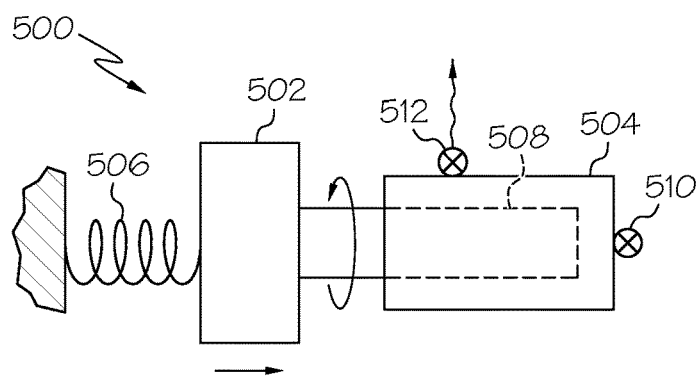

FIGS. 5-8 depict different states of the fluid pump mechanism 500 during one fluid delivery cycle, which corresponds to one revolution of the rotor 502. FIG. 5 shows the fluid pump mechanism 500 in an initial state where the internal valve and sealing structures effectively seal the fluid inlet 510 and the fluid outlet 512. In this initial state, the rotor 502 is fully seated within the stator 504, and the axial displacement of the rotor 502 relative to the stator 504 is considered to be zero. FIG. 6 shows the fluid pump mechanism 500 in a fluid intake state. In this state, the fluid inlet 510 is free to draw the medication fluid into the fluid pump mechanism 500, but the fluid outlet 512 remains sealed. Fluid is drawn into the fluid inlet 510 as the axial displacement of the rotor 502 relative to the stator 504 increases. Continued rotation of the rotor 502 eventually causes the fluid pump mechanism 500 to reach the state shown in FIG. 7. In this state, the fluid inlet 510 and the fluid outlet 512 are sealed, and the fluid is ready to be expelled from the fluid pump mechanism 500. Moreover, the axial displacement of the rotor 502 relative to the stator 504 is maximized while in the state shown in FIG. 7. Further rotation of the rotor 502 enables the biasing element 506 to force the rotor 502 back into the stator 504, which in turn expels the fluid from the fluid outlet 512. In the state depicted in FIG. 8, the fluid outlet 512 is free to expel the fluid from the fluid pump mechanism 500, but the fluid inlet 510 remains sealed to inhibit backflow. The biasing element 506 urges the rotor 502 into its fully seated position, and further rotation of the rotor 502 eventually returns the fluid pump mechanism 500 to the initial state shown in FIG. 5. Under normal and expected operating conditions, one complete rotation of the rotor 502 corresponds to one pumping cycle (i.e., one fluid delivery cycle) having a defined fluid intake period and a defined fluid expulsion period. During one pumping cycle, medication fluid is drawn from the fluid cartridge module 104 and, thereafter, medication fluid is expelled from the fluid outlet 512 for delivery to the patient.

Figure 9:
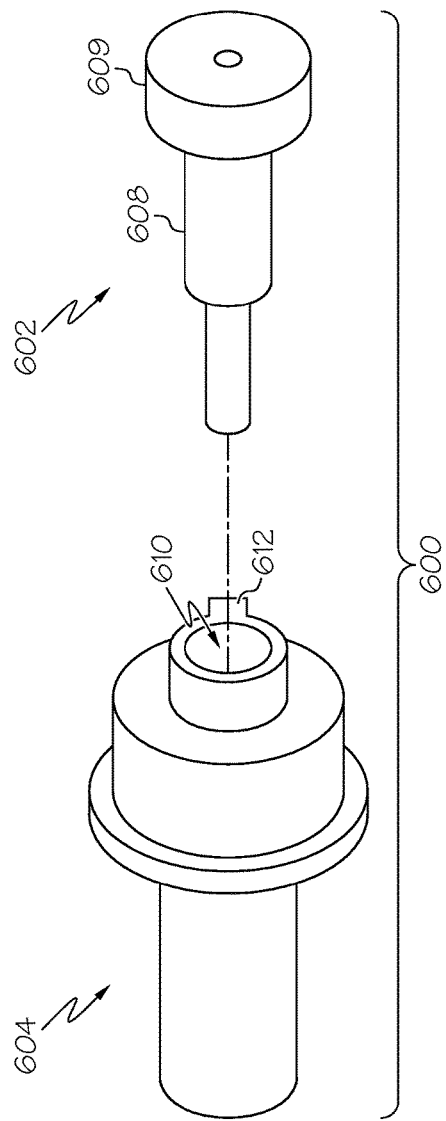
FIG. 9 is an exploded perspective view of a stator and a rotor of an exemplary embodiment of a fluid pump mechanism.

FIG. 9 is an exploded perspective view of an exemplary embodiment of a fluid pump mechanism 600 having a rotor 602 and a stator 604. The fluid pump mechanism 600 operates in the same manner summarized above with reference to FIGS. 5-8. An embodiment of the fluid pump mechanism 136, 500, 600 can be designed and configured in accordance with the pump described in United States Patent Application Publication number US 2009/0123309 (the content of which is incorporated by reference herein). For clarity and ease of understanding, the following description only refers to the fluid pump mechanism 600.

As mentioned above with reference to FIGS. 5-8, the rotor 602 has an axial extension section 608 that is shaped and sized for insertion into a rotor chamber 610 of the stator 604. The axial extension section 608 protrudes from the endcap 609 of the rotor 602, and at least a portion of the axial extension section 608 fits inside the rotor chamber 610. The axial extension section 608 can rotate and move in the axial direction relative to the stator 604. The fluid pump mechanism 600 includes a first valve and a second valve (not shown in FIG. 9) that open and close as a function of the angular and axial position of the rotor 602 relative to the stator 604. The valves are realized using a suitably configured sealing structure and/or sealing elements that cooperate with fluid supply channels formed in the axial extension section 608. The sealing structure and/or sealing elements are positioned inside the stator 604.

Rotation of the rotor 602 also results in axial displacement of the rotor 602 relative to the stator 604. The rotation-based axial displacement is provided by cooperating cam elements located on the rotor 602 and the stator 604. FIG. 9 depicts a portion of the stator cam element 612; the rotor cam element, however, is hidden from view in FIG. 9. When the rotor 602 rotates relative to the stator 604, the angular and axial movement of the axial extension section 608 results in the opening and closing of the two valves. During a complete rotational cycle of the fluid pump mechanism 600, the axial displacement of the rotor 602 relative to the stator 604 generates a pumping action inside the rotor chamber 610 (as described above with reference to FIGS. 5-8). In this regard, the rotor chamber 610 defined in the stator 604 may include or serve as the fluid chamber of the fluid pump mechanism 600.

Figure 11:
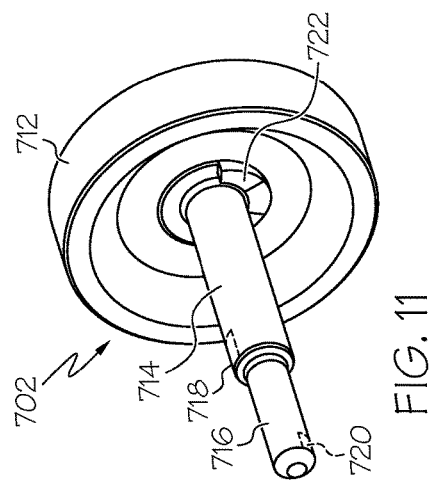
FIG. 11 is a perspective view of an exemplary embodiment of a rotor of a fluid pump mechanism.
Figure 10:
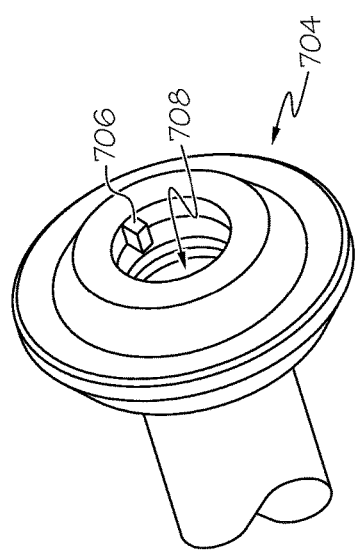
FIG. 10 is a perspective view of an exemplary embodiment of a stator of a fluid pump mechanism.

FIG. 10 is a perspective view of an exemplary embodiment of a stator 704 of a fluid pump mechanism, and FIG. 11 is a perspective view of an exemplary embodiment of a compatible rotor 702. It should be appreciated that the fluid infusion device that hosts the rotor 702 and the stator 704 will include appropriate structure, components, features, and/or elements that support and hold the rotor 702 and the stator 704 in the desired positions, and that accommodate axial and rotational movement of the rotor 702 relative to the stator 704. For the sake of clarity and simplicity, such cooperating structure, components, features, and/or elements are not depicted in FIG. 10 or FIG. 11.

Although the stator 704 has a different configuration than the stator 604 depicted in FIG. 9, the operating concepts and functionality are identical for purposes of this description. In this regard, the stator 704 includes a stator cam element 706 and a rotor opening 708 (as described above). The rotor 702 generally includes, without limitation: an endcap 712; a proximal axial extension 714; a distal axial extension 716; a first fluid supply channel 718 formed in the proximal axial extension 714; a second fluid supply channel 720 formed in the distal axial extension 716; and a rotor cam element 722.

The fluid supply channels 718, 720 are realized as thin slits that extend from the outer surfaces of the axial extensions 714, 716. Sealing elements located inside the stator 704 cooperate with the fluid supply channels 718, 720 to act as valves that open and close as a function of the angular and axial position of the rotor 702 relative to the stator 704. This enables pumping of medication fluid supplied from the fluid cartridge module 104 (see FIG. 3 and FIG. 4) due to a changes in volume in the rotor opening 708 caused by the axial displacement of the rotor 702.

The endcap 712 can be suitably configured to mate with or otherwise cooperate with the drive motor 138, such that the angular position of the rotor 702 can be controlled as needed. Moreover, the endcap 712 can be suitably configured to mate with or otherwise cooperate with a biasing component that urges the rotor 702 toward the stator 704. For example, the endcap 712 can be coupled to or integrally fabricated with the spring coupler 164 shown in FIG. 3.

The axial displacement of the rotor 702 relative to the stator 704 is defined by the cooperating cam elements 706, 722. The cam elements contact each other during each pumping cycle to adjust the axial position of the rotor 702 as a function of the angular position of the rotor 702 relative to the stator 704. For the illustrated embodiment (see FIG. 11), the rotor cam element 722 is positioned on the interior portion of the endcap 712, and it extends over a certain predefined arc. The rotor cam element 722 resembles a ramp having a variable height rising from a reference surface of the rotor 702. More specifically, the rotor cam element 722 increases in height over the predefined arc. In contrast, the stator cam element 706 can be realized as a simple protrusion having a stator cam surface that is designed to "ride" along and up the ramp of the rotor cam element 722. It should be appreciated that the stator cam element 706 need not be realized as a simple protrusion, and that an embodiment of the fluid pump mechanism can reverse the functions of the cam elements (such that the rotor cam element 722 is realized as a simple protrusion and the stator cam element 706 is realized as a ramp).

Figure 12:
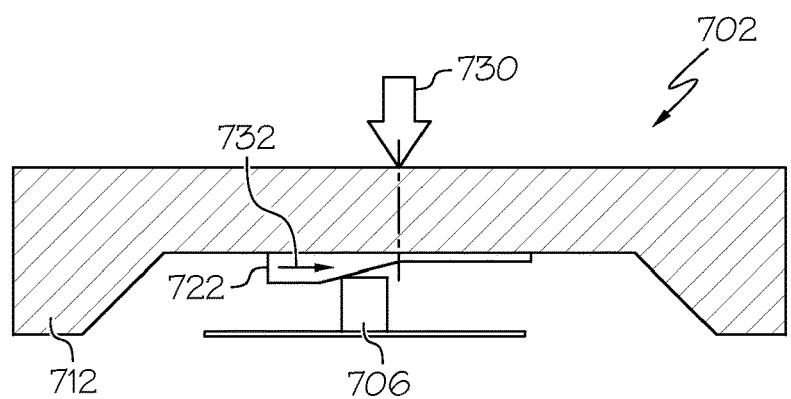
FIGS. 12-14 are diagrams that depict the cooperation between a stator cam element and a rotor cam element of a fluid pump mechanism.
Figure 13:
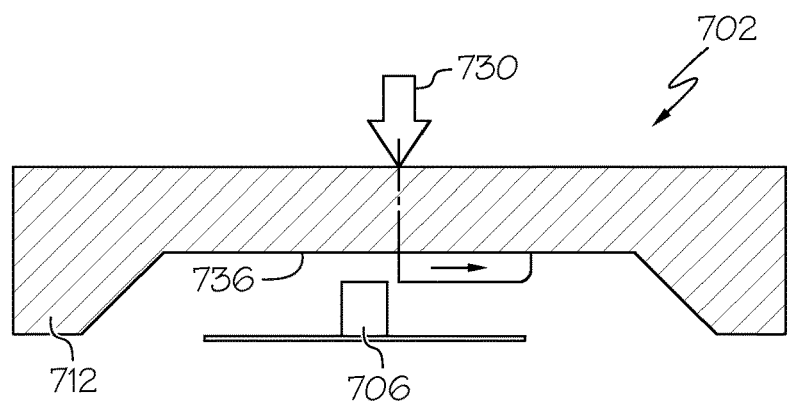
Figure 14:
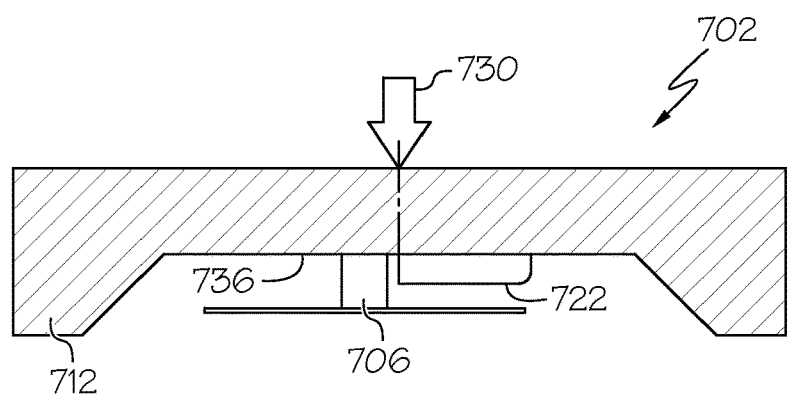

FIGS. 12-14 are diagrams that depict the cooperation between the stator cam element 706 and the rotor cam element 722. FIGS. 12-14 only show the stator cam element 706; the remaining portion of the stator 704 is omitted from these figures. The wide arrow 730 in FIGS. 12-14 represents the axial biasing force that is applied to the rotor 702. This axial biasing force is intended to urge the rotor cam element 722 toward the stator cam element 706 and toward the reference surface of the rotor. The arrow 732 in FIGS. 12-14 indicates the direction of travel of the rotor cam element 722 relative to the stator cam element 706. As explained above, the rotor cam element 722 moves (relative to the stator cam element 706) in response to the rotation of the rotor 702.

FIG. 12 depicts a state where the stator cam element 706 resides on the rotor cam element 722. More specifically, the stator cam element 706 is positioned on the sloped portion of the rotor cam element 722. As the stator cam element 706 continues to "ride" along the rotor cam element 722, the rotor 702 becomes displaced relative to the stator 704. The maximum displacement occurs at the highest section (the plateau) of the rotor cam element 722. The illustrated embodiment of the rotor cam element 722 ends abruptly, as best shown in FIG. 13, which depicts the vertical "shelf" defined at the end of the rotor cam element 722. FIG. 13 depicts a state where the stator cam element 706 has cleared the rotor cam element 722, and before the rotor 702 has been pushed back toward the stator 704 by the biasing force. In this regard, FIG. 13 shows the gap distance between the stator cam element 706 and a reference surface 736 of the endcap 712. This gap distance corresponds to the maximum axial displacement between the stator 704 and the rotor 702. FIG. 14 depicts a state that immediately follows the state shown in FIG. 13. The biasing force moves the rotor 702 toward the stator 704 such that the stator cam element 706 contacts the reference surface 736. The state shown in FIG. 14 corresponds to the minimum axial displacement between the stator 704 and the rotor 702.

Figure 15:
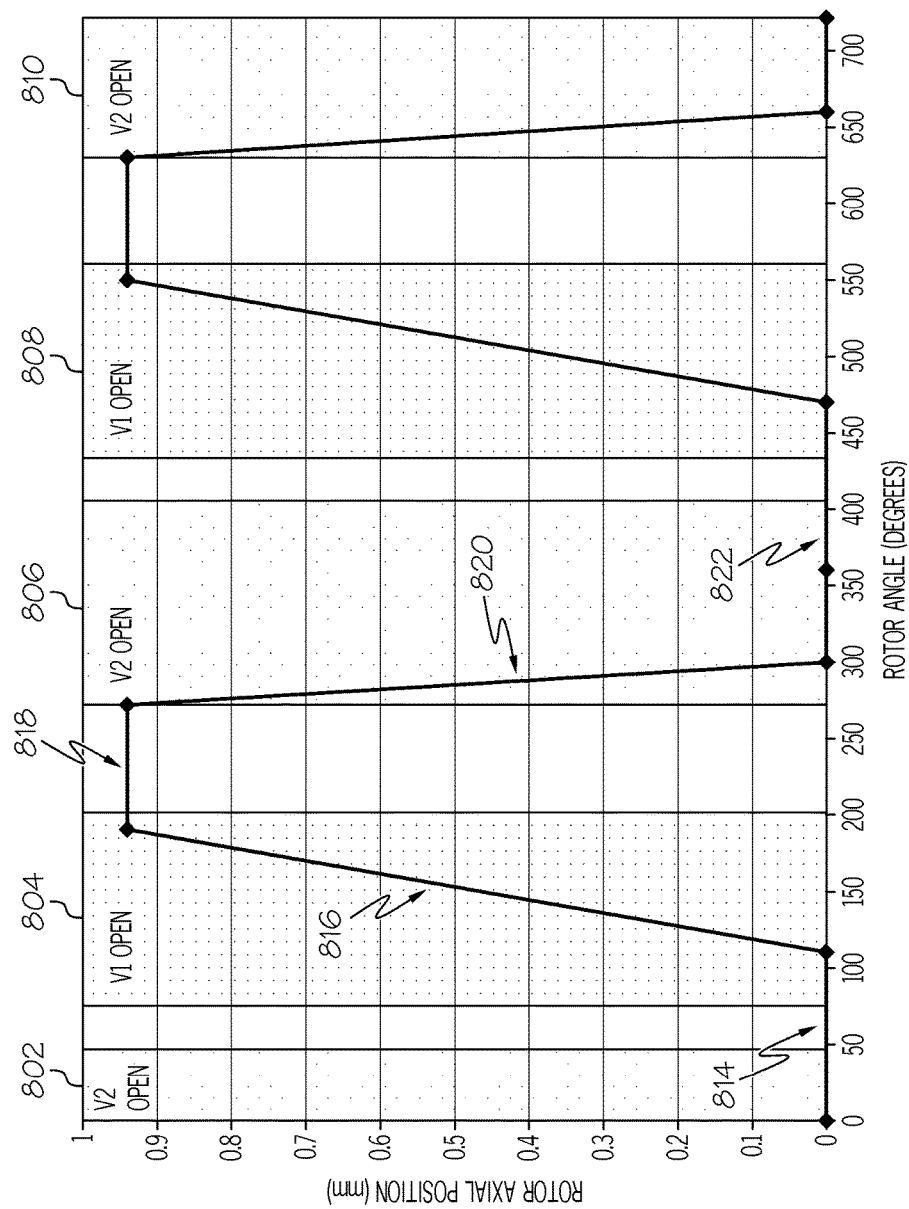
FIG. 15 is a graph that includes a plot of rotor axial position versus rotor angular position.

FIG. 15 is a graph that includes a plot of rotor axial position versus rotor angular position, for normal and typical operating conditions. The vertical axis indicates the axial position (displacement) of the rotor 702 relative to the stator 704, and the horizontal axis indicates the angular position of the rotor 702. One pumping cycle corresponds to 360 degrees of rotation, and FIG. 15 depicts a plot that spans two pumping cycles. FIG. 15 includes regions superimposed over the plot; the regions represent periods during which the valves are open. More specifically, the region 802 corresponds to a first period during which the second/outlet valve (V2) is open, the region 804 corresponds to a second period during which the first/inlet valve (V1) is open, the region 806 corresponds to a third period during which V2 is open, the region 808 corresponds to a fourth period during which V1 is open, and the region 810 corresponds to a fifth period during which V2 is open. The gaps between these five regions correspond to periods during which both valves are closed.

The first section 814 of the plot (where the axial displacement is approximately zero) corresponds to a period during which the stator cam element 706 is in contact with the reference surface 736. The second section 816 of the plot (where the axial displacement increases from about zero to about 0.95 mm) corresponds to a period of time during which the stator cam element 706 rides onto the rotor cam element 722. Notably, the axial displacement increases until the stator cam element 706 reaches the maximum height defined by the rotor cam element 722. During this time, the first valve is open, the second valve is closed, and the axial displacement of the rotor 702 increases the volume of the fluid chamber inside the stator 704, which in turn causes fluid to be drawn into the fluid pump mechanism. Accordingly, the second section 816 of the plot corresponds to a fluid intake period. The third section 818 of the plot (where the axial displacement is constant at about 0.95 mm) corresponds to a period during which the stator cam element 706 rides on the top of the plateau defined by the rotor cam element 722. During most of this period, both of the valves are closed.

The fourth section 820 of the plot (where the axial displacement decreases from about 0.95 mm to about zero) corresponds to a period of time immediately after the stator cam element 706 travels beyond the rotor cam element 722 (see FIG. 13 and FIG. 14). In other words, the stator cam element 706 "falls off" and disengages the plateau of the rotor cam element 722, and the biasing force axially displaces the rotor 702 toward the stator 704 such that the rotor cam element 722 moves toward the reference surface 736. Eventually, the stator cam element 706 reaches and contacts the reference surface 736. During this time, the first valve is closed, the second valve is open, and the axial displacement of the rotor 702 causes the fluid to be expelled from the fluid pump mechanism via the second valve. Accordingly, the fourth section 820 of the plot corresponds to a fluid expulsion period. The fifth section 822 of the plot (where the axial displacement is approximately zero) corresponds to another period during which the stator cam element 706 is in contact with the reference surface 736. Thus, after a fluid expulsion period and before the next fluid intake period, the stator cam element 706 is in contact with the reference surface 736. In this regard, the fifth section 822 is akin to the first section 814, and the next pumping cycle proceeds as the rotor 702 continues to rotate.

Downstream Occlusion Detection

A downstream occlusion in the fluid delivery flow path occurs when something blocks or inhibits the flow of the fluid after it leaves the fluid pump mechanism. Downstream occlusion detection techniques are desirable to increase the safety of a medication infusion device. With particular reference to the fluid pump mechanism described here, downstream occlusion detection can employ one or both of the following general methodologies: (1) axial position measurement of the rotor 702 relative to the stator 704; and (2) force/pressure measurement of the fluid path.

Figure 16:
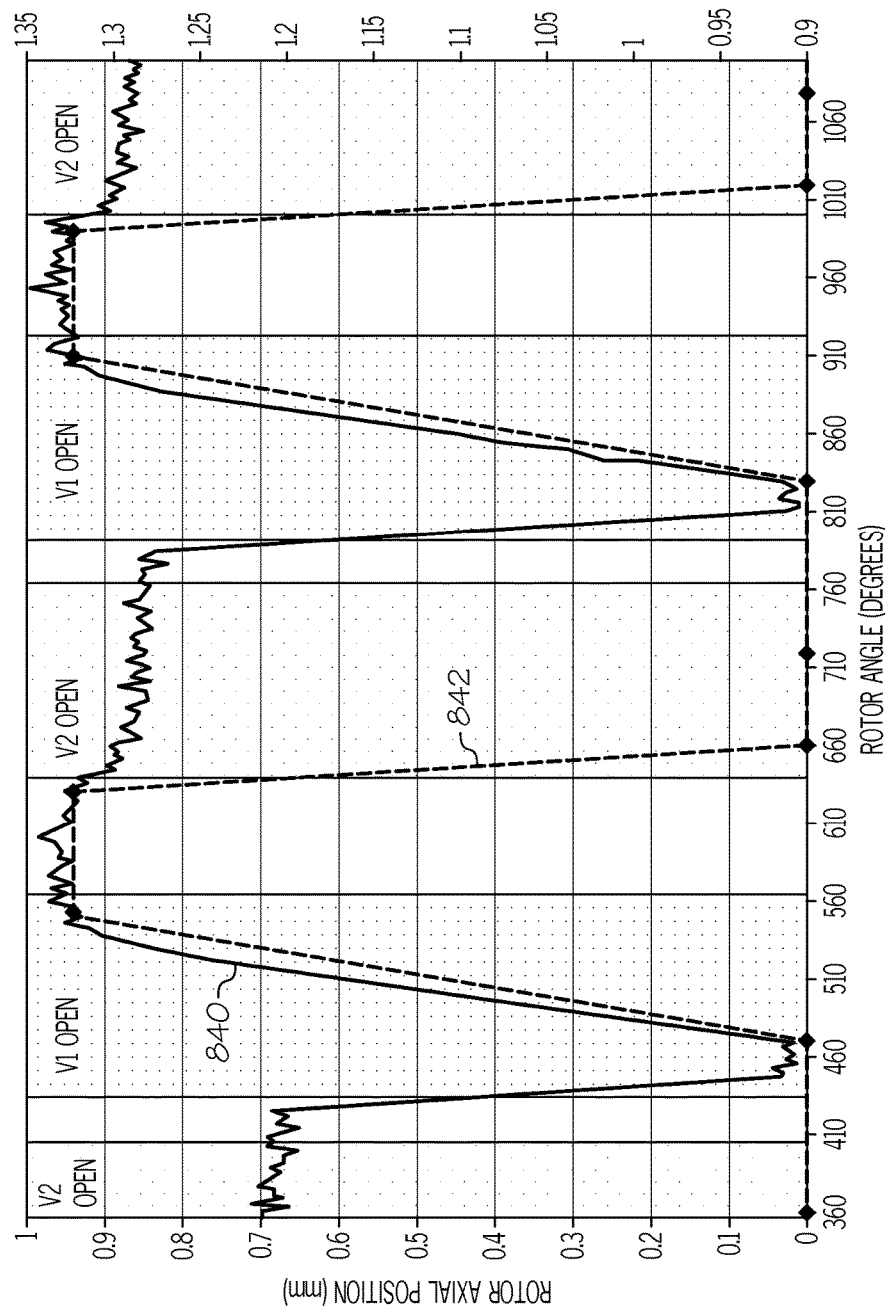
FIG. 16 is a graph that includes a plot of rotor axial position versus rotor angular position for a downstream occlusion condition.

As mentioned above, the axial position of the rotor 702 (relative to the stator 704) as a function of angular rotation is at the core of the pumping action of the fluid pump mechanism. FIG. 15 illustrates the normally expected behavior of the fluid pump mechanism. In practice, the axial position of the rotor 702 relative to the stator 704 can be measured/monitored for purposes of detecting delivery anomalies. For example, during normally expected operation, the stator cam element 706 disengages from the rotor cam element 722 and the axial biasing element (usually a spring) causes the fluid to be expelled through the second valve (V2). In the presence of a downstream occlusion, however, outgoing fluid flow is restricted and incompressibility of the fluid restricts the contraction of the rotor position, thus impacting the axial position of the rotor 702. In this regard, FIG. 16 is a graph that includes a plot 840 of rotor axial position versus rotor angular position for a downstream occlusion condition. FIG. 16 also shows the normally expected plot 842 in dashed lines.

The plot 840 indicates how a downstream occlusion affects the axial displacement of the rotor 702. Here, the plot 840 closely tracks the theoretical plot 842 during the fluid intake portion of the pumping cycle. When the second valve opens and the stator cam element 706 disengages from the rotor cam element 722, however, the axial biasing force does not overcome the fluid pressure caused by the occlusion. Accordingly, the rotor 702 does not completely return to its starting point against the stator 704 until shortly after the first valve opens. When the first valve opens, the fluid can backflow into the fluid reservoir, which in turn enables the axial biasing force to return the rotor 702 to its starting position. As shown in FIG. 16, the axial displacement of the rotor 702 hovers at or near 0.85 mm during the period when the second valve is open, but it quickly drops to about zero once the first valve opens. These characteristics of the plot 840 are indicative of a downstream occlusion. The following sections present a number of techniques and methodologies that are designed to detect and respond to a downstream occlusion, which might cause the behavior depicted in FIG. 16.

Downstream Occlusion Detection: Methodology 1

The occlusion detection methodology presented here utilizes a sensor system integrated into the fluid pump mechanism. The basic design, configuration, and operation of the fluid pump mechanism are consistent with that previously described. The sensor system includes a metal trace or similarly conductive sensor contact element that is installed on or integrated into the rotor and in the area away from the rotor cam element (also referred to as the "off-ramp position"). The sensor system also includes a sensing element on or integrated into the stator, wherein the sensing element cooperates with the sensor contact element during operation of the fluid pump mechanism. In some embodiments, the sensing element is realized as two discrete traces or conductive leads that terminate in the area of the stator cam element. The sensor contact element can be shaped, sized, and positioned such that the stator cam element only makes contact with the sensor contact element during normal fluid delivery operations (and such that the stator cam element does not make contact with the sensor contact element when the downstream fluid path is occluded).

The conductive traces on the stator can be interconnected to appropriately configured electronics, a detection circuit, a processor, or the like. Software running on the fluid infusion device can monitor the state of the sensor system (open/close, high/low, etc.) to determine an operating condition, such as the state of fluid delivery. During normal delivery cycles, the detection circuit observes one binary pattern produced by the sensor system (open, close, open, close, etc.) that correlates to the various intake and expulsion cycles. During certain fault conditions, however, the detection circuit observes a different binary pattern (e.g., open, open), which in turn initiates an alarm or an alert message.

Figure 17:
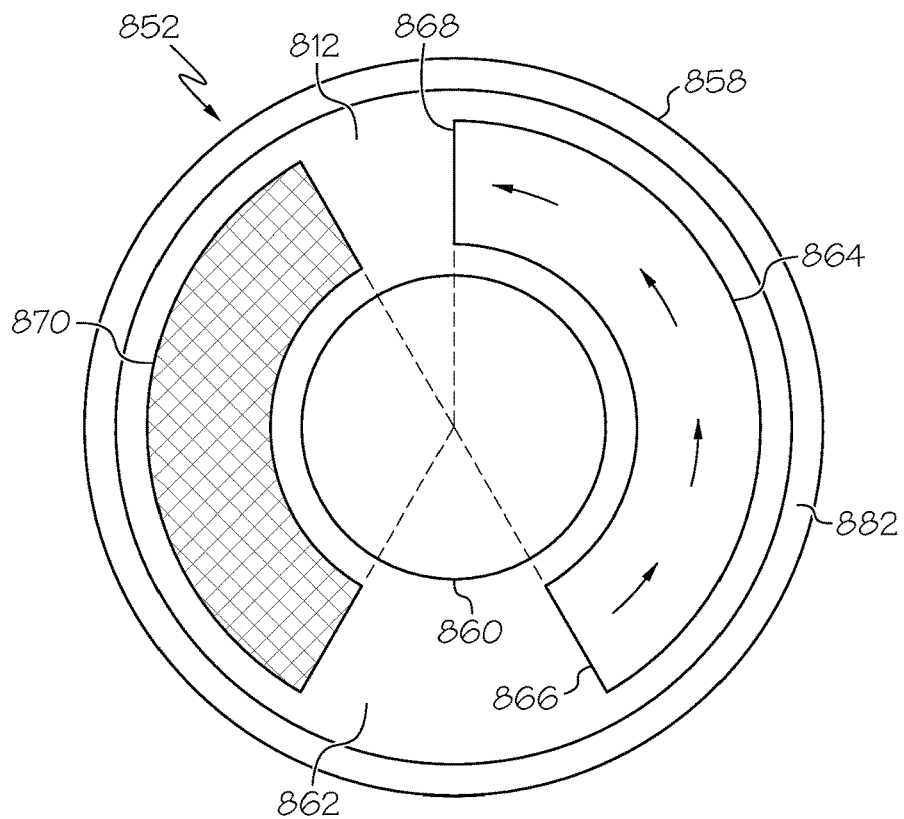
FIG. 17 is an end view of an exemplary embodiment of a rotor of a fluid pump mechanism.
Figure 19:
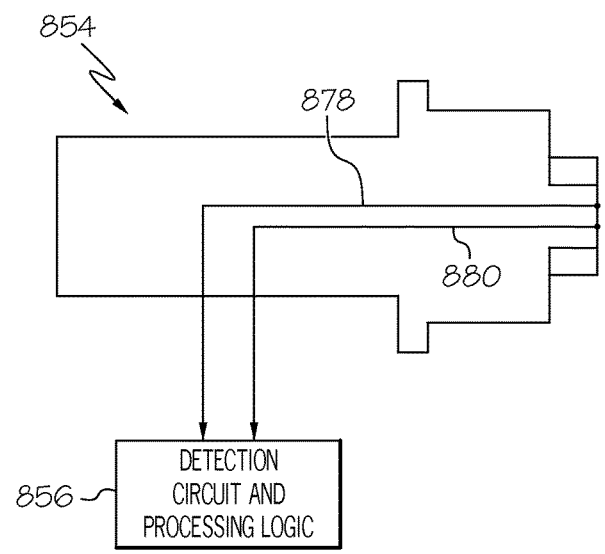
FIG. 19 is a diagram that depicts the stator shown in FIG. 18 cooperating with a detection circuit.

FIG. 17 is an end view of an exemplary embodiment of a rotor 852 of a fluid pump mechanism that implements the occlusion detection methodology described here. FIG. 18 is an end view of an exemplary embodiment of a stator 854 of a fluid pump mechanism that implements the occlusion detection methodology, and FIG. 19 is a diagram that depicts the stator 854 cooperating with a detection circuit 856. The fluid pump mechanism that incorporates the rotor 852 and the stator 854 is similar to that described previously with reference to FIGS. 5-16.

FIG. 17 is an axial end view from the perspective of one looking into the bottom of an endcap 858 of the rotor 852. FIG. 17 depicts the following features, which were described in detail above: an axial extension section 860, which is positioned in the center of the endcap 858; a reference surface 862; and a rotor cam element 864. As mentioned above, the rotor cam element 864 rises above the reference surface 862 from a lower edge 866 to an upper edge 868. FIG. 17 also depicts an exemplary embodiment of a sensor contact element 870, which resides on (or is integrated into) the reference surface 862. In practice, the thickness of the sensor contact element 870 is negligible for purposes of operating the fluid pump mechanism in the manner described previously. The sensor contact element 870 is located in an area that is unoccupied by the rotor cam element 864. As shown in FIG. 17, the sensor contact element 870 can be realized as an arc-shaped electrically conductive trace that is sized such that the reference surface 862 defines a first gap between the lower edge 866 of the rotor cam element 864 and the sensor contact element 870, and a second gap between the upper edge 868 of the rotor cam element 864 and the sensor contact element 870. The span of the sensor contact element 870 and the locations of its leading and trailing edges are carefully selected for compatibility with the angular timing of the rotor 852, and for compatibility with the open/closed states of the inlet and outlet valves. In certain embodiments, the sensor contact element 870 is fabricated using a Laser Direct Structuring (LDS) process comprised of a doped organometallic material that is laser activated and then plated, a two-shot with a chemical activation and then plated, an insert molded contact, etc.

FIG. 18 is an axial end view from the perspective of one looking into the fluid chamber of the stator 854. FIG. 18 depicts a stator cam element 874, which is realized as a protruding tab, and a portion of a sensing element that terminates at or near the stator cam surface 876. Although not always required, the illustrated embodiment of the sensing element includes a first electrically conductive lead 878 (or trace) having an end that is exposed at the stator cam surface 876, and a second electrically conductive lead 880 (or trace) having an end that is exposed at the stator cam surface 876. Each lead 878, 880 also has a second end that cooperates with or is coupled to the detection circuit 856 (see FIG. 19). In alternative embodiments, the sensing element could be realized using conductive springs, tabs, brushes, or the like.

The leads 878, 880 cooperate with the detection circuit 856 to detect whether or not the stator cam surface 876 is in contact with the sensor contact element 870. For example, the detection circuit 856 can monitor the characteristics of a detection signal that is obtained from the leads 878, 880 in response to the changing angular position of the rotor 852. The detection signal could be a measured voltage, current, or the like, having two measurable states corresponding to a contact state and a non-contact state. In this regard, the detection signal obtained from the sensing element can be a binary signal having a first logical state and a second logical state, where the first logical state corresponds to contact between the stator cam element 874 and the sensor contact element 870, and the second state corresponds to non-contact between the stator cam element 874 and the sensor contact element 870. Consequently, a first binary pattern of the detection signal obtained during one rotation of the rotor 852 is indicative of normal and expected operation of the fluid pump mechanism, while a second binary pattern of the detection signal during one rotation of the rotor is indicative of a fault condition of the fluid pump mechanism, e.g., a downstream occlusion, a faulty biasing element, or the like. Under normal operating conditions, the first binary pattern will alternate between the two logical states (high, low, high, low, high, low . . . ). If the downstream fluid path is occluded, however, the fluid back pressure will prevent the stator cam element 874 from reaching the sensor contact element 870 and, therefore, the second binary pattern will include only one state (i.e., the non-contact state). The detection circuit can easily distinguish between these two binary patterns to resolve whether the fluid infusion device is operating as usual or is operating under conditions that indicate a downstream occlusion.

The sensor contact element 870 is shaped, sized, and positioned such that, under normal and expected operating conditions, the stator cam element 874 is in contact with the sensor contact element 870 immediately following each fluid expulsion period. The stator cam element 874 remains in contact with the sensor contact element 870 for a defined angular range of the rotor 852, but the sensor contact element 870 ends before the angular position that corresponds to the next fluid intake period (i.e., the sensor contact element 870 ends before the lower edge 866 of the rotor cam element 864. Moreover, the sensor contact element 870 is located in an area on the reference surface 862 that corresponds to a valve state in which the inlet valve is closed and the outlet valve is open (see FIG. 15 and FIG. 16). Depending on the particular timing and configuration of the fluid pump mechanism, at least a portion of the sensor contact element 870 can be located in an area on the reference surface 862 that corresponds to a valve state in which both the inlet valve and the outlet valve are closed.

Under downstream occlusion conditions, however, fluid pressure caused by an occlusion downstream of the fluid pump mechanism prevents the stator cam element 874 from contacting the sensor contact element 870 after the fluid expulsion period. This enables the detection circuit to determine the presence of a downstream occlusion in response to the characteristics of the detection signal obtained under the downstream occlusion conditions. If the detection circuit detects a downstream occlusion in this manner, it can initiate an alert, an alarm, a warning message, or the like. In some embodiments, the detection circuit triggers an alert in response to detecting a binary pattern in the detection signal that corresponds to a fault condition. In other embodiments, an alert is triggered after a particular binary pattern is detected during a plurality of consecutive rotations of the rotor 852. This requirement may be implemented to minimize false alarms.

Figure 44:
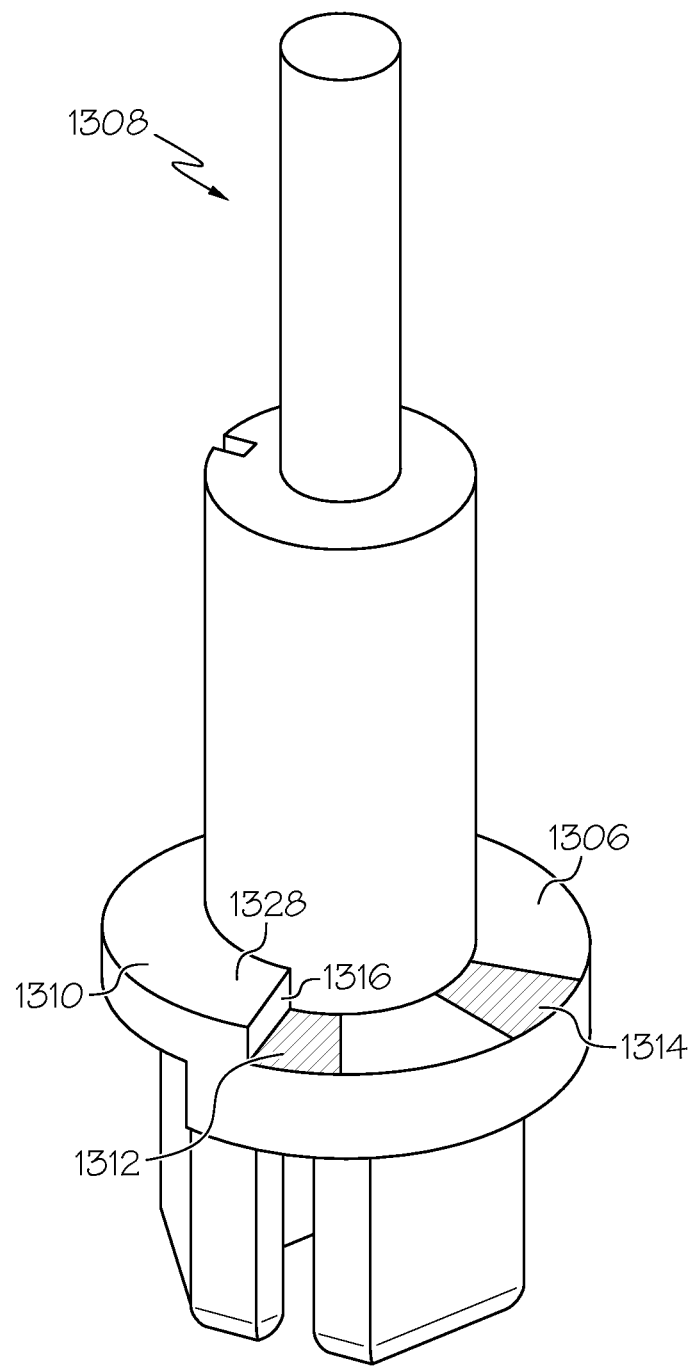
FIG. 44 is a perspective view of an exemplary embodiment of a rotor of a fluid pump mechanism.
Figure 45:
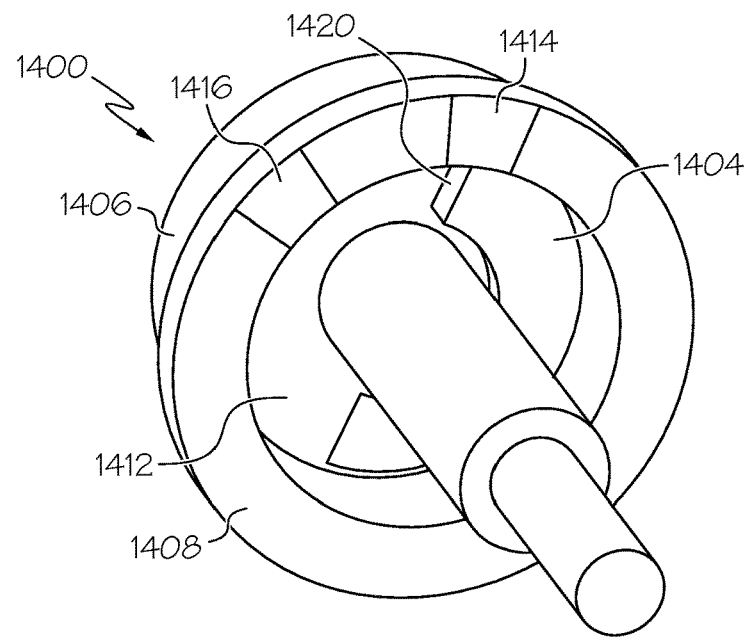
FIG. 45 is a perspective end view of another exemplary embodiment of a rotor of a fluid pump mechanism.
Figure 46:
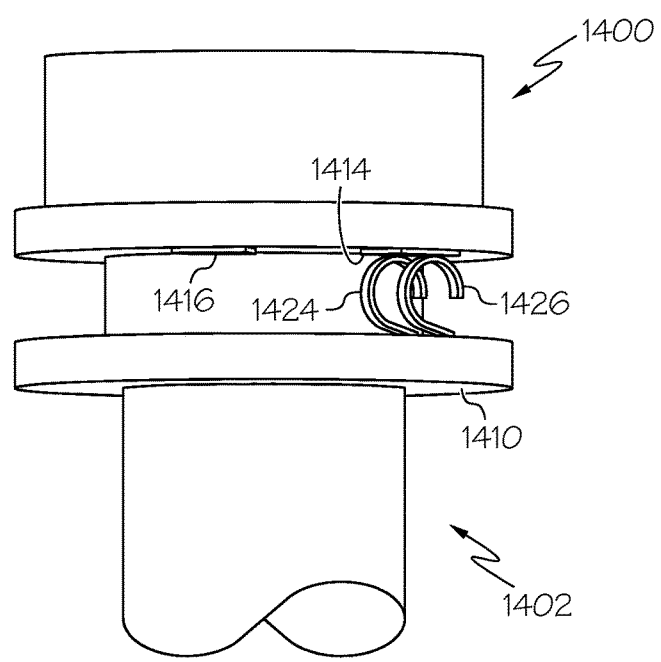
FIG. 46 is a side view that depicts the rotor of FIG. 45 cooperating with a stator.

In alternative embodiments, the sensor contact element is instead located on the rim 882 of the endcap 858 (see FIG. 17). In such embodiments, the angular span of the sensor contact element can be identical or functionally equivalent to that shown in FIG. 17 for the sensor contact element 870. Locating the sensor contact element on the rim 882 instead of inside the endcap 858 may be desirable for ease of manufacturing, reliability, and robust performance. If the sensor contact element is positioned on the rim 882, then the electrically conductive leads of the stator 854 will also be relocated for compatibility with the alternative positioning of the sensor contact element. For example, the leads can be located on a rim or other surface 884 of the stator 854. This type of arrangement is also shown in FIGS. 44-46 in the context of another embodiment.

Downstream Occlusion Detection: Methodology 2

Figure 20:
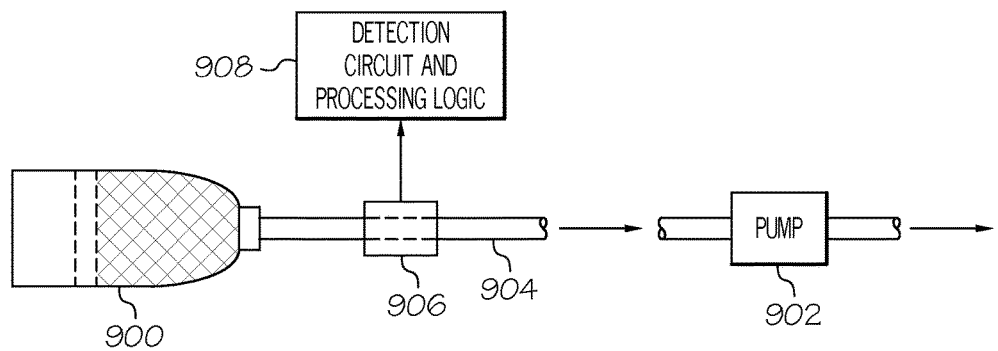
FIG. 20 is a schematic block diagram that illustrates an exemplary embodiment of an occlusion detection system suitable for use with a fluid infusion device.

FIG. 20 is a schematic block diagram that illustrates an exemplary embodiment of an occlusion detection system suitable for use with a fluid infusion device having a fluid cartridge module 900, a fluid pump mechanism 902, and a fluid conduit 904 between the fluid cartridge module 900 and the fluid pump mechanism 902. The fluid pump mechanism 902 is designed to draw medication fluid from the fluid cartridge module 900 during an intake cycle, and thereafter expel the medication fluid during an expulsion cycle. In this regard, the basic operation and functionality of the fluid cartridge module 900 and the fluid pump mechanism 902 are similar to that described above with reference to FIGS. 1-4.

The embodiment of the occlusion detection system shown in FIG. 20 includes an electroactive polymer (EAP) sensor 906 and a detection circuit 908 that is operatively coupled to the EAP sensor 906. The EAP sensor 906 can be realized as a ring-shaped or cylindrical-shaped component that is secured around the fluid conduit 904. For this particular embodiment, the fluid conduit 904 is somewhat resilient, such that it can expand and contract in response to changes in fluid pressure. The EAP sensor 906 is positioned around the exterior of the fluid conduit 904 for purposes of detecting expansion and contraction of the fluid conduit 904 as a function of the operating state of the fluid pump mechanism 902. More specifically, the EAP sensor 906 can monitor the condition of the fluid conduit 904 during fluid intake cycles, fluid expulsion cycles, dwell times, etc.

EAP materials are generally known. For this particular application, the EAP sensor 906 is fabricated from a material (such as a thin film) that generates energy, electricity, voltage, current, or a measurable quantity as a function of mechanical stress or strain imparted thereto. The response of the EAP sensor 906 can be detected and analyzed by the detection circuit 908 as needed. Thus, the EAP sensor 906 is suitably configured to detect or measure the expansion and contraction of the fluid conduit 904 in an ongoing manner.

During a normal and expected fluid delivery cycle, the resilient fluid conduit 904 will collapse or contract during the fluid intake cycle, while the fluid pump mechanism 902 is drawing fluid from the fluid cartridge module 900. Thereafter, the fluid conduit 904 will recover and regain its "nominal" shape (during the fluid expulsion cycle). Accordingly, the EAP sensor 906 is designed to respond to this characteristic contraction and recovery, and the detection circuit 908 takes appropriate action (if any) when the normally expected signal from the EAP sensor 906 is produced. In contrast, if the fluid flow path downstream of the fluid pump mechanism 902 is occluded, then the fluid conduit 904 will not collapse or contract to the same extent that it does during normal delivery. More specifically, the fluid conduit 904 will remain pressurized in the presence of a downstream occlusion until the inlet valve opens again for the next intake stroke. Opening of the inlet valve allows the pressurized fluid to backflow into the upstream fluid path, which in turn allows the resilient fluid conduit 904 to shrink or collapse (relative to its pressurized state). In this scenario, the detection circuit 908 can analyze the output of the EAP sensor 906, determine that a downstream occlusion has occurred, and take appropriate action such as generating an alert.

It should be appreciated that the output of the EAP sensor 906 can also be monitored to detect an "end of reservoir" condition. In this regard, when the fluid cartridge module 900 is empty, the stopper of the fluid reservoir no longer moves because it has reached the limit of its travel. Thus, the fluid pump mechanism 902 generates a negative pressure on the inlet side, which collapses the fluid conduit 904 to a greater extent than experienced during normal delivery (and the fluid conduit 904 does not recover back to its nominal shape).

FIG. 20 shows the EAP sensor 906 monitoring an upstream fluid conduit that resides between the fluid cartridge module 900 and the fluid pump mechanism 902. This arrangement can be effective at detecting upstream occlusions (e.g., an end of reservoir condition). Alternatively or additionally, the system can employ a similar EAP sensor to monitor expansion and contraction of a downstream fluid conduit that is located downstream of the fluid pump mechanism 902. Monitoring a downstream fluid conduit can be effective for purposes of detecting downstream occlusions.

Downstream Occlusion Detection: Methodology 3

In accordance with another downstream occlusion detection methodology, an electrical switch is incorporated in the downstream fluid flow path. For example, a section of the fluid conduit that resides downstream of the fluid pump mechanism can be fabricated from an elastomeric material that is electrically conductive, or that includes an electrically conductive element affixed thereto. The electrically conductive element represents one terminal of a mechanical switch; the other terminal can be positioned in a suitable location adjacent to the fluid conduit.

During a normal and expected fluid delivery cycle, the elastomeric material will expand slightly during the fluid expulsion stage. In the presence of a downstream occlusion, however, the fluid pump mechanism is able to generate substantially more fluid pressure. The increased pressure causes the elastomeric material to expand. As the fluid pump mechanism continues to operate and increase the fluid pressure, the conductive element of the fluid conduit contacts the other switch terminal and creates an electrical short. The closing of the mechanical switch can be detected by a suitably designed detection circuit as an indicator of the downstream occlusion.

Downstream Occlusion Detection: Methodology 4

Figure 21:
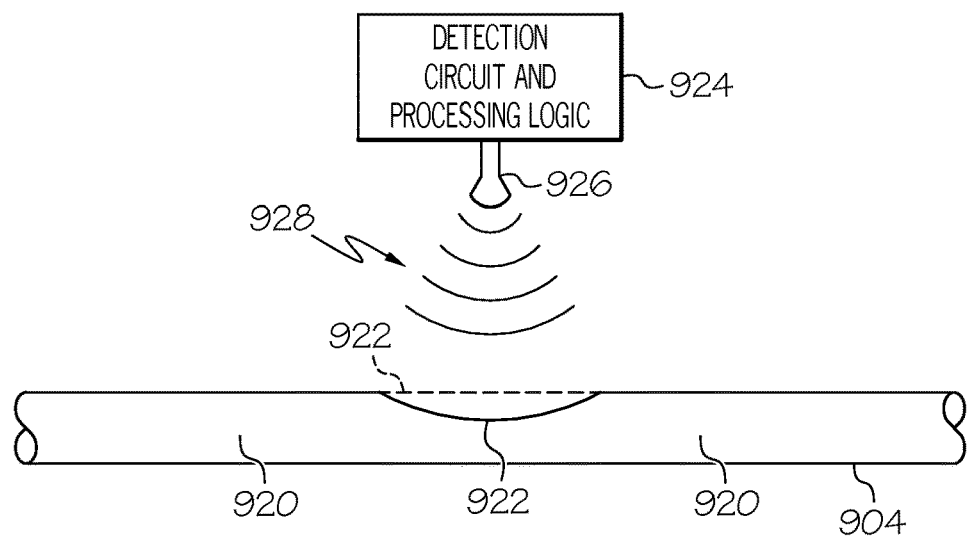
FIG. 21 is a simplified diagram of an exemplary embodiment of an optical or acoustic based occlusion detection system suitable for use with a fluid infusion device.

FIG. 21 is a simplified diagram of an exemplary embodiment of an optical or acoustic based occlusion detection system suitable for use with a fluid infusion device having a fluid cartridge module, a fluid pump mechanism, and a fluid conduit 904 (as generally described above with reference to FIG. 20). FIG. 21 has been simplified to only show the relevant section of the fluid conduit 904. In lieu of (or in addition to) the EAP sensor 906 described above, the embodiment of the occlusion detection system presented here utilizes a non-contact sensing methodology. In certain embodiments, the majority of the fluid conduit 904 is fabricated from a rigid and stiff material 920, such as stainless steel, that exhibits little to no deformation with changes in fluid pressure. At least one section of the fluid conduit 904, however, includes a resilient and compliant component 922. The component 922 moves (expands and contracts) in response to pressure changes inside the fluid conduit 904.

The embodiment of the occlusion detection system shown in FIG. 21 includes a detection circuit 924 that suitably configured to interrogate, observe, or otherwise detect the status of the component 922 without physically touching the component 922. The detection circuit 924 can utilize one or more of the following sensing technologies, without limitation: optical; acoustical; imaging; ultrasound; infrared; or magnetic. The detection circuit 924 can include an interrogation signal emitter 926 that generates interrogation signals 928 (acoustic, optical, magnetic, etc.) for purposes of determining the state of the component 922. In this way, the detection circuit 924 can monitor the condition of the component 922 during fluid intake cycles, fluid expulsion cycles, dwell times, etc.

During a normal and expected fluid delivery cycle, the resilient component 922 will collapse or contract during the fluid intake cycle and will quickly recover and regain its "nominal" shape (during the fluid expulsion cycle). FIG. 21 shows the contracted state of the component 922 using a solid line, and the nominal state of the component 922 using a dashed line. In contrast, if the fluid flow path downstream of the fluid pump mechanism is occluded, then the component 922 will not collapse or contract. The detection circuit 924 employs one or more appropriate non-contact sensing technologies to determine the state of the component 922 and, in turn, to determine whether a downstream occlusion has occurred. It should be appreciated that the flexible component 922 can also be monitored to detect an "end of reservoir" condition. In this regard, when the fluid cartridge module is empty, the component 922 will collapse but will not return back to its nominal shape.

Downstream Occlusion Detection: Methodology 5

As described in detail above with reference to FIGS. 5-14, a rotary fluid pump mechanism includes a rotor and a stator that cooperate to draw fluid from a fluid reservoir and deliver the fluid to an outlet conduit. Axial displacement of the rotor relative to the stator is a function of the angular position of the rotor. Simply put, the rotor moves back and forth relative to the stator during normal and expected fluid pumping cycles. The occlusion detection methodology presented in this section employs at least one non-contact sensing scheme to monitor the position of the rotor relative to the stator during operation of the fluid pump mechanism.

Figure 22:
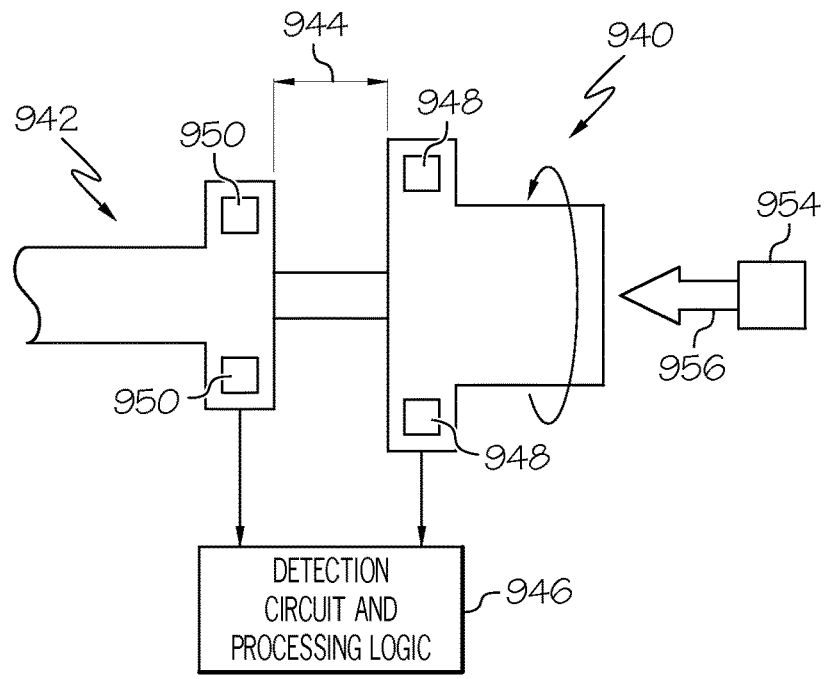
FIG. 22 is a simplified diagram of an exemplary embodiment of an occlusion detection system that utilizes position sensing techniques.

FIG. 22 is a simplified diagram of an exemplary embodiment of an occlusion detection system that utilizes position sensing techniques. FIG. 22 depicts a rotor 940 and a stator 942 of a rotary fluid pump mechanism of the type previously described. Rotation of the rotor 940 usually results in axial displacement of the rotor 940 relative to the stator 942. This axial displacement is represented by the arrow 944 in FIG. 22. As explained previously, the axial position of the rotor 940 (as a function of angular position of the rotor 940) is repeatable and predictable during normal fluid delivery conditions (see FIG. 15). In contrast, the axial position of the rotor 940 exhibits substantially different characteristics in the presence of a downstream occlusion, due to the back pressure caused by the occlusion (see FIG. 16). The techniques presented here detect the relative position of the rotor and/or the stator during operation of the fluid infusion device, and the detected position information is used to determine whether or not the downstream fluid path is occluded.

The embodiment of the occlusion detection system shown in FIG. 22 includes a detection circuit 946 that cooperates with one or more non-contact sensors associated with the rotor 940 and/or the stator 942. For the sake of generality and completeness, FIG. 22 shows multiple rotor sensors 948 and multiple stator sensors 950, each of which cooperates with the detection circuit 946 to provide respective sensor signals, measurable quantities, data, or information that can be analyzed and processed as needed for purposes of occlusion detection. Depending on the particular embodiment, the occlusion detection system can utilize any one of the sensors 948, 950 or any suitable combination of two or more sensors 948, 950.

In accordance with some embodiments, an accelerometer is used for at least one of the rotor sensors 948. The accelerometer data can be processed by the detection circuit to calculate the axial displacement velocity or acceleration of the rotor 940 as a function of its angular position. In this regard, the axial velocity/acceleration of the rotor 940 can be characterized for normal and expected fluid delivery cycles and for downstream occlusion conditions. Referring again to FIG. 15 and FIG. 16, the axial velocity/acceleration of the rotor 940 is expected to be relatively high during a normal fluid delivery period, and relatively low when the downstream fluid path is occluded. The detection circuit 946 can be designed and programmed in an appropriate manner to respond to changes in the axial velocity/acceleration of the rotor 940 that might be indicative of a downstream occlusion.

In accordance with certain embodiments, the occlusion detection system employs a light source and a light sensor to monitor the axial position of the rotor 940 relative to the sensor. In this regard, one or more of the sensors 948, 950 can be realized as a light sensor. Alternatively, one or more light sensors external to the rotor 940 and external to the stator 942 can be used. In accordance with alternative embodiments, a light sensor is provided on the stator 942 (or the rotor 940), and a reflective element is provided on the rotor 940 (or the stator 942).

In yet other embodiments, the sensors 948, 950 are selected to support the desired non-contact sensing technology. In this regard, any of the following non-contact sensing techniques can be utilized with the occlusion detection system depicted in FIG. 22, without limitation: magnetic sensing using, for example, a Hall sensor arrangement; inductive sensing that relies on inductive coupling between the stator 942 and the rotor 940; capacitive sensing that relies on capacitive coupling between the stator 942 and the rotor 940; infrared sensing; or optical imaging.

In accordance with some embodiments, the occlusion detection system includes a force or pressure sensor 954 that is suitably configured and arranged to measure the biasing force associated with the rotor 940. As mentioned previously with reference to FIGS. 5-8, a biasing element can be employed to urge the rotor 940 toward the stator 942. The sensor 954 measures the force 956, which can vary during a fluid delivery cycle. Thus, the force 956 can be characterized for normal and expected fluid delivery cycles and for downstream occlusion conditions, and the detection circuit 946 can be designed and programmed in an appropriate manner to respond to changes in the detected force profile that might be indicative of a downstream occlusion.

Downstream Occlusion Detection: Methodology 6

Figure 23:
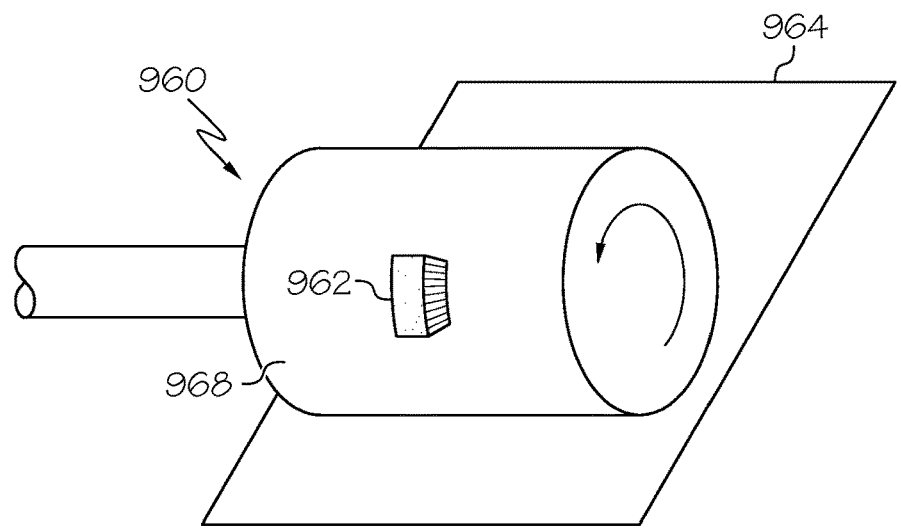
FIG. 23 is a simplified perspective view of an exemplary embodiment of a rotor of a fluid pump mechanism.
Figure 24:
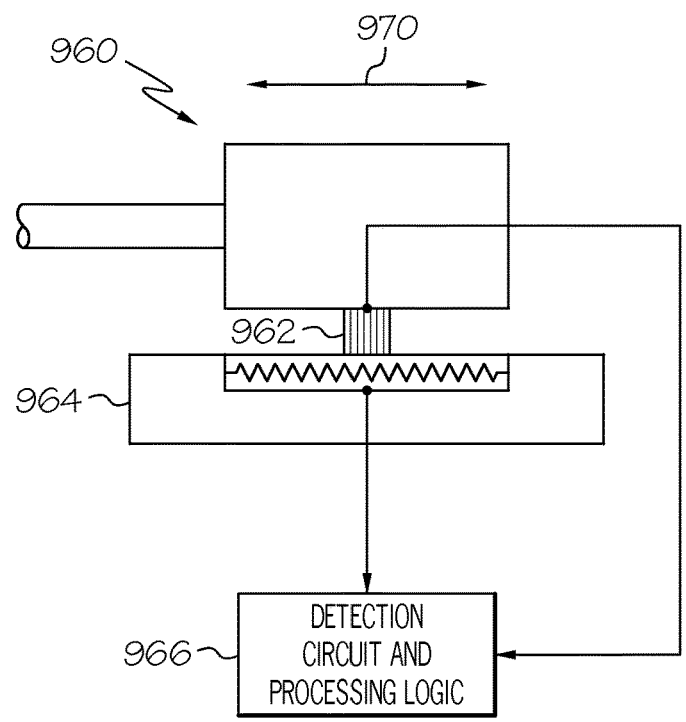
FIG. 24 is a simplified diagram of an exemplary embodiment of an occlusion detection system that utilizes a potentiometer as a sensing element.

The occlusion detection methodology presented in this section utilizes a potentiometer as a sensing element to determine the axial position of the rotor of the fluid pump mechanism. In this regard, FIG. 23 is a simplified perspective view of an exemplary embodiment of a rotor 960 having an electrical contact 962 attached thereto, and FIG. 24 is a simplified diagram of an exemplary embodiment of an occlusion detection system that cooperates with the rotor 960. The occlusion detection system also includes a variable resistance element 964 that cooperates with the electrical contact 962 to form a potentiometer. The electrical contact 962 and the variable resistance element 964 can be electrically coupled to a detection circuit 966, which supports the occlusion detection methodology described here. In practice, the variable resistance element 964 can be realized as a component of the detection circuit 966. Moreover, the variable resistance element 964 can be integrated with or coupled to the stator of the fluid pump mechanism if so desired.

The electrical contact 962 can be realized as a conductive tab, brush, or protrusion that extends from an exterior surface 968 of the rotor 960. The electrical contact 962 is shaped, sized, and positioned on the exterior surface 968 such that it makes electrical contact with the variable resistance element 964 once per revolution of the rotor 960. In certain embodiments, the electrical contact 962 is grounded such that it cooperates with the variable resistance element 964 to form a voltage divider. Although not depicted in FIG. 23 or FIG. 24, the electrical contact 962 can be electrically coupled to ground potential using conductive traces, a ground spring, a wire, or the like.

FIG. 24 depicts the rotor 960 at the sensor interrogation time, i.e., when the electrical contact 962 is touching the variable resistance element 964. The angular position of the rotor 960 (at the time the electrical contact 962 is electrically coupled to the variable resistance element 964) corresponds to a desired interrogation or sampling point of the fluid delivery cycle. For example, the electrical contact 962 can be placed such that it contacts the variable resistance element 964 immediately following each expected fluid expulsion period (see FIG. 15). The specific timing can be determined based on the known angular position characteristics of the fluid pump mechanism.

As explained previously with reference to FIGS. 5-14, the rotor 960 is axially displaced as a function of its angular position. The arrow 970 in FIG. 24 represents the axial displacement of the rotor 960. Axial displacement of the rotor 960 causes the electrical contact 962 to shift back and forth, because the electrical contact 962 is fixed relative to the rotor 960. During normal and expected fluid delivery cycles, the electrical contact 962 should make contact with the variable resistance element 964 within a predictable and repeatable range of possible locations. Consequently, the resistance of the potentiometer changes, and a measured quantity (e.g., voltage) as detected by the detection circuit 966 will be within a certain range during normal delivery cycles. In contrast, the electrical contact 962 will touch the variable resistance element 964 at a considerably different location when the downstream fluid flow path is occluded. Accordingly, the resistance of the potentiometer and the measured voltage will be outside of the normal range of values when the output flow path is occluded. The detection circuit 966 can be designed and programmed in an appropriate manner to respond to changes in the resistance of the potentiometer that might be indicative of a downstream occlusion.

FIG. 24 depicts an embodiment where the electrical contact 962 resides on the rotor 960 and the variable resistance element 964 is external to the rotor 960. In other embodiments, the variable resistance element 964 resides on the rotor 960 and the electrical contact 962 is external to the rotor 960. Regardless of which configuration is used, the operating principle remains the same.

Downstream Occlusion Detection: Methodology 7

Figure 25:
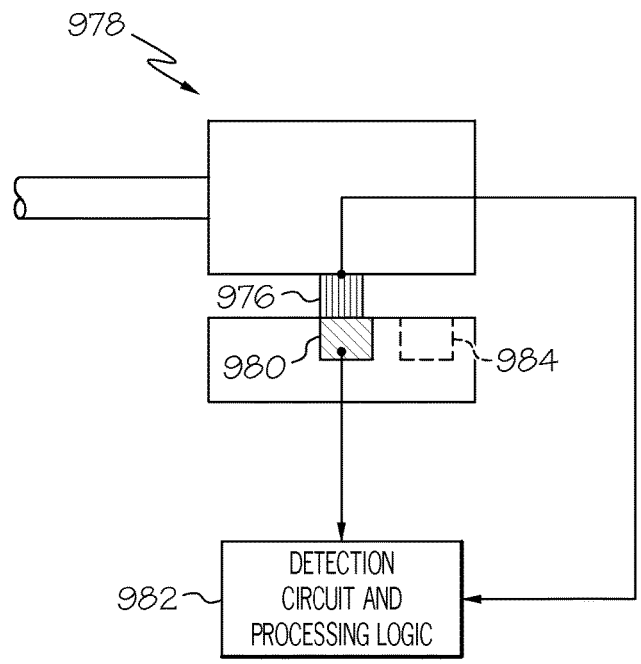
FIG. 25 is a simplified diagram of an exemplary embodiment of an occlusion detection system that utilizes an electrical contact as a digital switch.

The occlusion detection methodology presented in this section utilizes an electrical contact as a digital switch to indicate the presence of a downstream occlusion. In this regard, FIG. 25 is a simplified diagram of an exemplary embodiment of an occlusion detection system that utilizes an electrical contact 976 that is integrated with or affixed to the rotor 978 (similar to that described in the previous section with reference to FIG. 23 and FIG. 24). The occlusion detection system shown in FIG. 25 includes an electrically conductive element 980 that is external to the rotor 978. The electrically conductive element 980 is positioned and arranged such that the electrical contact 976 touches the conductive element 980 at a specified angular position of the rotor 978, e.g., the angular position that corresponds to a period immediately following the fluid expulsion cycle of the fluid pump mechanism.

FIG. 25 depicts the normal and expected state following the fluid expulsion cycle. The electrical contact 976 is expected to make contact with the conductive element 980. In contrast, if the downstream flow path is occluded, then the electrical contact 976 will be displaced from the conductive element 980. The detection circuit 982 can distinguish between a closed electrical contact (which indicates normal delivery status) and an open electrical contact (which indicates an occluded status). In practice, therefore, the electrical contact 976 can be grounded or otherwise held at an appropriate reference voltage. In some embodiments, a second electrically conductive element 984 can be utilized to detect an occluded state, wherein the conductive element 984 is positioned to be aligned with the electrical contact 976 when the rotor 978 is in the shifted position caused by an occlusion.

Downstream Occlusion Detection: Methodology 8

Figure 26:
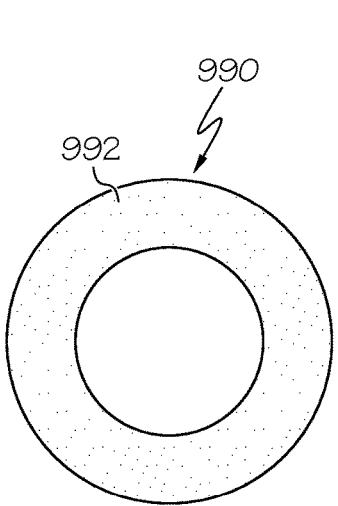
FIG. 26 is a simplified end view of a stator having an electrically conductive rim.
Figure 27:
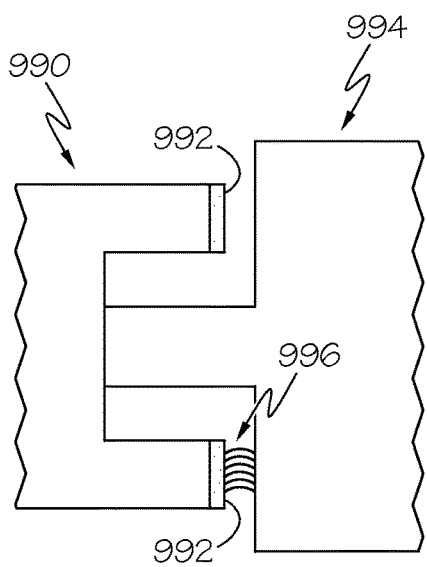
FIG. 27 is a simplified diagram of an exemplary embodiment of an occlusion detection system that cooperates with the stator shown in FIG. 26.

The occlusion detection methodology presented in this section utilizes an electrical contact having a variable resistance that indicates the presence of a downstream occlusion. In this regard, FIG. 26 is a simplified end view of a stator 990 having an electrically conductive rim 992, and FIG. 27 is a simplified diagram of an exemplary embodiment of an occlusion detection system that cooperates with the stator 990. FIG. 27 also depicts a rotor 994 that cooperates with the stator 990. The rotor 994, the stator 990, and the associated fluid pump mechanism function in the manner generally described above with reference to FIGS. 5-16. For the sake of simplicity and clarity, the various electrical connections and detection circuit are not shown in FIG. 27.

The illustrated embodiment of the stator 990 terminates at the conductive rim 992, which faces the rotor 994 (see FIG. 27). The conductive rim 992 is electrically coupled to the detection circuit. The rotor 994 includes an electrically conductive contact 996, which may be realized as a conductive brush, tab, spring, or the like. The conductive contact 996 is also electrically coupled to the detection circuit. The conductive contact 996 maintains physical and electrical contact with the conductive rim 992 during operation of the fluid pump mechanism, regardless of whether the downstream fluid flow path is occluded. In this regard, as the rotor 994 spins relative to the stator 990, the conductive contact 996 follows the circular path of the conductive rim 992.

The conductive contact 996 is designed such that the resistance of the conductive contact 996 varies as a function of its physical compression and/or deflection. The conductive contact 996 compresses or deflects more as the gap between the rotor 994 and the conductive rim 992 closes. Conversely, the conductive element expands or returns to its nominal shape as the gap increases. Thus, the resistance of the conductive contact 996 changes as a function of the axial displacement of the rotor 994 relative to the stator 990. The resistance between the conductive contact 996 and the conductive rim 992 can be measured by the detection circuit, which can be suitably designed and programmed to respond to changes in the measured resistance that might be indicative of a downstream occlusion. For example, under normal and expected operating conditions, the detection circuit expects to obtain a resistance measurement that falls within a particular range when the angular position of the rotor corresponds to the period immediately following the fluid expulsion cycle. If a downstream occlusion prevents the rotor 994 from moving toward the stator 990, then the measured resistance will be different by at least a threshold amount. The detection circuit can respond in an appropriate manner to such detected changes in the measured resistance.

The arrangement depicted in FIG. 26 and FIG. 27 can also be configured for use as a simple on/off switching mechanism. In this context, the detection circuit can be designed to detect whether or not the conductive contact 996 is electrically coupled to the conductive rim 992. For this alternative implementation, the conductive contact 996 and the conductive rim 992 are configured such that an electrical connection is made only when the stator cam element resides on the reference surface. The detection circuit can detect the presence of a downstream occlusion in a manner similar to that described above with reference to FIGS. 17-19.

Downstream Occlusion Detection: Methodology 9

Figure 28:
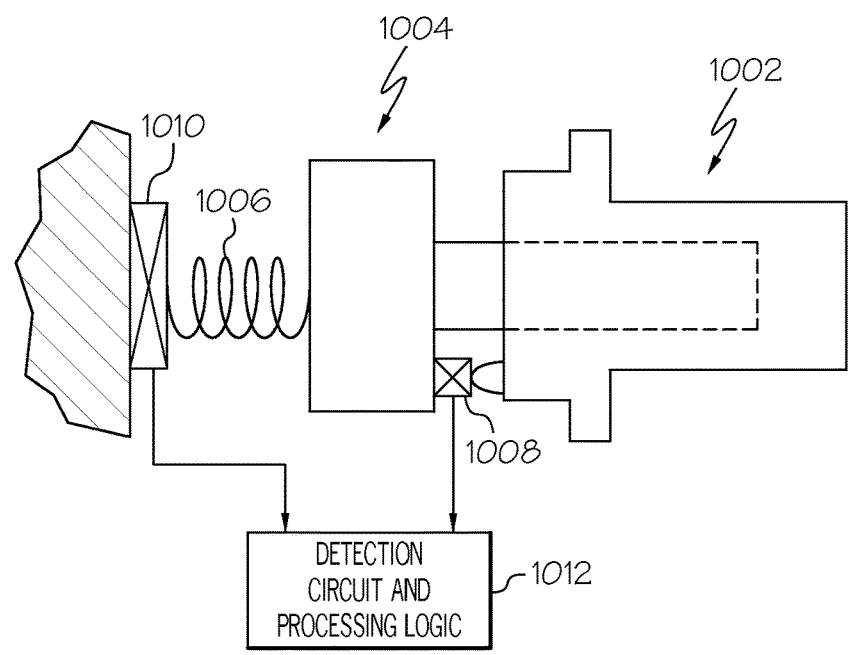
FIG. 28 is a simplified diagram of an exemplary embodiment of an occlusion detection system that utilizes a force sensor.

The occlusion detection methodology presented in this section utilizes a force sensor that generates output levels that can be analyzed to determine whether the downstream fluid path is occluded. In this regard, FIG. 28 is a simplified diagram of an exemplary embodiment of an occlusion detection system that utilizes one or more force sensors in cooperation with the fluid pump mechanism. FIG. 28 depicts a stator 1002, a rotor 1004, and a biasing element 1006 of a fluid pump mechanism that functions in the manner generally described above with reference to FIGS. 5-16. FIG. 28 also shows a force sensor 1008 positioned between the rotor 1004 and the stator 1002, and another force sensor 1010 positioned such that it can measure the biasing force of the biasing element 1006. One or both of the force sensors 1008, 1010 can be utilized in an embodiment of the fluid infusion device. The force sensors 1008, 1010 are suitably designed and configured to generate output levels in response to force imparted thereto, and the output levels can be obtained, processed, and analyzed by an appropriate detection circuit 1012.

For the illustrated embodiment, the force sensor 1008 is positioned and configured to measure force applied by the stator 1002 to the force sensor 1008. Thus, the force sensor 1008 can be located on a flange, shoulder, or other structural feature of the rotor 1004 such that the stator 1002 (or a physical feature thereof) can interact with the force sensor 1008 when necessary to obtain force measurements. In alternative embodiments, the force sensor 1008 can be positioned and configured to measure force applied by the rotor 1004 to the force sensor 1008. In this regard, the force sensor 1008 can be located on a flange, shoulder, or other structural feature of the stator 1002 such that the rotor 1004 (or a physical feature thereof) can interact with the force sensor 1008 when necessary to obtain force measurements.

The force sensor 1010 can be positioned and configured to measure the force applied by the biasing element 1006 to the rotor 1004, the force applied by the rotor 1004 to the biasing element 1006, etc. FIG. 28 depicts the force sensor 1010 coupled between one end of the biasing element 1006 and a supporting structure 1014 of the fluid infusion device. In alternative implementations, the force sensor 1010 can be coupled between the other end of the biasing element 1006 and the rotor 1004. It should be appreciated that other arrangements and locations for a force sensor can be utilized in an embodiment, and that the configuration shown in FIG. 28 is not intended to be restrictive or limiting.

The force sensor 1008, 1010 is designed to react in response to force imparted thereto. In this regard, electrical, mechanical, magnetic, and/or other measurable or detectable characteristics of the force sensor 1008, 1010 vary in accordance with the amount of force applied to the force sensor 1008, 1010. In practice, the force sensor 1008, 1010 might implement or otherwise leverage known sensor technologies. As shown in FIG. 28, the force sensor 1008, 1010 includes at least one electrical lead that is electrically coupled to the detection circuit 1012 of the fluid infusion device. Alternatively, the force sensor 1008, 1010 could use wireless data communication technology to provide force-related data to the detection circuit 1012. In certain implementations, the force sensor 1008, 1010 is suitably configured to indicate or generate a plurality of different output levels that can be monitored and/or determined by the detection circuit 1012. In practice, the output levels obtained from the force sensor 1008, 1010 are initially conveyed as analog voltages or analog currents, and the detection circuit 1012 includes an analog-to-digital converter that transforms a sampled analog voltage into a digital representation. Conversion of sensor voltage into the digital domain is desirable for ease of processing, comparison to threshold values, and the like.

In particular embodiments, the force sensor 1008, 1010 is realized as an electromechanical component having at least one variable resistance that changes as the force applied to the force sensor 1008, 1010 changes. In alternative embodiments, the force sensor 1008, 1010 is a capacitive sensor, a piezoresistive sensor, a piezoelectric sensor, a magnetic sensor, an optical sensor, a potentiometer, a micro-machined sensor, a linear transducer, an encoder, a strain gauge, or the like, and the detectable parameter or characteristic might be compression, shear, tension, displacement, distance, rotation, torque, force, pressure, or the like. In practice, changing characteristics of the force sensor 1008, 1010 are associated with output signal characteristics that are responsive to a physical parameter to be measured. Moreover, the range and resolution of the monitored output signal provides for the desired number of output levels (e.g., different states, values, quantities, signals, magnitudes, frequencies, steps, or the like) across the range of measurement. For example, the force sensor 1008, 1010 might generate a low or zero value when the applied force is relatively low, a high or maximum value when the applied force is relatively high, and intermediate values when the applied force is within the detectable range.

In certain exemplary embodiments, the detection circuit 1012 of the fluid infusion device maintains a constant supply voltage across the force sensor 1008, 1010, and the monitored output signal of the force sensor 1008, 1010 is a signal current that passes through a resistive material of the force sensor 1008, 1010. Thus, the signal current varies with the amount of force applied to the force sensor 1008, 1010 because the resistance of the force sensor 1008, 1010 varies with force and the supply voltage across the force sensor 1008, 1010 is constant. The detection circuit 1012 converts the monitored signal current into a signal voltage, which is then used as an indication of the force imparted to the force sensor 1008, 1010 (which varies as a function of axial displacement of the rotor 1004 relative to the stator 1002). In alternative embodiments, a constant supply current is used and the signal voltage across the force sensor 1008, 1010 varies with force.

As explained above with reference to FIGS. 5-16, the axial displacement of the rotor 1004 (relative to the stator 1002) exhibits a predictable back and forth pattern that corresponds to each pumping cycle of the fluid pump mechanism. For the force-based methodology presented in this section, the force sensor 1008, 1010 generates output levels in response to force imparted thereto, and the force sensor 1008, 1010 cooperates with the detection circuit 1012 for purposes of occlusion detection. To this end, the detection circuit 1012 obtains and processes the sensor output levels to detect occlusions in the fluid path downstream of the fluid pump mechanism. In accordance with the exemplary methodology described here, the force sensor 1008, 1010 is used to obtain force measurements following each fluid expulsion period and before the next fluid intake period. Moreover, the force measurements are obtained when the outlet valve is open. (see FIG. 15 and FIG. 16).

Under normal and expected operating conditions, the axial displacement of the rotor 1004 should be zero or very close to zero during the force measurement period because the biasing element 1006 should force the rotor 1004 into the stator 1002 to expel fluid from the outlet valve. Consequently, the force sensor 1008, 1010 generates baseline or nominal output levels that fall within a range of expected output levels. If the force sensor 1008 is utilized, then the nominal output levels will translate to a relatively high force measurement. Conversely, if the force sensor 1010 is utilized, then the nominal output levels will translate to a relatively low force measurement.

Under downstream occlusion conditions, however, fluid pressure can prevent or inhibit axial displacement of the rotor 1004 toward the stator 1002 (see FIG. 16). As a result, the force sensor 1008, 1010 generates outlier output levels that fall outside the range of expected output levels. The outlier output levels are indicative of a downstream occlusion. More specifically, the detection circuit 1012 can detect and determine the presence of a downstream occlusion in response to obtaining the outlier output levels. For example, if the detection circuit 1012 observes outlier output levels that satisfy certain threshold criteria (e.g., above or below a predetermined threshold value for any one pumping cycle or for a specified number of consecutive pumping cycles), then the detection circuit 1012 can declare that a downstream occlusion has occurred and, thereafter, take appropriate action.

If the force sensor 1008 is deployed, then a downstream occlusion will result in output levels that translate to relatively low force measurements that can be detected and distinguished from normal and expected force measurements (which will be higher). Conversely, if the force sensor 1010 is used, then a downstream occlusion will result in output levels that translate to relatively high force measurements that can be detected and distinguished from normal and expected force measurements (which will be lower). Regardless of which force sensor 1008, 1010 is employed, the detection circuit 1012 can respond in an appropriate manner when it detects a downstream occlusion based on outlier force sensor readings.

Downstream Occlusion Detection: Methodology 10

The occlusion detection methodology presented in this section assumes that the fluid pump mechanism described above (with reference to FIGS. 5-16) uses a conductive compression spring as the biasing element 506. The conductive spring is electrically coupled to a detection circuit that is suitably configured to measure the inductance of the conductive spring. In practice, the detection circuit can include an inductance-to-digital converter to obtain readings that are indicative of the inductance of the conductive spring.

The inductance of the conductive spring is a function of its compression/extension. Accordingly, the measured inductance of the conductive spring should vary as a function of the axial displacement of the rotor relative to the stator. Thus, the measured inductance can be analyzed at certain times during the pumping cycle for purposes of determining whether or not a downstream occlusion has occurred. For example, the inductance of the conductive spring can be checked at the time immediately following each fluid expulsion cycle, when the rotor cam element is expected to be in contact with the reference surface (see FIG. 15 and FIG. 16). Measured inductance values that fall within a range of expected values are indicative of normal operating conditions. In contrast, measured inductance values that fall outside the range of expected values may be indicative of a downstream occlusion.

Downstream Occlusion Detection: Methodology 11

The occlusion detection methodology presented in this section utilizes optical detection techniques to determine whether the downstream fluid path is occluded. In accordance with one implementation, an optical sensor or detector interrogates an optically detectable pattern (such as a dot array) that is printed on an exposed surface of the rotor of the fluid pump mechanism. In accordance with an alternative implementation, an optical sensor or detector interrogates a physical structure of the rotor.

Figure 29:
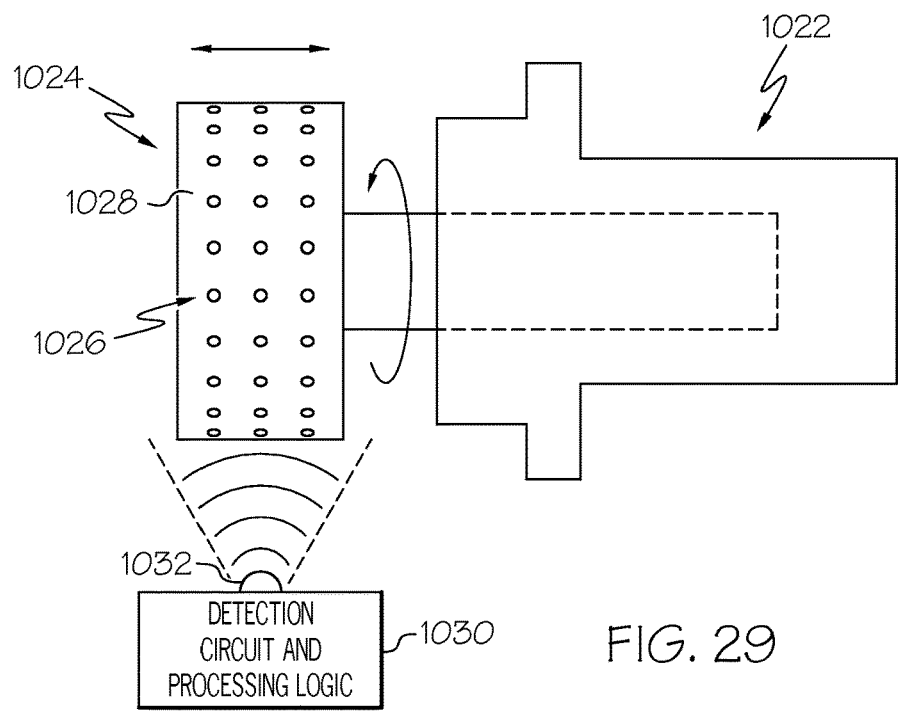
FIG. 29 is a simplified diagram of an exemplary embodiment of an occlusion detection system that utilizes optical sensing technology.

FIG. 29 is a simplified diagram of an exemplary embodiment of an occlusion detection system that utilizes optical sensing technology. FIG. 29 depicts a stator 1022 and a rotor 1024 of a fluid pump mechanism that functions in the manner generally described above with reference to FIGS. 5-16. The rotor 1024 includes at least one optically detectable feature that can be monitored during the operation of the fluid pump mechanism. In this regard, FIG. 28 also shows an exemplary embodiment of an optically detectable feature, which is realized as an optically detectable pattern 1026 located on an exposed surface 1028 of the rotor 1024. For the illustrated embodiment, the optically detectable pattern 1026 is a dot array, which can be printed, affixed to, or integrated into the exposed surface 1028. Other types of optically detectable patterns 1026 can be employed if so desired.

The optically detectable pattern 1026 can be located around the outer circumference of the endcap of the rotor 1024, as depicted in FIG. 29. In certain embodiments, the optically detectable pattern 1026 is visible regardless of the angular position of the rotor 1024. In other embodiments, the optically detectable pattern 1026 need not completely encircle the exposed surface 1028. In such embodiments, the optically detectable pattern 1026 can be located in one or more regions of the rotor 1024, where the regions correspond to angular positions of the rotor 1024 that require optical sensing.

The fluid infusion device includes a detection circuit 1030 that includes an optical emitter/sensor element 1032, along with the appropriate optical sensing processing logic and intelligence. The detection circuit 1030 can leverage any known or available optical sensing or detection technology, and such conventional technology will not be described in detail here. For example, the detection circuit 1030 can employ LED or laser sensing technology that is commonly used in optical mouse peripherals. In this regard, an optical mouse contains a small LED that interrogates a work surface, and a CMOS sensor that detects the reflected light. The sensor sends the captured image data to a signal processor for analysis to determine how the images/patterns have changed over time. In practice, the detection circuit 1030 may include a suitably configured emitter that generates optical interrogation signals, and a compatible sensor that can detect the pattern 1026 in response to the interrogation signals. In this way, the detection circuit 1030 can resolve any or all of the following, at any given time: the angular position of the rotor 1024; the axial position/displacement of the rotor 1024; the angular velocity of the rotor 1024; the angular acceleration of the rotor 1024; the velocity of the rotor 1024 in the axial direction; and the acceleration of the rotor 1024 in the axial direction.

Notably, the optically detectable pattern 1026 is fixed relative to the exposed surface 1028 and, therefore, the optically detectable pattern 1026 rotates and axially translates as a function of the angular position of the rotor 1024. As described in detail above with reference to FIGS. 5-16, one rotation of the rotor 1024 corresponds to one pumping cycle, and the rotor 1024 (along with the pattern 1026) axially translates back and forth during normal and expected operating conditions. Accordingly, the optical emitter/sensor element 1032 includes an optical sensing range that covers the desired portion of the optically detectable pattern 1026, and that contemplates the range of axial displacement of the rotor 1024. This allows the detection circuit 1030 to optically interrogate the pattern 1026 during operation of the fluid pump mechanism and, in response to the optical detection, determine the operating condition or state of the fluid pump mechanism.

As explained above with reference to FIGS. 5-16, the rotor 1024 axially translates in a predictable back-and-forth manner when the fluid infusion device is operating under normal and expected conditions. In turn, the optically detectable pattern 1026 axially translates in the same predictable manner. The detection circuit 1030 is configured to observe this characteristic movement of the pattern 1026, which is indicative of normal operating conditions. In this regard, the detection circuit 1030 can determine that the operating condition of the fluid pump mechanism is normal. The pattern 1036 can also be observed to detect rotation of the rotor 1024 for purposes of correlating the angular position of the rotor 1024 with its axial displacement (if so desired).

Under downstream occlusion conditions, the rotor 1024 does not return to its nominal axial position. In other words, the fluid pressure caused by a downstream occlusion prevents the rotor cam element from contacting the reference surface as expected. Consequently, during each occluded pumping cycle, the optically detectable pattern 1026 axially translates in accordance with a different characteristic movement that is optically distinguishable from the normally expected characteristic movement. Thus, the detection circuit 1030 can observe the different characteristic movement to determine that the operating condition of the fluid pump mechanism corresponds to a downstream occlusion.

In accordance with alternative embodiments, the optically detectable feature of the rotor is realized as a physical structure (or structures) that can be observed by the detection circuit. In this regard, FIG. 30 is a simplified perspective view of an exemplary embodiment of a rotor 1040 having physical features that cooperate with an optical detection circuit (not shown), and FIG. 31 is a side view of a section of the rotor 1040.

Figure 30:
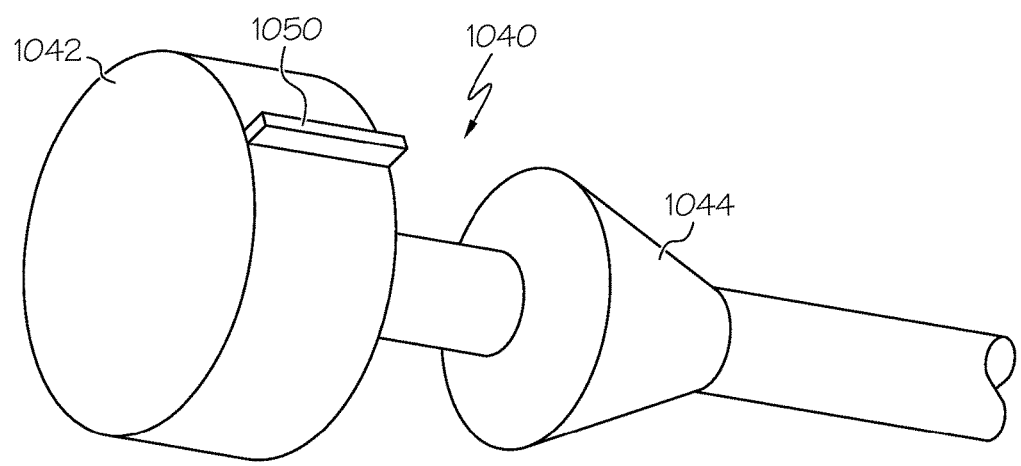
FIG. 30 is a simplified perspective view of an exemplary embodiment of a rotor having physical features that cooperate with an optical detection circuit.
Figure 31:
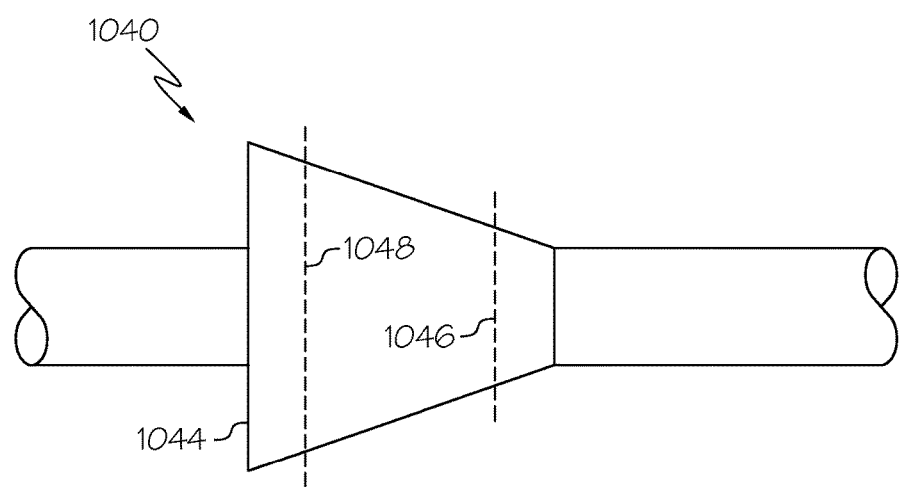
FIG. 31 is a side view of a section of the rotor shown in FIG. 30.

FIG. 30 depicts the portion of the rotor 1040 that remains exposed during operation of the fluid pump mechanism, including an endcap 1042 and a tapered section 1044 having an asymmetrical profile (see FIG. 31). The tapered section 1044 represents one physical structure of the rotor 1040 that can be optically interrogated by a detection circuit such as the detection circuit 1030 described previously. The tapered section 1044 can be realized as an integrated portion of the rotor 1040, or it could be a separate component that is attached to the shaft of the rotor 1040. It should be appreciated that the optically detectable physical structure can be shaped, sized, and configured in an alternate way, and that the generally conical tapered section 1044 shown in FIG. 30 and FIG. 31 is merely one example of a suitable implementation.

The optical interrogation signal can be focused at a specified location such that different areas of the tapered section 1044 are observed as the rotor 1040 is displaced in the axial direction. For example, a narrower section 1046 of the tapered section 1044 can be observed when the rotor 1040 returns to its nominal baseline position (immediately following fluid expulsion), and a wider section 1048 of the tapered section 1044 can be observed when the rotor 1040 is axially displaced during a fluid intake cycle.

The detection circuit can be designed to detect the different widths of the tapered section 1044 and to determine whether or not the downstream fluid path is occluded, based on the detected width and the angular position of the rotor 1040. Alternatively, the detection circuit can be designed to detect the distance between the exposed surface of the tapered section 1044 and the optical emitter, and to determine whether or not the downstream fluid path is occluded, based on the detected distance and the angular position of the rotor 1040.

The rotor 1040 can also include another optically detectable physical feature, such as a tab 1050 located around the periphery of the endcap 1042. The detection circuit can include a second optical emitter/sensor to interrogate the periphery of the endcap 1042 for purposes of detecting the rotation of the rotor 1040. In this regard, the tab 1050 is optically detected once per revolution of the rotor 1040. Notably, the tab 1050 can be located in a particular position on the rotor 1040 in accordance with the desired timing characteristics of the detection circuit, the expected axial translation characteristics, and the configuration of the tapered section 1044 such that the detection circuit can effectively determine whether or not a downstream occlusion has occurred during rotation of the rotor 1040.

Upstream Occlusion Detection (End of Reservoir Detection)

As mentioned previously with reference to FIGS. 1-4, the fluid infusion device cooperates with a fluid cartridge module 104 having a fluid reservoir. The fluid reservoir has a fluid-tight plunger, piston, or stopper that is pulled up by the negative pressure created by the fluid pump mechanism during each fluid intake cycle. The negative pressure draws the medication fluid out of the fluid reservoir, through the inlet conduit, and into the fluid pump mechanism. If the piston gets stuck in the fluid reservoir, then the fluid pump mechanism will not be able to draw any fluid from the reservoir. This fault condition is known as an upstream occlusion because the fluid flow path leading into the fluid pump mechanism is effectively blocked. Similarly, if the fluid reservoir is empty, then the fluid pump mechanism will be pulling on a vacuum rather than drawing in fluid. This condition can also be considered an upstream occlusion because the patient will not be receiving the expected amount of medication fluid when the reservoir is empty.

The following sections relate to various techniques and technologies for detecting an empty fluid reservoir (also referred to as an upstream occlusion). These techniques are desirable to increase the safety of a medication infusion device. With particular reference to the fluid pump mechanism described here, end of reservoir detection can employ one or more of the following general methodologies, without limitation: (1) detecting that the stopper has reached an end position; (2) detecting that the fluid pump mechanism is pulling on a vacuum rather than drawing in fluid; (3) measurement of the stopper position over the length of the reservoir; and (4) observing axial displacement characteristics of the rotor relative to the stator.

Upstream Occlusion Detection: Methodology 1

Figure 32:
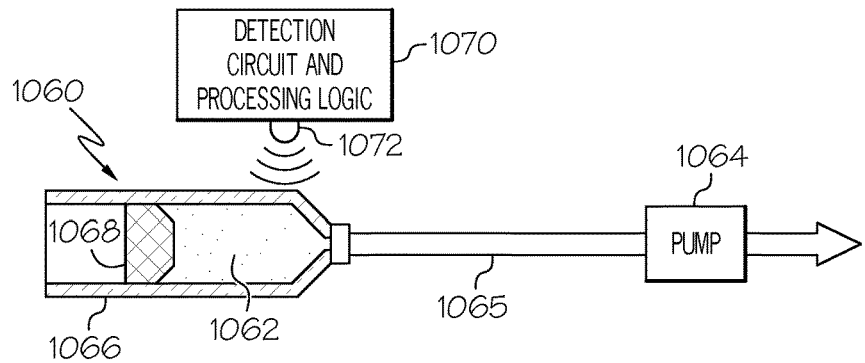
FIG. 32 is a simplified diagram of an exemplary embodiment of an end of reservoir detection system interrogating a fluid reservoir.
Figure 33:
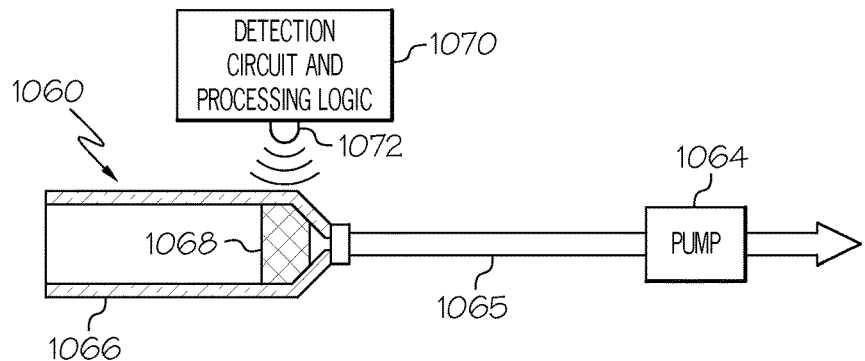
FIG. 33 is a simplified diagram of the end of reservoir detection system detecting an empty reservoir condition.

The upstream occlusion detection methodology presented in this section relies on a sensor that detects when the stopper of the fluid reservoir it at or near its end position. In this regard, FIG. 32 is a simplified diagram of an exemplary embodiment of an end of reservoir detection system interrogating a fluid reservoir 1060 at a time when medication fluid 1062 remains in the fluid reservoir 1060, and FIG. 33 is a simplified diagram of the system at a time when the fluid reservoir 1060 is empty. The fluid reservoir 1060 is coupled to a fluid pump mechanism 1064 via a conduit 1065. The fluid pump mechanism 1064 can be designed and configured as described above with reference to FIGS. 5-16.

The fluid reservoir 1060 includes a barrel 1066 and a stopper 1068 that creates a fluid tight seal with the inner wall of the barrel 1066. The stopper 1068 is shaped, sized, and configured to slide within the barrel 1066 as the medication fluid 1062 is drawn out. As explained above, the fluid pump mechanism 1064 creates negative pressure during each fluid intake cycle, and the negative pressure causes the medication fluid 1062 to enter the chamber of the fluid pump mechanism 1064. This action also causes the stopper 1068 to move (to the right in FIG. 32 and FIG. 33) within the barrel 1066.

The embodiment of the system shown in FIG. 32 and FIG. 33 includes a detection circuit 1070 that is suitably configured to interrogate, observe, or otherwise detect the position of the stopper 1068 as it approaches and/or reaches its end position (shown in FIG. 33). Accordingly, in certain embodiments the barrel 1066 is clear or translucent to accommodate the operation of the detection circuit 1070. The detection circuit 1070 can utilize one or more of the following sensing technologies, without limitation: optical; acoustical; imaging; ultrasound; infrared; or magnetic. The detection circuit 1070 can include an interrogation signal emitter 1072 that generates interrogation signals (acoustic, optical, magnetic, etc.) for purposes of determining when the stopper 1068 has reached its end position, which corresponds to the "end of reservoir" state. In some embodiments, the stopper 1068 can include an index feature that can be quickly and easily detected by the detection circuit 1070 when the stopper 1068 reaches its end position. Depending on the particular implementation, the index feature can be, without limitation: a visible marking; a physical feature such as an indentation; a colored region; an electrically, magnetically, or inductively detectable sensor element; or the like.

The detection circuit 1070 can take appropriate action when it determines that the stopper 1068 has reached the endpoint (or is near the endpoint). For example, the detection circuit 1070 can initiate an alert, an alarm, or a message intended for the user or a caregiver. Moreover, the detection circuit 1070 can be suitably configured to monitor the movement (or lack thereof) of the stopper 1068 during operation of the fluid pump mechanism 1064 to determine whether or not the stopper 1068 is traveling in an expected and ordinary manner in response to pumping cycles. In this regard, the detection circuit 1070 can be utilized to check whether or not the stopper 1068 is frozen in the barrel 1066, whether or not the movement of the stopper 1068 is impeded, or the like.

Upstream Occlusion Detection: Methodology 2

Figure 34:
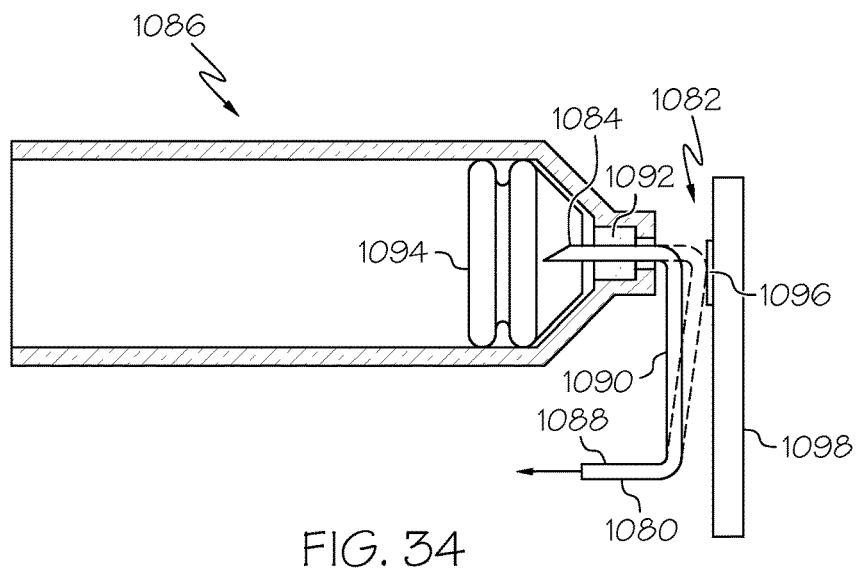
FIG. 34 is a simplified diagram of an exemplary embodiment of an end of reservoir detection system that implements a mechanical switch concept.

The upstream occlusion detection methodology presented in this section relies on a mechanical switch to detect when the stopper of the fluid reservoir it at or near its end position. In this regard, FIG. 34 is a simplified diagram of an exemplary embodiment of an end of reservoir detection system that implements a mechanical switch concept. The embodiment depicted in FIG. 34 employs an outlet conduit 1080 as one component of a switch 1082. The outlet conduit 1080 has an inlet end 1084 that cooperates with a fluid reservoir 1086, an outlet end 1088 in fluid communication with a fluid pump mechanism (not shown), and a switch contact section 1090 between the inlet end 1084 and the outlet end 1088. The fluid reservoir 1086 provides medication fluid to the fluid pump mechanism in the manner described in the previous section. The manner in which the fluid pump mechanism functions will not be redundantly described in detail here.

The inlet end 1084 of the outlet conduit 1080 is designed to penetrate a septum 1092 of the fluid reservoir 1086. The inlet end 1084 enters the barrel of the fluid reservoir 1086 to establish fluid communication with the medication fluid inside the barrel. As explained in the immediately preceding section, a stopper 1094 of the fluid reservoir 1086 is pulled toward the inlet end 1084 during pumping cycles. Eventually, the stopper 1094 reaches the end position shown in FIG. 34. At or near the end position, the stopper 1094 physically contacts the inlet end 1084 of the outlet conduit 1080, and continued movement of the stopper 1094 toward its end position causes the switch contact section 1090 of the outlet conduit 1080 to deflect toward a switch contact pad 1096. FIG. 34 depicts the deflected state of the switch contact section 1090 in dashed lines.

The switch contact pad 1096 can be mounted to a circuit board 1098 or any suitable structure. The switch contact section 1090 of the outlet conduit 1080 is formed from an electrically conductive material. The switch contact pad 1096 is also formed from an electrically conductive material. These two components cooperate to form a mechanical switch (for simplicity and clarity, the electrical connections and leads are not shown in FIG. 34). The circuit board 1098 may be utilized with a suitably designed detection circuit that detects when the switch contact section 1090 touches the switch contact pad 1096. In other words, the detection circuit detects whether the switch 1082 is open or closed. If the switch 1082 is open, the detection circuit determines that the fluid reservoir 1086 is not empty. Conversely, if the switch 1082 is closed, the detection circuit determines that the fluid reservoir 1086 is at the "end of reservoir" state. The detection circuit can take appropriate action when it detects closure of the switch 1082. For example, the detection circuit can initiate an "end of reservoir" alert, an alarm, or a message intended for the user or a caregiver.

Upstream Occlusion Detection: Methodology 3

Figure 35:
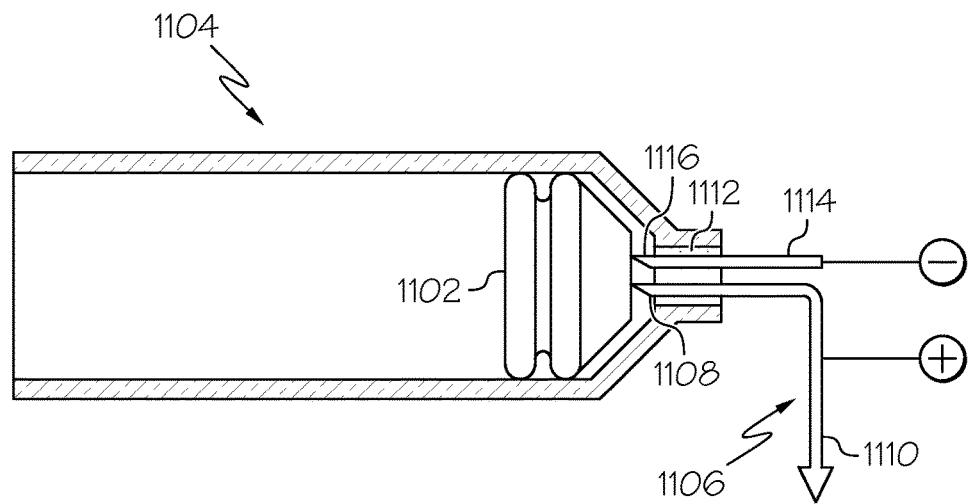
FIG. 35 is a simplified diagram of an exemplary embodiment of an end of reservoir detection system that utilizes a conductive fluid reservoir stopper (or a conductive element of a stopper)

The upstream occlusion detection methodology presented in this section employs an electrically conductive fluid reservoir stopper (or a stopper having an electrically conductive region). In this regard, FIG. 35 is a simplified diagram of an exemplary embodiment of an end of reservoir detection system that utilizes a conductive stopper 1102 of a fluid reservoir 1104. The fluid reservoir 1104 provides medication fluid to a fluid pump mechanism of the type described above. The manner in which the fluid pump mechanism functions and cooperates with the fluid reservoir 1104 will not be redundantly described in detail here.

The fluid infusion device includes an outlet conduit 1106 having an inlet end 1108 and an outlet end 1110. The inlet end 1108 is designed to penetrate a septum 1112 of the fluid reservoir 1104, and the outlet end 1110 is in fluid communication with the fluid pump mechanism. The inlet end 1108 enters the barrel of the fluid reservoir 1104 to establish fluid communication with the medication fluid inside the barrel. The fluid infusion device also includes an electrically conductive needle 1114. The needle 1114 has a contact end 1116 that is designed to penetrate the septum 1112 for entry into the barrel of the fluid reservoir 1104. The outlet conduit 1106 and the needle 1114 are electrically connected to a suitably configured detection circuit (not shown). For example, the needle 1114 can be connected to a negative voltage terminal and the outlet conduit 1106 can be connected to a positive voltage terminal (or vice versa).

As explained above, the stopper 1102 of the fluid reservoir 1104 travels toward the inlet end 1108 of the outlet conduit 1106 during pumping cycles. Eventually, the stopper 1102 reaches the end position (shown in FIG. 35) and makes contact with the inlet end 1108 of the outlet conduit 1106 and with the contact end 1116 of the needle 1114. Notably, the area of the stopper 1102 that makes contact with the outlet conduit 1106 and the needle 1114 is electrically conductive. In practice, the stopper 1102 can be fabricated from an electrically conductive material, or an electrically conductive film or patch can be affixed to the top of the stopper 1102. When the stopper 1102 reaches the end position shown in FIG. 35, the outlet conduit 1106 is shorted with the needle 1114. This action is akin to the closing of a switch (as described in the immediately preceding section), which can be monitored and detected by the detection circuit. Thus, if the fluid reservoir 1104 is not empty, the stopper 1102 will not create a short across the needle 1114 and the outlet conduit 1106. Conversely, when the stopper 1102 reaches its end position, the needle 1114 is shorted with the outlet conduit 1106 and the detection circuit determines that the fluid reservoir 1104 is at the "end of reservoir" state. The detection circuit can take appropriate action when it detects this state. For example, the detection circuit can initiate an "end of reservoir" alert, an alarm, or a message intended for the user or a caregiver.

Upstream Occlusion Detection: Methodology 4

Figure 36:
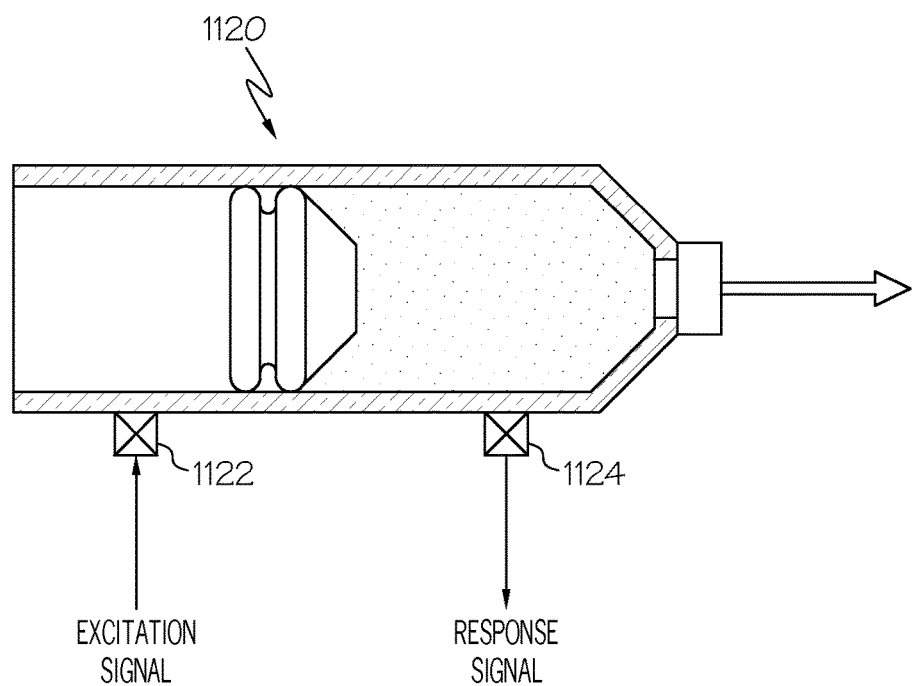
FIG. 36 is a simplified diagram of an exemplary embodiment of an end of reservoir detection system that applies an excitation signal to a fluid reservoir.

The upstream occlusion detection methodology presented in this section utilizes an excitation signal applied to the fluid reservoir to determine the volume of fluid remaining in the reservoir. In this regard, FIG. 36 is a simplified diagram of an exemplary embodiment of an end of reservoir detection system that can be used to analyze the condition of a fluid reservoir 1120 of the type described previously herein. The fluid reservoir 1120 provides medication fluid to a fluid pump mechanism of the type described above. The manner in which the fluid pump mechanism functions and cooperates with the fluid reservoir 1120 will not be redundantly described in detail here.

The fluid infusion device that hosts the fluid reservoir 1120 includes a suitably configured detection circuit (not shown) that includes, controls, or otherwise cooperates with an excitation signal generator 1122 and an associated sensor 1124. The excitation signal generator 1122 can be coupled to the fluid reservoir 1120 for purposes of applying an excitation signal to the fluid reservoir 1120. The excitation signal can be, for example, a vibration signal having a particular frequency or a particular frequency spectrum that is suitable for measuring the resonance or other response of the fluid reservoir 1120. The resonance of the fluid reservoir 1120 is influenced by the volume and/or mass of the fluid remaining in the fluid reservoir 1120. In practice, the resonance of the fluid reservoir 1120 can be empirically determined or otherwise characterized for purposes of programming the detection circuit. Accordingly, the detection circuit can obtain and analyze the response signal in an appropriate manner to determine whether or not the fluid reservoir 1120 is empty. If the response signal is indicative of an empty reservoir, the detection circuit can take appropriate action, e.g., initiate an "end of reservoir" alert, an alarm, or a message intended for the user or a caregiver.

Upstream Occlusion Detection: Methodology 5

Figure 37:
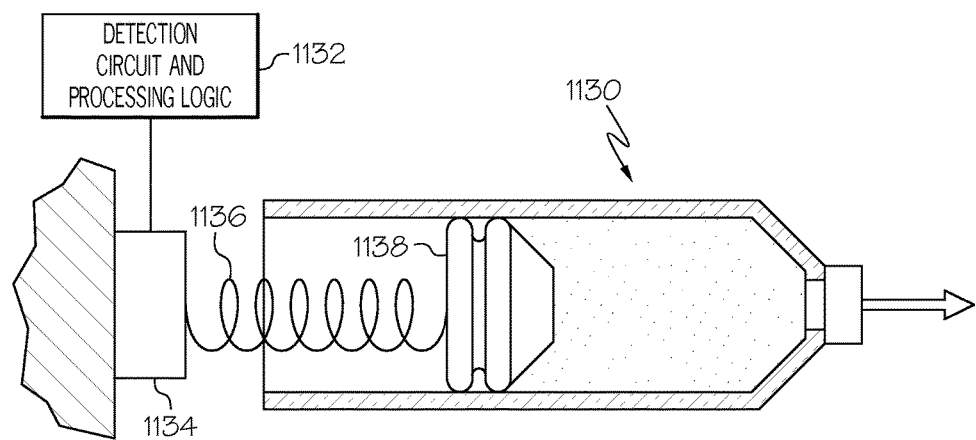
FIG. 37 is a simplified diagram of an exemplary embodiment of an end of reservoir detection system that uses a force sensor to determine the position of a stopper of a fluid reservoir.

The upstream occlusion detection methodology presented in this section uses a force sensor to measure the position of a fluid reservoir stopper. In this regard, FIG. 37 is a simplified diagram of an exemplary embodiment of an end of reservoir detection system for a fluid reservoir 1130 of a fluid infusion device. The fluid reservoir 1130 provides medication fluid to a fluid pump mechanism of the type described above. The manner in which the fluid pump mechanism functions and cooperates with the fluid reservoir 1130 will not be redundantly described in detail here.

The fluid infusion device that hosts the fluid reservoir 1120 includes a suitably configured detection circuit 1132 that includes, controls, or otherwise cooperates with a force sensor 1134. The force sensor 1134 can be configured as described above with reference to FIG. 28. The force sensor 1134 can be used to measure the force imparted by a biasing element 1136 (such as a spring) that is coupled to the stopper 1138 of the fluid reservoir 1130. The tension characteristics of the biasing element 1136 are selected such that the biasing element 1136 cannot independently move the stopper 1138. In other words, the force applied by the biasing element 1136 is too low to overcome the static friction of the stopper 1138, and the biasing element 1136 is not utilized to actuate the stopper 1138 or to otherwise deliver fluid from the fluid reservoir 1130. Rather, the stopper 1138 is designed to move only in response to the negative fluid pressure caused by the normal operation of the fluid pump mechanism, as described in detail above. Consequently, the biasing element 1136 is strictly utilized to provide a force measurement that corresponds to the position of the stopper 1138 within the fluid reservoir 1130.

The force measurements obtained or otherwise processed by the detection circuit 1132 vary in accordance with the position of the stopper 1138. When the fluid reservoir 1130 is full, the stopper 1138 is located at or near the base end of the fluid reservoir 1130 and, therefore, the spring force detected by the force sensor 1134 is relatively high. Conversely, when the fluid reservoir 1130 is empty, the stopper 1138 is located at its end position near the neck of the fluid reservoir 1130. When the stopper 1138 is at the end position, the spring force measured by the force sensor 1134 is relatively low. Accordingly, the detection circuit 1132 can obtain and analyze the output of the force sensor 1134 in an appropriate manner to determine whether or not the fluid reservoir 1130 is empty. If the measured force is indicative of an empty reservoir, the detection circuit 1132 can take appropriate action, e.g., initiate an "end of reservoir" alert, an alarm, or a message intended for the user or a caregiver.

Upstream Occlusion Detection: Methodology 6

Figure 38:
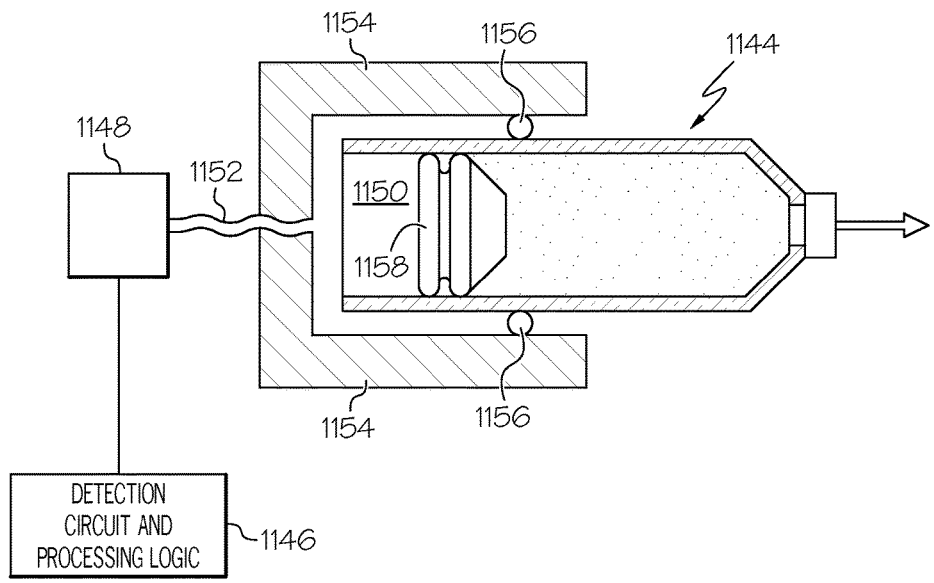
FIG. 38 is a simplified diagram of an exemplary embodiment of an end of reservoir detection system that uses a pressure sensor to determine the position of a stopper of a fluid reservoir.

The upstream occlusion detection methodology presented in this section uses a pressure sensor to measure the position of a fluid reservoir stopper. In this regard, FIG. 38 is a simplified diagram of an exemplary embodiment of an end of reservoir detection system for a fluid reservoir 1144 of a fluid infusion device. The fluid reservoir 1144 provides medication fluid to a fluid pump mechanism of the type described above. The manner in which the fluid pump mechanism functions and cooperates with the fluid reservoir 1144 will not be redundantly described in detail here.

The fluid infusion device that hosts the fluid reservoir 1144 includes a suitably configured detection circuit 1146 that includes, controls, or otherwise cooperates with a pressure sensor 1148. The pressure sensor 1148 is designed to detect slight changes in the pressure of a sealed volume 1150 that is associated with the fluid reservoir 1144. In this regard, FIG. 38 schematically depicts a vent 1152 leading from the sealed volume 1150 to the pressure sensor 1148. The vent 1152 allows the pressure sensor 1148 to monitor the pressure inside the sealed volume 1150 during operation of the fluid infusion device.

The sealed volume 1150 can be defined by suitably configured structure of the fluid infusion device. The illustrated embodiment, which is merely one possible implementation, includes a wall structure 1154 that at least partially surrounds the base of the fluid reservoir 1144. An airtight sealing element 1156 (such as an o-ring or a gasket) can be used to seal the wall structure 1154 against the outer surface of the fluid reservoir 1144. It should be appreciated that the sealed volume 1150 can be defined in any appropriate way, using additional structures or components if so desired. Moreover, the shape and size of the sealed volume 1150 can vary from one embodiment to another.

The pressure measurements obtained or otherwise processed by the detection circuit 1146 vary in accordance with the position of the stopper 1158 of the fluid reservoir 1144. In practice, the system is designed and configured such that the sealed volume 1150 does not adversely influence the normal operation of the fluid infusion device. For example, the sealed volume 1150 should not impede the movement of the stopper 1158, which is caused by fluid intake strokes of the fluid pump mechanism.

When the fluid reservoir 1144 is full, the stopper 1158 is located at or near the base end of the fluid reservoir 1144 and, therefore, the sealed volume 1150 is relatively small. Consequently, the pressure obtained from the pressure sensor 1148 will be relatively high. Conversely, when the fluid reservoir 1144 is empty, the stopper 1158 is located at its end position near the neck of the fluid reservoir 1144. When the stopper 1158 is at the end position, the sealed volume 1150 is relatively large and, therefore, the pressure obtained from the pressure sensor 1148 will be relatively low. Accordingly, the detection circuit 1146 can obtain and analyze the output of the pressure sensor 1148 in an appropriate manner to determine whether or not the fluid reservoir 1144 is empty. If the measured pressure of the sealed volume 1150 is indicative of an empty reservoir, the detection circuit 1146 can take appropriate action, e.g., initiate an "end of reservoir" alert, an alarm, or a message intended for the user or a caregiver.

Upstream Occlusion Detection: Methodology 7

Figure 39:
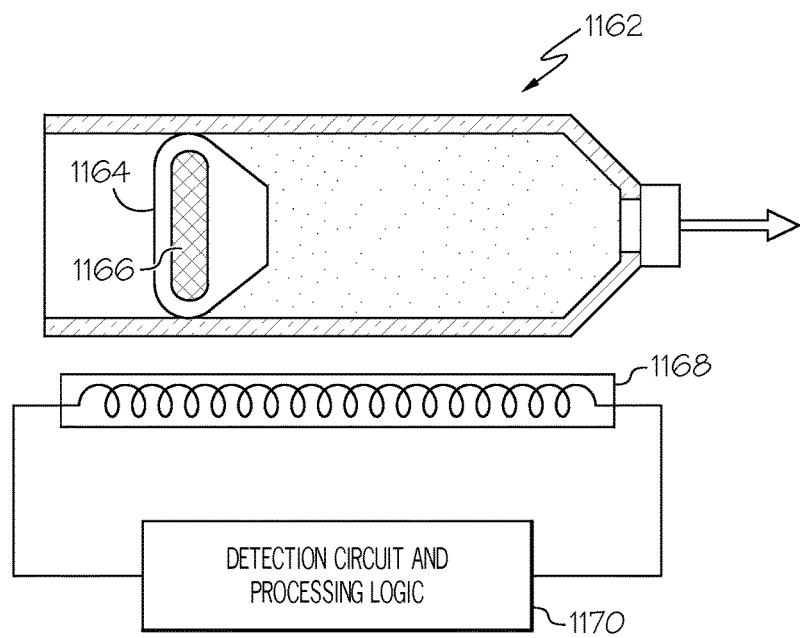
FIG. 39 is a simplified diagram of an exemplary embodiment of an end of reservoir detection system that measures an inductance to determine the position of a stopper of a fluid reservoir.

The upstream occlusion detection methodology presented in this section measures an inductance to determine the position of a fluid reservoir stopper. In this regard, FIG. 39 is a simplified diagram of an exemplary embodiment of an end of reservoir detection system for a fluid reservoir 1162 of a fluid infusion device. The fluid reservoir 1162 provides medication fluid to a fluid pump mechanism of the type described above. The manner in which the fluid pump mechanism functions and cooperates with the fluid reservoir 1162 will not be redundantly described in detail here.

The fluid reservoir 1162 is provided with a stopper 1164 having an electrically conductive target 1166 integrated therein (or affixed thereto). Although the target 1166 is shown in FIG. 39, it can instead be incorporated into the body of the stopper 1164 and, therefore, be hidden from view. The shape, size, and configuration of the target 1166 can differ from that shown in FIG. 39, which merely shows the target 1166 in schematic form. The target 1166 cooperates with an electrically conductive coil element 1168 that resides outside of, but in close proximity to, the fluid reservoir 1162. The fluid infusion device that hosts the fluid reservoir 1162 includes a suitably configured detection circuit 1170 that includes, controls, or otherwise communicates with the coil element 1168. More specifically, the detection circuit 1170 is connected to the terminals of the coil element 1168 such that the detection circuit 1170 can monitor and measure the electrical inductance of the coil element 1168 during operation of the fluid infusion device.

The target 1166 and the coil element 1168 are suitably configured such that the inductance of the coil element 1168 varies (in a measurable manner) as a function of the position of the stopper 1164. Accordingly, the detection circuit 1170 observes a variable inductance as the stopper 1164 travels from the base of the fluid reservoir 1162 to the end position. The measured inductance can be correlated to the position of the stopper 1164, and the inductance corresponding to the end position of the stopper 1164 can be characterized for purposes of detecting the end of reservoir state. If the measured inductance of the coil element 1168 is indicative of an empty reservoir, the detection circuit 1170 can take appropriate action, e.g., initiate an "end of reservoir" alert, an alarm, or a message intended for the user or a caregiver.

Upstream Occlusion Detection: Methodology 8

Figure 40:
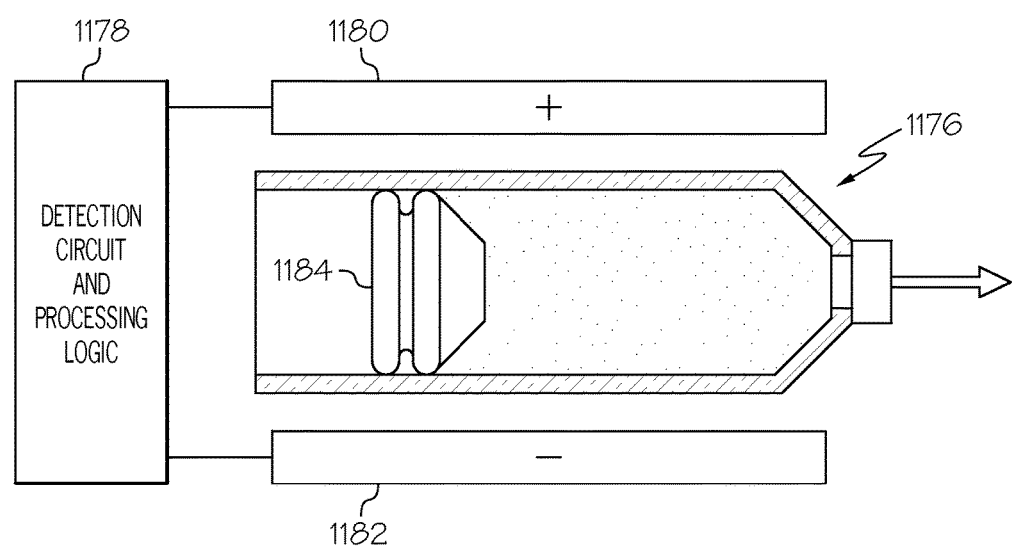
FIG. 40 is a simplified diagram of an exemplary embodiment of an end of reservoir detection system that measures a capacitance to determine the position of a stopper of a fluid reservoir.

The upstream occlusion detection methodology presented in this section measures a capacitance to determine the position of a fluid reservoir stopper. In this regard, FIG. 40 is a simplified diagram of an exemplary embodiment of an end of reservoir detection system for a fluid reservoir 1176 of a fluid infusion device. The fluid reservoir 1176 provides medication fluid to a fluid pump mechanism of the type described above. The manner in which the fluid pump mechanism functions and cooperates with the fluid reservoir 1176 will not be redundantly described in detail here.

The system described here employs a detection circuit 1178 to measure the capacitance between a first capacitor electrode 1180 and a second capacitor electrode 1182. Notably, the capacitance measured by the detection circuit 1178 is a function of the amount of fluid remaining in the fluid reservoir 1176. Consequently, the capacitance measured by the detection circuit 1178 is also a function of the position of the stopper 1184 of the fluid reservoir 1176.

FIG. 40 schematically depicts the electrodes 1180, 1182 for purposes of this description. In practice, the electrodes 1180, 1182 can be integrated into or attached to the barrel of the fluid reservoir 1176 in a way that accommodates electrical coupling to the detection circuit 1178. In certain embodiments, the electrodes 1180, 1182 are located on a structure (such as a circuit board) that is held in close proximity to the installed location of the fluid reservoir 1176. The electrodes 1180, 1182 can be realized as conductive traces, metallic films, or the like.

The detection circuit 1178 is connected to the electrodes 1180, 1182 such that the detection circuit 1178 can monitor and measure the capacitance between the electrodes 1180, 1182 during operation of the fluid infusion device. As the fluid gets depleted from the fluid reservoir 1176, the capacitance between the electrodes 1180, 1182 varies (in a detectable manner), due to the changing dielectric properties of the fluid reservoir 1176. Accordingly, the detection circuit 1178 observes a variable capacitance as the fluid exits the fluid reservoir 1176. The measured capacitance can be correlated to the position of the stopper 1184 and/or to the amount of fluid remaining in the fluid reservoir 1176, and the capacitance corresponding to the end position of the stopper 1184 can be characterized for purposes of detecting the end of reservoir state. If the measured capacitance is indicative of an empty reservoir, the detection circuit 1178 can take appropriate action, e.g., initiate an "end of reservoir" alert, an alarm, or a message intended for the user or a caregiver.

Upstream Occlusion Detection: Methodology 9

Figure 41:
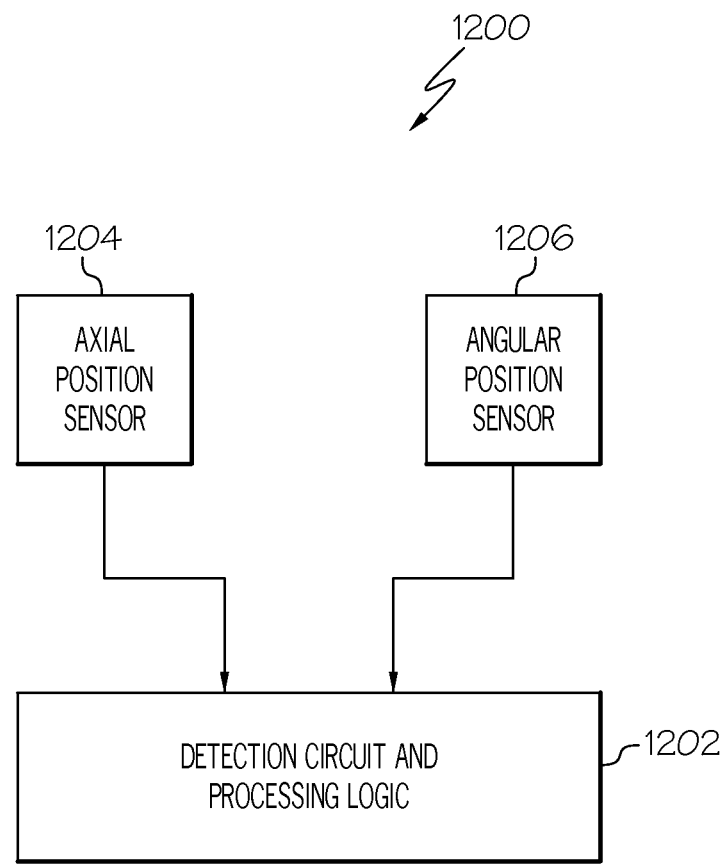
FIG. 41 is a schematic block diagram of an exemplary embodiment of an end of reservoir detection system that measures axial velocity of a rotor of a fluid pump mechanism.

The upstream occlusion detection methodology presented in this section assumes that the fluid infusion device uses a fluid pump mechanism of the type described above. The methodology measures or calculates the axial velocity of the rotor as it travels during the fluid expulsion cycle and determines whether or not an upstream occlusion (e.g., the end of the fluid reservoir) as occurred. In this regard, FIG. 41 is a schematic block diagram of an exemplary embodiment of an end of reservoir detection system 1200 that can be implemented in a fluid infusion device having a rotary fluid pump mechanism. For the sake of clarity and simplicity, the fluid pump mechanism and the fluid reservoir are not shown in FIG. 41. Moreover, the manner in which the fluid pump mechanism functions and cooperates with the fluid reservoir will not be redundantly described in detail here.

The system 1200 includes, without limitation: a detection circuit 1202; an axial position sensor 1204 (or sensing system); and an angular position sensor 1206 (or sensing system). The axial position sensor 1204 is designed and configured to obtain axial position data of the rotor, where the axial position data indicates the axial position or displacement of the rotor during operation of the fluid pump mechanism. The operating principle of the axial position sensor 1204 may vary from one embodiment to another. In this regard, the axial position sensor 1204 can leverage any of the position detection techniques and methodologies described herein, including any of those previously described with reference to FIGS. 22-31, without limitation. The angular position sensor 1206 is designed and configured to obtain angular position data of the rotor, where the angular position data indicates the rotational position of the rotor, relative to any convenient reference point. In practice, the angular position of the rotor can be expressed in degrees or in any appropriate units that correspond to angular measurement. In certain embodiments, the angular position sensor 1206 may be realized as a digital encoder or counter that monitors the operation of the drive motor, which in turn rotates the rotor.

Regardless of the manner in which the axial position sensor 1204 and the angular position sensor 1206 are implemented, the respective sensor data or information is obtained by the detection circuit 1202 for processing and analysis. More specifically, the detection circuit 1202 can process the sensor data to determine whether or not an occlusion upstream of the fluid pump mechanism has occurred. The determination is based on certain detectable characteristics of the sensor data, wherein the detection circuit 1202 can determine whether the fluid pump mechanism is operating as expected to draw fluid in from the fluid reservoir and expel the fluid for delivery to the patient, or whether an upstream occlusion is preventing the fluid pump mechanism from drawing in fluid. As mentioned previously, an upstream occlusion may be detected when an inlet fluid flow path is blocked, or when the fluid reservoir is empty (and the stopper of the reservoir has reached its end position).

The detection circuit 1202 calculates or otherwise obtains the axial velocity of the rotor during the fluid expulsion cycle. Referring again to FIG. 15, the section 820 of the plot represents the fluid expulsion period, during which the rotor normally "snaps back" into the stator under the force of the biasing element. The velocity of the rotor during this period can be characterized and predicted under normal and expected operating conditions. It should be understood that the slope of the section 820 is indicative of the axial velocity of the rotor (a gradual slope corresponds to lower velocity, and a steeper slope corresponds to higher velocity). If an upstream occlusion is present (e.g., the fluid reservoir is empty and the stopper of the reservoir has reached its end position), then the fluid pump mechanism will pull on a vacuum. Consequently, during the fluid intake period (corresponding to the section 816 of the plot in FIG. 15) the vacuum creates additional force in the same direction of the biasing force. This additional force increases the axial velocity of the rotor during the fluid expulsion cycle.

Figure 42:
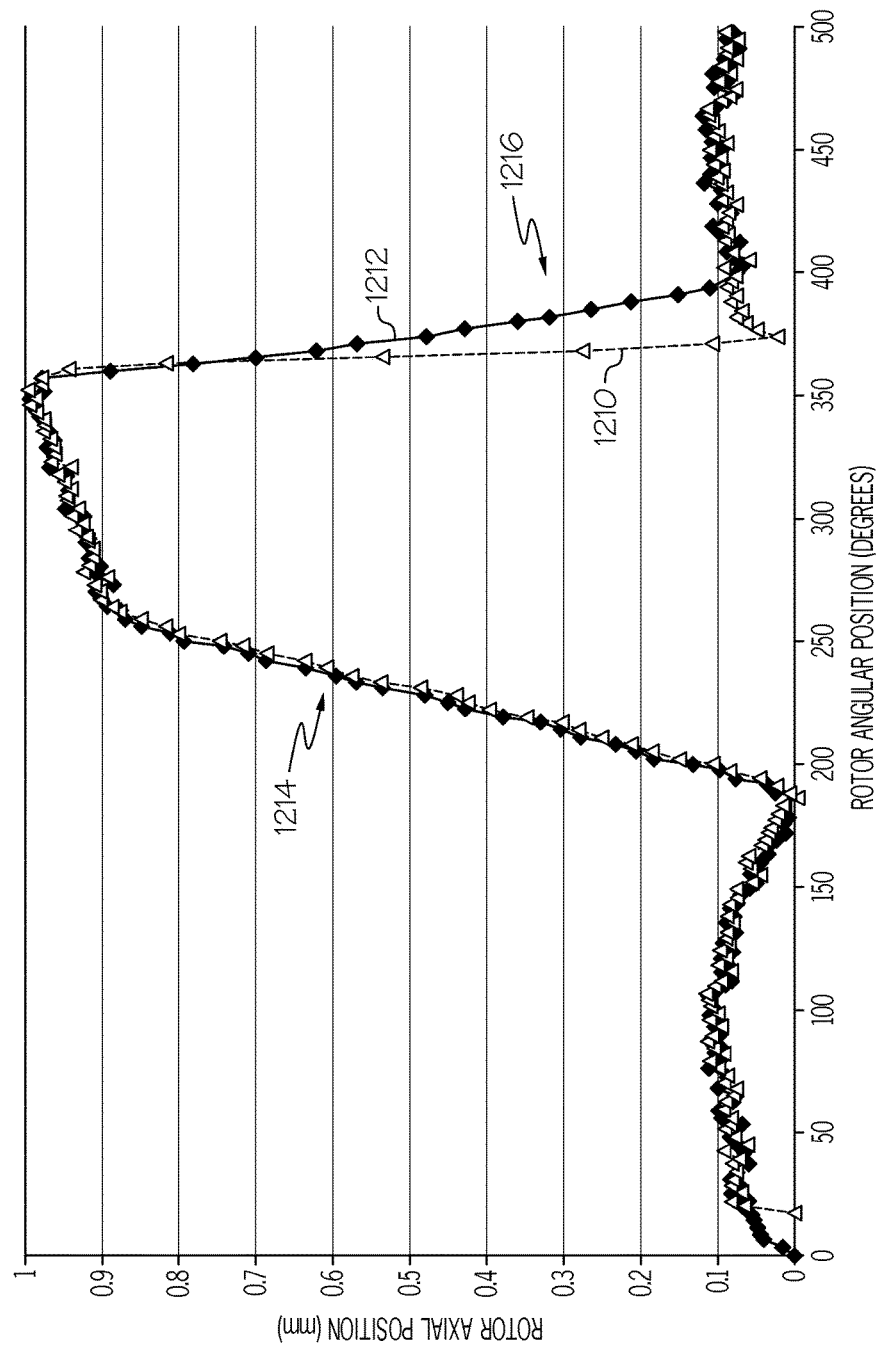
FIG. 42 is a graph that includes a plot of rotor axial position versus rotor angular position for an upstream occlusion condition.

FIG. 42 is a graph that includes a plot 1210 of rotor axial position versus rotor angular position for an upstream occlusion condition. FIG. 42 also includes a plot 1212 that corresponds to the normal and expected operating condition in the absence of any occlusion. As FIG. 42 demonstrates, the two plots 1210, 1212 exhibit roughly the same characteristics during the fluid intake period 1214 of the pumping cycle. During the fluid expulsion period 1216 of the pumping cycle, however, the two plots 1210, 1212 deviate from one another. As explained above, the plot 1212 is characterized by a more gradual slope during the expulsion period 1216; this gradual slope is indicative of a nominal axial velocity of the rotor. In contrast, the plot 1210 is characterized by a steeper slope during the expulsion period 1216. The steeper slope is indicative of higher axial velocity of the rotor during this time. Again, the vacuum conditions created by an occlusion upstream of the fluid pump mechanism increase the axial velocity of the rotor during the fluid expulsion period (relative to the nominal axial velocity experienced during normal fluid delivery operations).

The detection circuit 1202 is suitably configured and programmed to analyze the collected axial position and angular position sensor data in a way that is consistent with the comparison visualized in FIG. 42. For example, the detection circuit 1202 can calculate an average or maximum rotor axial velocity during the fluid expulsion period and compare the calculated velocity to a predetermined threshold axial velocity value. If the calculated axial velocity exceeds the threshold value, then the detection circuit 1202 can declare that an upstream occlusion has been detected. Notably, the detection circuit 1202 can consider the angular position data to determine the timing of the pumping cycle, such that the axial velocity of the rotor is analyzed during the fluid expulsion phase of the cycle (rather than at other times). The detection circuit 1202 can be programmed as needed to accurately characterize the axial velocity behavior of the rotor during the fluid expulsion period. In this regard, under normal operating conditions the fluid expulsion period is characterized by a nominal axial velocity of the rotor, and under upstream occlusion conditions the fluid expulsion period is characterized by a different axial velocity of the rotor, which is higher than the nominal axial velocity of the rotor.

It should be appreciated that the detection circuit 1202 can make its determination using any suitable methodology or algorithm. For example, the detection circuit 1202 can determine the axial position of the rotor as a function of the angular rotation of the rotor, calculate the slope of the response (similar to that depicted in FIG. 42), and compare the calculated slope against a predetermined threshold slope value. In alternative embodiments, the detection circuit 1202 can leverage accelerometer data to directly measure the velocity of the rotor as it moves toward the stator during the fluid expulsion period, and compare the measured velocity against a threshold value. These and other techniques are contemplated by this disclosure.

Upstream Occlusion Detection: Methodology 10

The upstream occlusion detection methodology presented in this section assumes that the fluid infusion device uses a fluid pump mechanism of the type described above, i.e., one having a stator and a cooperating rotor driven by a drive motor. The upstream occlusion detection methodology presented in this section analyzes the motor current of the drive motor to determine the operating condition or state of the fluid infusion device. Referring again to FIG. 15, one pumping cycle includes a fluid intake period (represented by the section 816 of the plot), a brief dwell period (represented by the section 818 of the plot), a fluid expulsion period (represented by the section 820 of the plot), and another dwell period (represented by the section 822 of the plot). As explained above with reference to FIGS. 5-15: the rotor cam element 722 travels along the stator cam element 706 during the fluid intake period and during the dwell period corresponding to the section 818 of the plot; the rotor cam element 722 disengages from the stator cam element 706 and moves toward the reference surface 736 during the fluid expulsion period; and the rotor cam element 722 travels along the reference surface 736 during the dwell period corresponding to the section 822 of the plot. Continued rotation of the rotor results in repetition of this pumping cycle.

The methodology described in this section assumes that the drive motor 138 is a DC motor, and that the current consumption of the drive motor 138 can be monitored and measured as it drives the rotor. It is well established that the current consumption of a DC motor is proportional to the output torque and the rotational speed (as torque increases, the current draw increases and the rotational speed decreases). Thus, when the rotor cam element 722 is traveling on the reference surface 736 and the applied biasing force is lower (the sections 814, 822 of the plot in FIG. 15), the motor current is somewhat stable, flat, and relatively low. In contrast, when the rotor cam element 722 is engaged with the stator cam element 706, the biasing spring force increases, which in turn increases the friction between the cam elements. The net effect is an increase in drive current consumption and torque output from the drive motor. The drive current peaks when the rotor cam element 722 reaches the plateau of the stator cam element 706, and then gradually decreases as the rotor cam element 722 continues traveling across the plateau. After the rotor cam element 722 disengages from the stator cam element 706 (i.e., the rotor cam element 722 falls off the plateau), the drive current returns to its relatively low and stable baseline level.

The fluid infusion device can include a suitably configured detection circuit that monitors and analyzes the current of the drive motor. The current can be analyzed as a function of time, angular position of the rotor, motor position, or the like. The detection circuit can compare the measured motor current against saved current profiles or response curves to determine whether the fluid pump mechanism is operating in a normal and expected manner, whether an upstream occlusion has occurred, whether a downstream occlusion has occurred, or the like. For example, if the fluid reservoir is empty (or if the upstream fluid flow path is blocked), then the motor current will exhibit measurably different characteristics than that described above. In this regard, the vacuum created by an empty reservoir or an upstream occlusion will increase the output torque during the fluid intake period (because the drive motor 138 must overcome the force created by the vacuum). Thus, the measured motor current will exhibit a steeper rise and a higher maximum value during the fluid intake period, relative to the normal motor current characteristics associated with non-occluded operation of the fluid pump mechanism. The detection circuit can be designed to take appropriate action if it observes this type of characteristic difference in the measured motor current. It should be appreciated that the methodology presented in this section can also be utilized to detect the presence of downstream occlusions if so desired.

Upstream Occlusion Detection: Methodology 11

The occlusion detection methodology presented in this section assumes that the fluid infusion device uses a fluid pump mechanism of the type generally described above with reference to FIGS. 5-14. The timing related to the opening and closing of the valves, however, is slightly different to accommodate occlusion detection. Consequently, the plots depicted in FIG. 15 and FIG. 16 do not apply to the embodiments presented here. Moreover, at least one of the embodiments presented in this section can be utilized for downstream occlusion detection in addition to (or in lieu of) upstream occlusion detection.

The embodiment previously described with reference to FIG. 15 employs valve timing such that the second valve (i.e., the outlet valve) opens when the stator cam element disengages the rotor cam element, or immediately before the stator cam element disengages the rotor cam element. In other words, the angular position of the trailing end of the rotor cam element corresponds to the right end of the section 818 of the plot shown in FIG. 15. Consequently, both valves remain closed during most of the section 818, and the second valve opens in conjunction with the stator cam element disengaging the rotor cam element.

Figure 43:
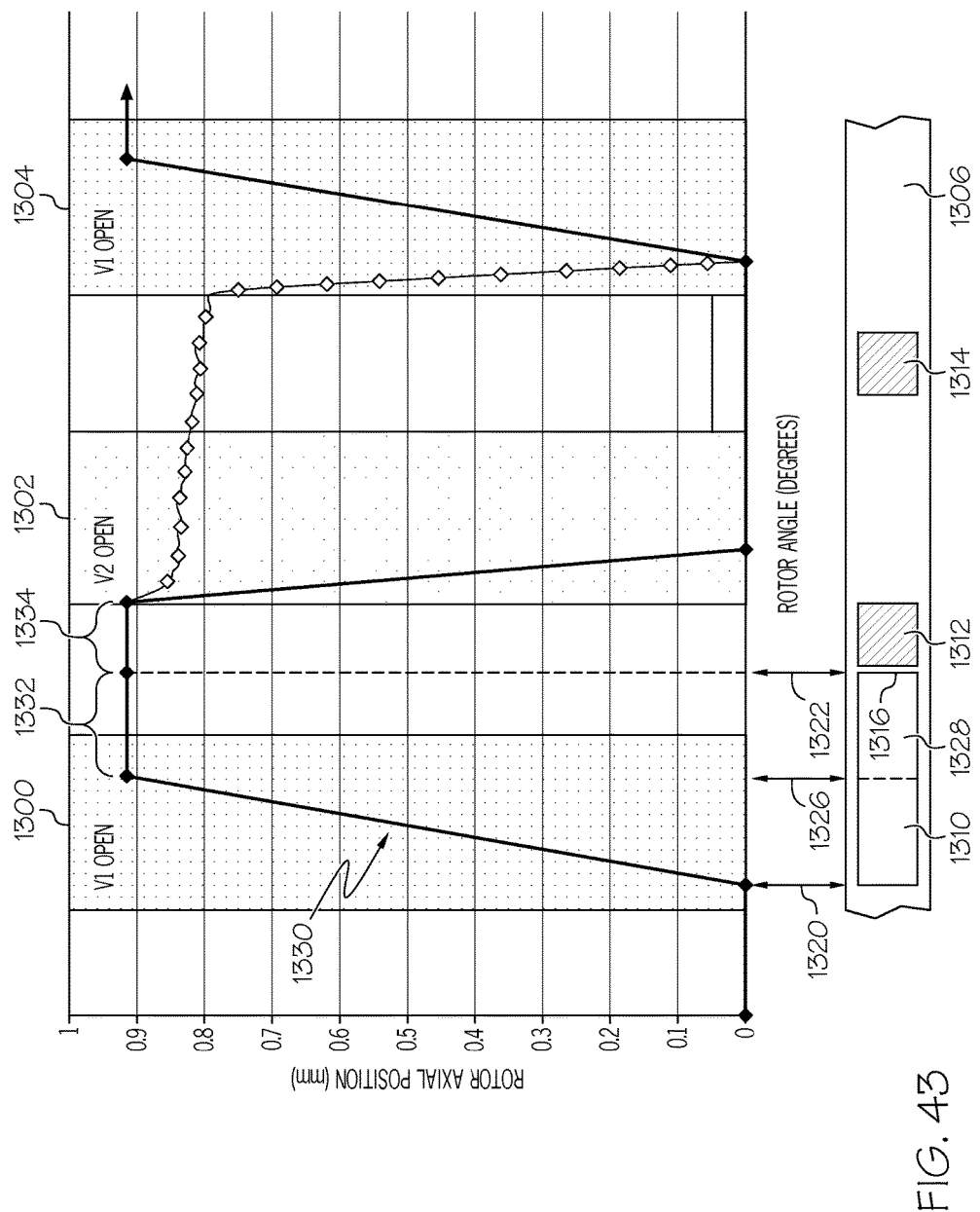
FIG. 43 is a graph that includes plots of rotor axial position versus rotor angular position for various operating conditions of a fluid pump mechanism.

In contrast to the previously described valve timing, the embodiments described in this section utilize a modified valve timing that delays the opening of the second valve. In this regard, FIG. 43 is a graph that includes plots of rotor axial position versus rotor angular position for various operating conditions of a fluid pump mechanism. In FIG. 43, a region 1300 corresponds to a first period during which the first/inlet valve (V1) is open and the second/outlet valve (V2) is closed, the region 1302 corresponds to a second period during which V1 is closed and V2 is open, and the region 1304 corresponds to a third period during which V1 is open and V2 is closed. The gaps between these regions correspond to periods during which both valves are closed.

FIG. 43 also schematically depicts the reference surface 1306 of a rotor 1308; the reference surface 1306 is rendered in a straight line (rather than a circle as depicted in FIG. 44) aligned with the rotor angle axis of the graph. For ease of illustration, FIG. 44 does not depict the endcap or surrounding structure of the rotor 1308. The rotor 1308 includes a rotor cam element 1310 having a variable height that rises from the reference surface 1306, as described in detail above with reference to FIGS. 11-14. The illustrated embodiment of the rotor 1308 also includes a first (leading) sensor contact element 1312 located on or integrated with the reference surface 1306, and a second (trailing) sensor contact element 1314 located on or integrated with the reference surface 1306. As will become apparent from the following description, the second sensor contact element 1314 is utilized to support downstream occlusion detection.

The first sensor contact element 1312 is located in a region that is unoccupied by the rotor cam element 1310. More specifically, the first sensor contact element 1312 is located at an angular position that follows the upper (trailing) edge 1316 of the rotor cam element 1310. As shown in FIG. 44, the first sensor contact element 1312 can be positioned on the reference surface 1306 immediately following the rotor cam element 1310. The second sensor contact element 1314 is also located in a region that is unoccupied by the rotor cam element 1310. The second sensor contact element 1314 is located at an angular position that follows the first sensor contact element 1312. As shown in FIG. 43 and FIG. 44, the first and second sensor contact elements 1312, 1314 are separated by a gap having a size that is dictated by the desired valve timing characteristics and the desired occlusion detection functionality.

Referring again to FIG. 43, the angular position 1320 corresponds to the lower (leading) edge 1322 of the rotor cam element 1310, and the angular position 1324 corresponds to the upper (trailing) edge 1316 of the rotor cam element 1310. The angular position 1326 corresponds to the beginning of the plateau 1328 of the rotor cam element 1310, i.e., the flat and highest section of the rotor cam element 1310. Accordingly, the section 1330 of the plot corresponds to the fluid intake period of the fluid pump mechanism, and the section 1332 of the plot corresponds to a dwell period during which the stator cam element resides on the plateau 1328 of the rotor cam element 1310. The right end of the section 1332 corresponds to the upper (trailing) edge 1316 of the rotor cam element 1310. Notably, the rotor cam element 1310 disengages the stator cam element at a time when both the inlet valve and the outlet valve are closed, and both valves remain closed for a short time thereafter. This brief "valve delay" period is represented by the section 1334 of the plot. The valve delay period corresponds to a time (or an angle of rotation) that begins with the end of the rotor cam element 1310 and ends with the opening of the outlet valve.

The angular positioning of the first sensor contact element 1312 on the rotor 1308 corresponds to a valve state that occurs after the inlet valve closes for a current pumping cycle, and before the outlet valve opens for the current pumping cycle. FIG. 43 schematically illustrates this feature—the rotor angle associated with the position of the first sensor contact element 1312 corresponds to a period during which both of the valves are closed. In contrast, the angular positioning of the second sensor contact element 1314 on the rotor 1308 corresponds to a different valve state that occurs after the outlet valve closes for the current pumping cycle, and before the inlet valve opens for a next pumping cycle.

The sensor contact elements 1312, 1314 cooperate with a suitably configured sensing element or arrangement and a detection circuit, which detects when the sensing element makes contact with the sensor contact elements 1312, 1312. The sensing element and related features and functionality described above with reference to FIGS. 18 and 19 can also be utilized with the embodiment described here. As explained above, a sensing element on the stator can be utilized to determine whether or not the stator cam element makes contact with the first sensor contact element 1312, the second sensor contact element 1314, or both. In this way, the detection circuit can monitor the characteristics of a detection signal obtained from the sensing element in response to the angular position of the rotor to determine a current operating condition of the fluid pump mechanism. For example, the sense pattern observed by the detection circuit may be indicative of normal operating conditions or a fault condition (such as a downstream occlusion, an upstream occlusion, an empty fluid reservoir, or the like). If the detection circuit detects a fault condition, then it can initiate or generate an alert, an alarm, a warning message, or take any appropriate type of action.

The solid plot in FIG. 43 corresponds to the behavior of the fluid pump mechanism under normal and expected operating conditions. Under these normal operating conditions, both valves remain closed for the period represented by the section 1334 of the plot. During this period, the axial position of the rotor remains substantially stable (at or near its highest point) even though the stator cam element has disengaged the rotor cam element. The closed state of the output valve and the presence of fluid in the fluid pump mechanism inhibits axial displacement of the rotor during this period. As soon as the output valve opens, however, the rotor is urged toward the stator until it reaches the nominal baseline position.

The dashed line plot in FIG. 43 corresponds to the behavior of the fluid pump mechanism under upstream occlusion conditions, which may be caused by a fluid line blockage upstream of the inlet valve or an empty fluid reservoir. In the presence of an upstream occlusion, the fluid pump mechanism pulls on a vacuum without drawing in fluid. The vacuum conditions created by the upstream occlusion create negative pressure, which allows the rotor cam element 1310 to move toward the reference surface 1306 even though the outlet valve is closed. This negative pressure causes the rotor to snap back into place as soon as the stator cam element disengages the rotor cam element (even though both valves are closed). Thus, the axial displacement of the rotor quickly decreases and reaches its nominal baseline level. The valve delay period associated with the section 1334 of the plot can be engineered as needed to accommodate upstream occlusion detection, as described in more detail below. The axial displacement of the rotor remains at the baseline level until the next fluid intake cycle.

The dotted line plot in FIG. 43 corresponds to the behavior of the fluid pump mechanism under downstream occlusion conditions, which may be caused by a fluid line blockage downstream of the outlet valve. In the presence of a downstream occlusion, the fluid pump mechanism cannot expel fluid as usual. Consequently, the axial displacement of the rotor remains relatively high until the inlet valve opens to accommodate backflow. Shortly thereafter, however, the next fluid intake cycle causes the axial displacement to increase again. Notably, the axial displacement of the rotor remains at or near its highest level even during the period represented by the section 1334 of the plot. During this period, the axial position of the rotor remains substantially stable (at or near its highest point) even though the stator cam element has disengaged the rotor cam element.

The behavior of the fluid pump mechanism under normal and occluded conditions can be characterized such that the sensor contact elements 1312, 1314 can be sized and positioned in an appropriate manner. For example, under normal operating conditions, the sensing element on the stator cam element makes no contact with the first sensor contact element 1312 because the rotor remains axially displaced from the stator throughout the angular position that corresponds to the location of the first sensor contact element 1312 on the reference surface 1306. Moreover, under normal operating conditions, the sensing element contacts the second sensor contact element 1314 once per pumping cycle because the rotor resides at its baseline axial position throughout the angular position that corresponds to the location of the second sensor contact element 1314 on the reference surface 1306. Accordingly, under normal operating conditions, the detection circuit will detect contact with only the second sensor contact element 1314 for each pumping cycle.

Under upstream occlusion conditions (including an end of reservoir state or a condition where the reservoir stopper has seized), the sensing element contacts both sensor contact elements 1312, 1314 once per pumping cycle. More specifically, the sensing element contacts the first sensor contact element 1312 shortly after the rotor cam element 1310 disengages the stator cam element (and at a time when both valves are closed) and, thereafter, the sensing element contacts the second sensor contact element 1314. The detection circuit can determine or declare that an upstream occlusion has occurred based on the sensing element contacting the first and second sensor contact elements 1312, 1314. Alternatively, the detection circuit can determine or declare that an upstream occlusion has occurred based on the sensing element contacting the first sensor contact element 1312 alone. Indeed, the second sensor contact element 1314 need not be employed for purposes of upstream occlusion detection.

Under downstream occlusion conditions, the sensing element makes no contact with either of the sensor contact elements 1312, 1314. Rather, the downstream occlusion prevents the stator cam element from reaching the reference surface 1306 of the rotor in the angular position range of the sensor contact elements 1312, 1314. As shown in FIG. 43, when the downstream fluid path is blocked, the sensing element does not reach the reference surface 1306 (if at all) until shortly after the outlet valve opens. Accordingly, the detection circuit can determine or declare that a downstream occlusion has occurred based on the sensing element making no contact with the sensor contact elements 1312, 1314.

In practice, the detection circuit described in this section can be designed to observe signal characteristics that result from interaction between the sensing element and the sensor contact elements 1312, 1314. In this regard, a different signal pattern will be generated for each revolution of the rotor, which corresponds to one pumping cycle. The detection circuit can monitor the obtained sensor signal pattern to determine the current operating condition/state of the fluid pump mechanism. For the embodiment presented in this section, a detected pattern of S1=LOW+S2=HIGH indicates normal operation (where S1 is the state of the first sensor contact element 1314 and S2 is the state of the second sensor contact element). A detected pattern of S1=HIGH+S2=HIGH indicates an upstream occlusion condition, and a detected pattern of S1=LOW+S2=LOW indicates a downstream occlusion condition. Alternatively, the detection circuit can simply count the number of detected "hits" during each rotation of the rotor 1308, without necessarily keeping track of which sensor contact element 1312, 1314 was contacted: only one count indicates normal operation; two counts indicates an upstream occlusion; and zero counts indicates a downstream occlusion. This simple encoding scheme makes it easy for the detection circuit to distinguish the three operating conditions of interest.

For the embodiment depicted in FIG. 44, the sensor contact elements 1312, 1314 are located on the reference surface 1306 of the rotor 1308. Moreover, the embodiment of FIG. 44 cooperates with a sensing element incorporated into the stator cam element (of the type described above with reference to FIGS. 18 and 19). In contrast, FIG. 45 and FIG. 46 depict an alternative embodiment having a different arrangement of sensor contact elements. In this regard, FIG. 45 is a perspective end view of an exemplary embodiment of a rotor 1400 of a fluid pump mechanism, and FIG. 46 is a side view that depicts the rotor 1400 cooperating with a compatible stator 1402 of the fluid pump mechanism. The basic configuration, design, and functionality of the rotor 1400 and the stator 1402 are similar to that described previously with reference to FIGS. 5-14, and common features and aspects will not be redundantly described in detail here. However, the valve timing and arrangement of the stator cam element (not shown in FIG. 46) and the rotor cam element 1404 are similar to that described previously in this section with reference to FIG. 43 and FIG. 44.

The rotor 1400 includes an endcap 1406 having an exposed rim 1408 that faces a counterpart flange 1410 of the stator 1402. The reference surface 1412 of the rotor 1400 and the rotor cam element 1404 are located inside (underneath) the endcap 1406. The rotor 1400 also includes a first sensor contact element 1414 and a second sensor contact element 1416, both of which are located on the rim 1408 or are incorporated into the rim 1408. The shape, size, and location of the first sensor contact element 1414 are consistent with that described above for the first sensor contact element 1312 of the rotor 1308. Likewise, the shape, size, and location of the second sensor contact element 1416 are consistent with that described above for the second sensor contact element 1314 of the rotor 1308. Placement of the sensor contact elements 1414, 1416 on the rim 1408 instead of the reference surface 1412 merely shifts their axial positions; their angular positions relative to the rotor cam element 1404 and relative to the timing of the valves remains effectively the same as that described above. Thus, the first sensor contact element 1414 is located at an angular position that follows the upper edge 1420 of the rotor cam element 1404, and the second sensor contact element 1416 is located at an angular position that follows the first sensor contact element 1414. It should be appreciated that the plots shown in FIG. 43 for normal operating conditions, upstream occlusion conditions, and downstream occlusion conditions also apply to the embodiment depicted in FIG. 45 and FIG. 46.

The sensing element can be located on, incorporated into, or otherwise carried by the stator 1402. The illustrated embodiment employs first and second conductive spring tabs 1424, 1426, which are located on the flange 1410 of the stator 1402. The conductive spring tabs 1424, 1426 extend toward the rim 1408 of the rotor 1400, and are sized and arranged to make physical and electrical contact with the sensor contact elements 1414, 1416 when the axial position of the rotor 1400 is at the nominal baseline position, and when the angular position of the rotor 1400 relative to the stator 1402 aligns the conductive spring tabs 1424, 1426 with the sensor contact elements 1414, 1416. Although not shown in FIG. 46, each conductive spring tab 1424, 1426 can be electrically coupled to the detection circuit to accommodate the detection methodology presented here. In this regard, the conductive spring tabs 1424, 1426 can be connected to the detection circuit in a manner similar to that described above with reference to FIG. 19. Thus, the detection circuit can determine when the two conductive spring tabs 1424, 1426 have been shorted together by one of the sensor contact elements 1414, 1416. For example, FIG. 46 depicts the rotor 1400 and the stator 1402 at a moment when the conductive spring tabs 1424, 1426 are physically and electrically coupled to the sensor contact element 1414.

It should be appreciated that the embodiment described above with reference to FIGS. 17-19 can be alternatively configured to use conductive spring tabs and a sensor contact element 870 on the rim 882 of the endcap 858. In other words, the sensor arrangement shown in FIG. 45 and FIG. 46 can be deployed in an equivalent manner with the rotor 852 and the stator 854

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:
1. A fluid pump mechanism comprising:
a stator comprising a stator cam element having a stator cam surface;
a rotor comprising a reference surface and a rotor cam element having a variable height rising from the reference surface, the rotor cam element cooperating with the stator cam element to axially displace the rotor, relative to the stator, as a function of angular position of the rotor;

a biasing element that provides a biasing force to urge the rotor cam element toward the stator cam element and toward the reference surface; and a force sensor coupled to the rotor, the force sensor generating output levels in response to force imparted thereto, wherein the force imparted to the force sensor varies with axial displacement of the rotor relative to the stator, and the force sensor cooperating with a detection circuit that obtains and processes the output levels following each fluid expulsion period of the fluid pump mechanism and before each fluid intake period of the fluid pump mechanism, to detect occlusions in a fluid path downstream of the fluid pump mechanism;

wherein, under normal operating conditions:
- a complete rotation of the rotor corresponds to one pumping cycle comprising a fluid intake period and a fluid expulsion period;
- during the fluid intake period, the stator cam element is in contact with the rotor cam element;
- during the fluid expulsion period, the rotor cam element disengages the stator cam element, and the biasing element axially displaces the rotor such that the reference surface of the rotor moves toward the stator cam element; and
- after the fluid expulsion period and before a next fluid intake period, the stator cam element is in contact with the reference surface and the force sensor generates nominal output levels that fall within a range of expected output levels; and wherein, under downstream occlusion conditions:
- fluid pressure caused by an occlusion downstream of the fluid pump mechanism prevents the stator cam element from contacting the reference surface after the fluid expulsion period;
- after the fluid expulsion period and before the next fluid intake period, the force sensor generates outlier output levels that fall outside the range of expected output levels and that are indicative of the occlusion; and
- the detection circuit determines the presence of a downstream occlusion in response to the outlier output levels.

2. The fluid pump mechanism of claim 1, wherein:
the detection circuit initiates an alert, alarm, or warning message in response to detecting an occlusion.

3. The fluid pump mechanism of claim 1, wherein the force sensor is positioned between the rotor and the stator to measure force applied by the stator to the force sensor.

4. The fluid pump mechanism of claim 1, wherein the force sensor is positioned between the rotor and the stator to measure force applied by the rotor to the force sensor.

* * * * *